US012752260B2

(12) United States Patent
Li et al.

(10) Patent No.: US 12,752,260 B2
(45) **Date of Patent: *Oct. 6, 2026**

(54) COMPLEX OXIDES FOR REACTIVE OXYGEN SEPARATION AND RELATED APPLICATIONS

(71) Applicant: North Carolina State University, Raleigh, NC (US)

(72) Inventors: Fanxing Li, Raleigh, NC (US); Xijun Wang, Raleigh, NC (US); Emily Krzystowczyk, Raleigh, NC (US); Jian Dou, Raleigh, NC (US); Yunfei Gao, Raleigh, NC (US)

(73) Assignee: North Carolina State University, Raleigh, NC (US)

( * ) Notice: Subject to any disclaimer, the term of this patent is extended or adjusted under 35 U.S.C. 154(b) by 595 days.

This patent is subject to a terminal disclaimer.

(21) Appl. No.: 18/167,159

(22) Filed: Feb. 10, 2023

(65) Prior Publication Data

US 2023/0256422 A1 Aug. 17, 2023

Related U.S. Application Data

(60) Provisional application No. 63/268,013, filed on Feb. 15, 2022.

(51) Int. Cl.
*B01J 23/78* (2006.01)
*B01D 53/86* (2006.01)
(Continued)

(52) U.S. Cl.
CPC .......... *B01J 23/78* (2013.01); *B01D 53/8671* (2013.01); *B01J 23/002* (2013.01); *B01J 23/83* (2013.01);
(Continued)

(58) Field of Classification Search
None
See application file for complete search history.

(56) References Cited

FOREIGN PATENT DOCUMENTS

| | | | | |
|---|---|---|---|---|
| CA | 2337002 C | * | 2/2009 | ......... C01G 45/1264 |
| CN | 104649227 | * | 5/2015 | |

(Continued)

OTHER PUBLICATIONS

Mishra et al. ("Rh promoted perovskites for exceptional "low temperature" methane conversion to syngas", Catalysis Today, 2020, 350, 149-155) (Year: 2020).*

(Continued)

*Primary Examiner* — Sally A Merkling
*Assistant Examiner* — Nicole Lee Quist
(74) *Attorney, Agent, or Firm* — Thomas | Horstemeyer, LLP

(57) ABSTRACT

In one aspect, the disclosure relates to an oxygen-deficient mixed metal perovskite having the formula $Sr_xA_{1-x}Fe_yB_{1-y}O_{3-\delta}$, wherein A can be Ca, K, Y, Ba, La, Sm, or any combination thereof; wherein B can be Co, Cu, Mn, Mg, Ni, Ti, or any combination thereof; wherein x is from 0 to 1; wherein y is from 0 to 1; and wherein δ is from 0 to 0.7. Also disclosed are redox catalysts comprising the oxygen-deficient mixed metal perovskites and methods for chemical looping air separation, chemical looping $CO_2$ splitting, and chemical looping alkane conversion using the disclosed catalysts.

18 Claims, 34 Drawing Sheets
(14 of 34 Drawing Sheet(s) Filed in Color)

(51) Int. Cl.

| | |
|---|---|
| ***B01J 23/00*** | (2006.01) |
| ***B01J 23/83*** | (2006.01) |
| ***B01J 23/889*** | (2006.01) |
| ***C01B 3/40*** | (2006.01) |
| ***C01B 32/40*** | (2017.01) |
| ***C07C 5/42*** | (2006.01) |

(52) U.S. Cl.

CPC ............ *B01J 23/8892* (2013.01); *C01B 3/40* (2013.01); *C01B 32/40* (2017.08); *C07C 5/42* (2013.01); *B01D 2255/2022* (2013.01); *B01D 2255/2042* (2013.01); *B01D 2255/2045* (2013.01); *B01D 2255/2047* (2013.01); *B01D 2255/2073* (2013.01); *B01D 2255/20738* (2013.01); *B01D 2255/20746* (2013.01); *B01D 2255/20753* (2013.01); *B01D 2255/402* (2013.01); *B01D 2257/104* (2013.01); *C01B 2203/0261* (2013.01); *C01B 2203/1058* (2013.01); *C01B 2203/1241* (2013.01); *C07C 2523/78* (2013.01); *C07C 2523/83* (2013.01); *C07C 2523/889* (2013.01)

(56) References Cited

FOREIGN PATENT DOCUMENTS

| | | | |
|---|---|---|---|
| EP | 3542887 A1 | * | 9/2019 |
| KR | 1020110113851 | * | 7/2013 |

OTHER PUBLICATIONS

Sun et al. ("Tailoring Electrochemical Performance of Perovskite Anodes through In Situ Exsolution of Nanocatalysts", ACS Applied materials and interfaces, 2021, 13, 29755-29763) (Year: 2021).*

Li et al. ("Charge transfer dynamics in RuO2/perovskite nanohybrid for enhanced electrocatalysis in solid oxide electrolyzers", Nano Energy, 2019, 57, 186-194) (Year: 2019).*

CN 104649227 machine translation (Year: 2015).*

Vieten "Perovskite Materials Design for Two-Step Solar-Thermochemical Redox Cycles" Technische Universitat Dresden Dissertation, 2019 (Year: 2019).*

Jeen et al "Topotactic phase transformation of the brownmillerite SrCoO2.5 to the perovskite SrCoO3-Î'", Adv. Mater. 2013, 25, 3651-3656 (Year: 2013).*

Azcondo et al, "Thermochemical Energy Storage Using the Phase Transitions Brownmillerite-2H Perovskite-Cubic Perovskite in the CaxSr1-xCoO3-d (x=0 and 0.5) System", ACS Appl. Energy Mater. 2021, 4, 7870-7881 (Year: 2021).*

Dou, Jian et al. "A- and B-site Codoped SrFeO3 Oxygen Sorbents for Enhanced Chemical Looping Air Separation." ChemSusChem vol. 13,2 (2020): 385-393. doi:10.1002/cssc.201902698.

Dou, J. et al., "Sr1-xCaxFe1-yCoyO3-δ as facile and tunable oxygen sorbents for chemical looping air separation", Journal of Physics: Energy, 2020, 2, 025007.

Krzystowczyk, Emily et al. "Substituted SrFeO3 as robust oxygen sorbents for thermochemical air separation: correlating redox performance with compositional and structural properties." Physical chemistry chemical physics : PCCP vol. 22,16 (2020): 8924-8932. doi:10.1039/d0cp00275e.

Luongo, Giancarlo et al. "Structural and thermodynamic study of Ca A- or Co B-site substituted SrFeO3-δ perovskites for low temperature chemical looping applications." Physical chemistry chemical physics : PCCP vol. 22,17 (2020): 9272-9282. doi:10.1039/d0cp01049a.

Zhang, Junshe et al. "Perovskite nanocomposites as effective CO2-splitting agents in a cyclic redox scheme." Science advances vol. 3,8 e1701184. Aug. 30, 2017, doi:10.1126/sciadv.1701184.

* cited by examiner $$\tau = \frac{r_O}{r_B} - n_A\left(n_A - \frac{r_A/r_B}{\ln(r_A/r_B)}\right)$$

COMPLEX OXIDES FOR REACTIVE OXYGEN SEPARATION AND RELATED APPLICATIONS

CROSS REFERENCE TO RELATED APPLICATIONS

This application claims the benefit of U.S. Provisional Application No. 63/268,013, filed on Feb. 15, 2022, which is incorporated herein by reference in its entirety.

STATEMENT REGARDING FEDERALLY SPONSORED RESEARCH OR DEVELOPMENT

This invention was made with government support under grant number CBET1510900 awarded by the National Science Foundation and grant number DE-FE0031521 awarded by the U.S. Department of Energy. The government has certain rights in the invention.

BACKGROUND

As an emerging strategy toward clean, efficient, and cost-effective energy and chemical conversion, chemical looping (CL) has drawn substantial attention in various important applications such as air separation, indirect combustion for $CO_2$ capture, solar thermal water or $CO_2$ splitting, and selective oxidation for chemical production. The CL concept involves decoupling an overall reaction into multiple reduction and oxidization sub-reactions, whereby an intermediate, also known as an oxygen carrier or a redox catalyst, facilitates such sub-reactions by releasing or replenishing oxygen under temperature and/or oxygen partial pressure ($P_{O2}$) swings (FIG. 1A). Therefore, the properties of the oxygen carriers, often composed of transition metal oxides, play a critical role towards the overall performances of a CL process.

Despite of the tremendous efforts in oxygen carrier development, development and optimization of oxygen carriers still rely primarily on heuristics and trial-and-error. Meanwhile, the design space for oxygen carriers have significantly expanded from supported monometallic transition metal oxide to various families of mixed oxides. However, possible compositions of mixed oxides are practically infinite and a need exists to narrow down the material design space for oxygen carrier development and optimization.

Despite advances in oxygen carrier/redox catalyst research, there is still a large space of mixed-metal perovskites, encompassing a nearly infinite number of variations, that remains unexplored. Furthermore, there is a scarcity of methods that are effective for predicting multiple perovskite-based compounds possessing the desired catalytic properties without the need to expend effort using a trial and error approach. These needs and other needs are satisfied by the present disclosure.

SUMMARY

In accordance with the purpose(s) of the present disclosure, as embodied and broadly described herein, the disclosure, in one aspect, relates to an oxygen-deficient mixed metal perovskite having the formula $Sr_xA_{1-x}Fe_yB_{1-y}O_{3-\delta}$, wherein A can be Ca, K, Y, Ba, La, Sm, or any combination thereof; wherein B can be Co, Cu, Mn, Mg, Ni, Ti, or any combination thereof; wherein x is from 0 to 1; wherein y is from 0 to 1; and wherein δ is from 0 to 0.7. Also disclosed are redox catalysts comprising the oxygen-deficient mixed metal perovskites and methods for chemical looping air separation, chemical looping $CO_2$ splitting, and chemical looping alkane conversion using the disclosed catalysts.

Other systems, methods, features, and advantages of the present disclosure will be or become apparent to one with skill in the art upon examination of the following drawings and detailed description. It is intended that all such additional systems, methods, features, and advantages be included within this description, be within the scope of the present disclosure, and be protected by the accompanying claims. In addition, all optional and preferred features and modifications of the described embodiments are usable in all aspects of the disclosure taught herein. Furthermore, the individual features of the dependent claims, as well as all optional and preferred features and modifications of the described embodiments are combinable and interchangeable with one another.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

Many aspects of the present disclosure can be better understood with reference to the following drawings. The components in the drawings are not necessarily to scale, emphasis instead being placed upon clearly illustrating the principles of the present disclosure. Moreover, in the drawings, like reference numerals designate corresponding parts throughout the several views.

(FIG. 1A) Schematic illustration and potential applications. (FIG. 1B) Ellingham diagram depicting the correspondence between oxygen carrier redox properties and applications.

(FIG. 2A) Density Functional Theory (DFT) model construction, high-throughput calculations, and materials screening. (FIG. 2B) Machine Learning (ML) steps for the training, evaluation, and prediction of perovskite datasets.

(FIG. 3A) Formula of the modified tolerance factor (τ) for $ABO_3$ perovskites. (FIG. 3B) Comparison of Goldschmidt's and the Bartel et al.'s modified tolerance factor for the 2401 $Sr_xA_{1-x}FeyB_{1-y}O_3$ samples considered. (FIG. 3C) Heatmap and (FIG. 3D) Frequency counts of the modified tolerance factors of the 2401 $Sr_xA_{1-x}Fe_yB_{1-y}O_3$ compositions considered.

(FIG. 4A) Schematic of the slope of ΔG in different δ ranges. (FIG. 4B) ΔG of each doped species as δ changes from 0.3125 to 0.4375 at 400 and 950° C.

(FIG. 5A) Key performance parameters (PCC and MAE) of different supervised ML algorithms. (FIG. 5B) Comparison of ΔG values computed by DFT with those predicted by RF within studied δ ranges at 400 and 950° C. (FIG. 5C) DFT Verification of RF predicted ΔGs for 60 randomly selected datasets containing 5 cation elements. Here the RF model trained from the 2003 samples containing 2-4 cation elements were used to predict the ΔGs of the samples containing 5 cation elements.

(FIG. 6A) A heatmap of the screened candidates for CL air separation (CLAS) at 700° C.

within the δ range of 0.3125~0.4375. (FIG. 6B) Experimental oxygen capacity, recovery, and usable capacity of the samples tested for CLAS. Squares and circles represent DFT and ML predicted samples, respectively. (FIG. 6C) A heatmap of the screened promising candidates for chemical looping (CL) $CO_2/H_2O$ splitting at 950° C. within the δ range of 0.3125~0.4375. (FIG. 6D) Experimental syngas yield and $CO_2$ conversion of the samples tested for CL $CO_2$ splitting. Squares and circles represent the DFT and ML predicted samples, respectively.

Additional advantages of the invention will be set forth in part in the description which follows, and in part will be obvious from the description, or can be learned by practice of the invention. The advantages of the invention will be realized and attained by means of the elements and combinations particularly pointed out in the appended claims. It is to be understood that both the foregoing general description and the following detailed description are exemplary and explanatory only and are not restrictive of the invention, as claimed.

DETAILED DESCRIPTION

Disclosed herein are mixed metal oxides for reactive air separation, chemical looping (CL) $CO_2/H_2O$ splitting, and related applications. In another aspect, by rationally substituting the A- and/or B-site cations of an oxygen-deficient mixed metal perovskite having the formula $Sr_xA_{1-x}Fe_yBi_{1-y}O_{3-\delta}$, the equilibrium oxygen partial pressure of this material can be tailored over 20 orders of magnitude, covering wide ranges of redox potential and temperatures (i.e., 10-25 atm at 950° C.→1 atm at 400° C.). Also disclosed herein are numerous high performance, complex oxides composed of 4 or 5 cation elements. In another aspect, these mixed oxides can be used for cyclic reactive separations to produce and/or remove oxygen and use such oxygen for catalytic applications. In a further aspect, the kinetic properties and product selectivity of these mixed oxides can be tailored by surface modification, largely broadening their application ranges.

Figure 1A:
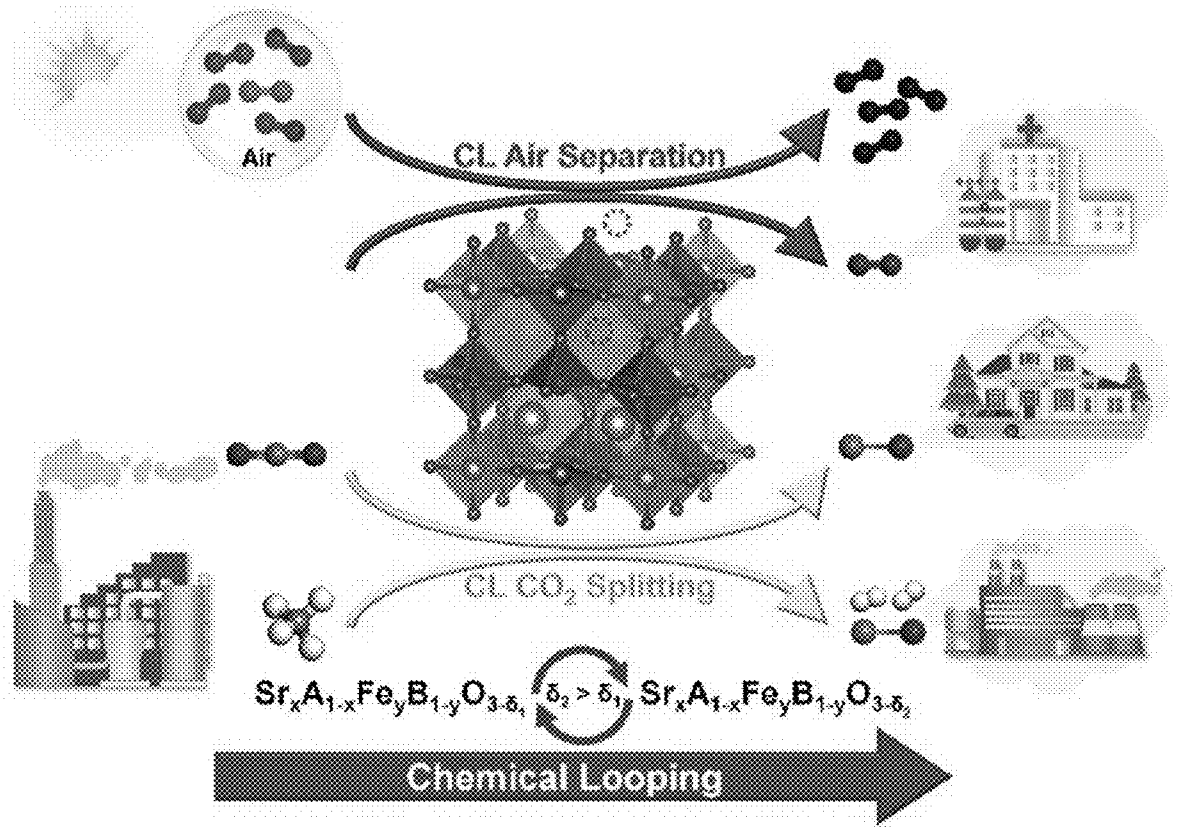
FIGS. 1A-1B show the disclosed chemical looping strategy.
Figure 1B:
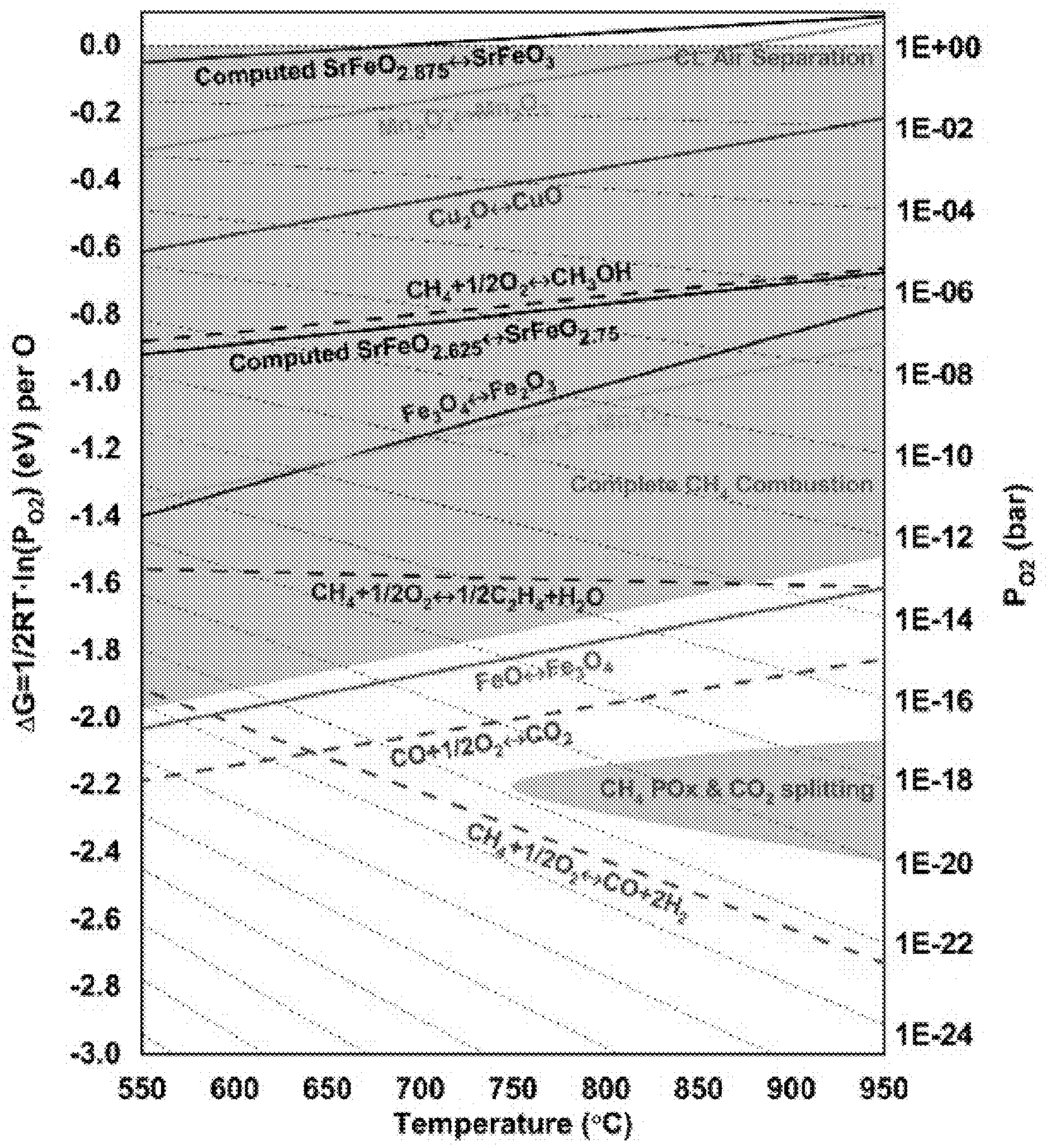

In one aspect, oxygen carrier optimization requires comprehensive consideration of redox kinetics, oxygen carrying capacity, redox cycling stability, cost, environmental impact, and surface catalytic properties when applied towards chemical production. In a further aspect, the complexity of these intertwined factors makes it impractical for a comprehensive investigation from a computational standpoint, especially considering the dynamic nature of chemical looping reactions. In a further aspect, the redox thermodynamic properties of the oxygen carriers, quantified as equilibrium oxygen chemical potential ($\mu_{O2}$) or partial pressure ($P_{O2}$), represent the utmost important parameter and a prerequisite for oxygen carrier selection. Depending on the applications, the required $P_{O2}$ may, in one aspect, vary by up to 20 orders of magnitudes (FIG. 1B). In another aspect, it is anticipated that high $P_{O2}$ would promote oxygen donation while low $P_{O2}$ would favor oxygen storage or replenishment, making the equilibrium oxygen chemical potential a promising descriptor to down-select oxide candidates for oxygen carrier design.

In an aspect, first-principles density function theory (DFT) calculations have shown advantages in computing redox thermodynamics for oxygen carriers. In another aspect, recent studies have demonstrated the correspondence between the computed oxygen vacancy formation energies and the experimental $P_{O2}$ swings; these studies have demonstrate excellent effectiveness for material screening. However, existing work is still subject to one or more of the following limitations: 1) The oxide model structures were generally simulated with small unit cells, making it difficult to determine the effects of oxygen vacancy concentration, which dynamically changes over the course of the redox reactions; 2) Thermodynamic properties were generally calculated using a defect-free model as the starting point, but the actual oxygen carriers rarely stay near a pristine state; 3) The various possible vacancy and substitution site combinations were not comprehensively considered. In an aspect, these limitations can affect the accuracy and applicability of the models especially for applications with small target $P_{O2}$ ranges such as CL air separation (CLAS) (FIG. 1B). Therefore, a more comprehensive simulation scheme closer to real world conditions is highly desired. In another aspect, advanced data-driven techniques such as ML, which have been successfully applied to assist materials design, have rarely been used for CL applications, with the exception of one study investigating Mn based oxygen carriers based on experimental performance and characterization of 19 Mn-containing ores.

Perovskite structured strontium ferrite ($SrFeO_{3-\delta}$) has been widely investigated for CLAS and CL with oxygen uncoupling (CLOU) due to its outstanding oxygen release and uptake capabilities. In another aspect, finding the optimal doping elements and concentrations for specific applications still rely heavily on trial-and-error. In yet another aspect, further expanding the redox property range of doped $SrFeO_{3-\delta}$ towards ultra-low $P_{O2}$ applications such as $CO_2$ splitting is highly desirable.

Figure 2A:
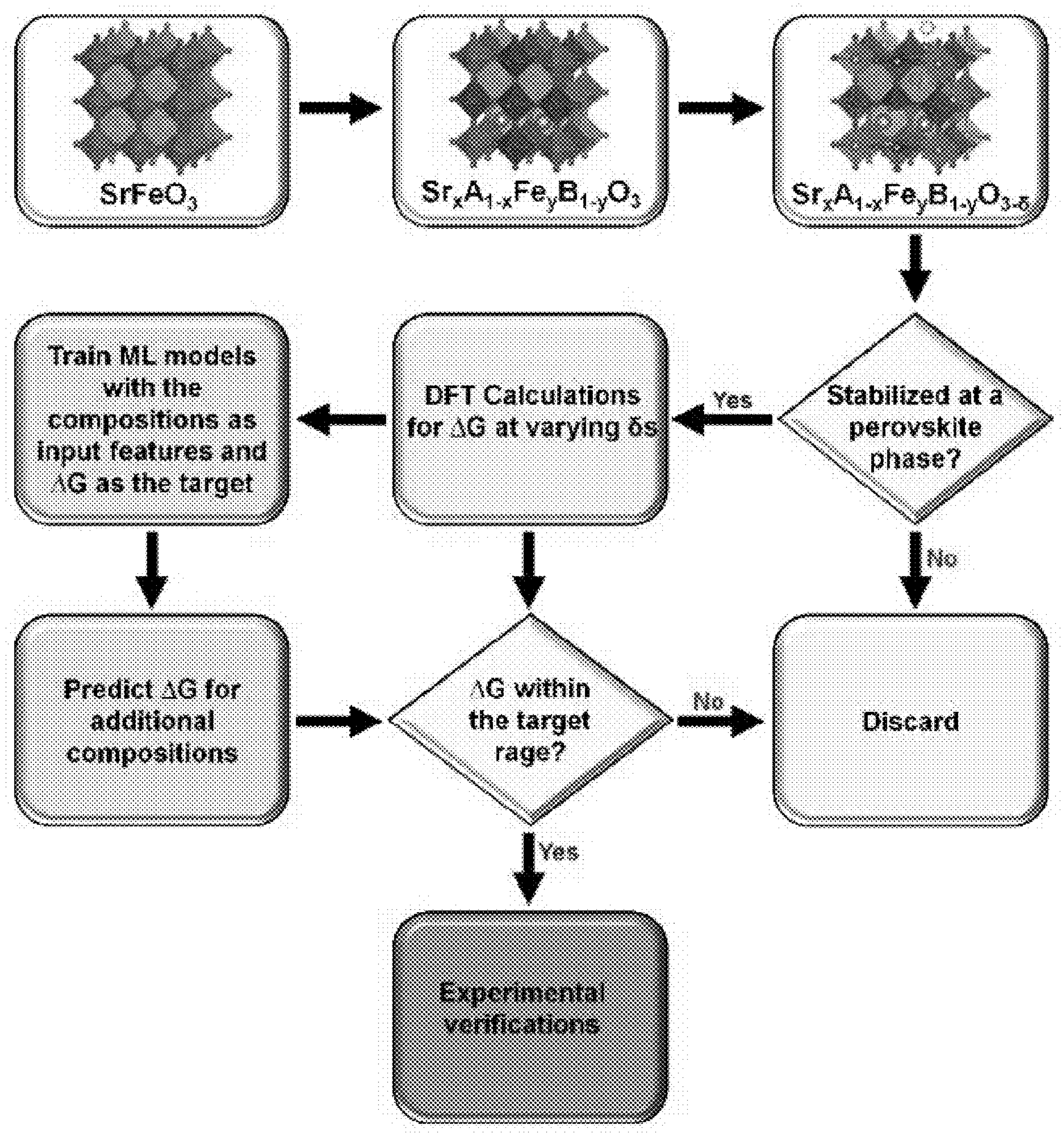
FIGS. 2A-2B show flowcharts for high throughput materials screening.
Figure 2B:
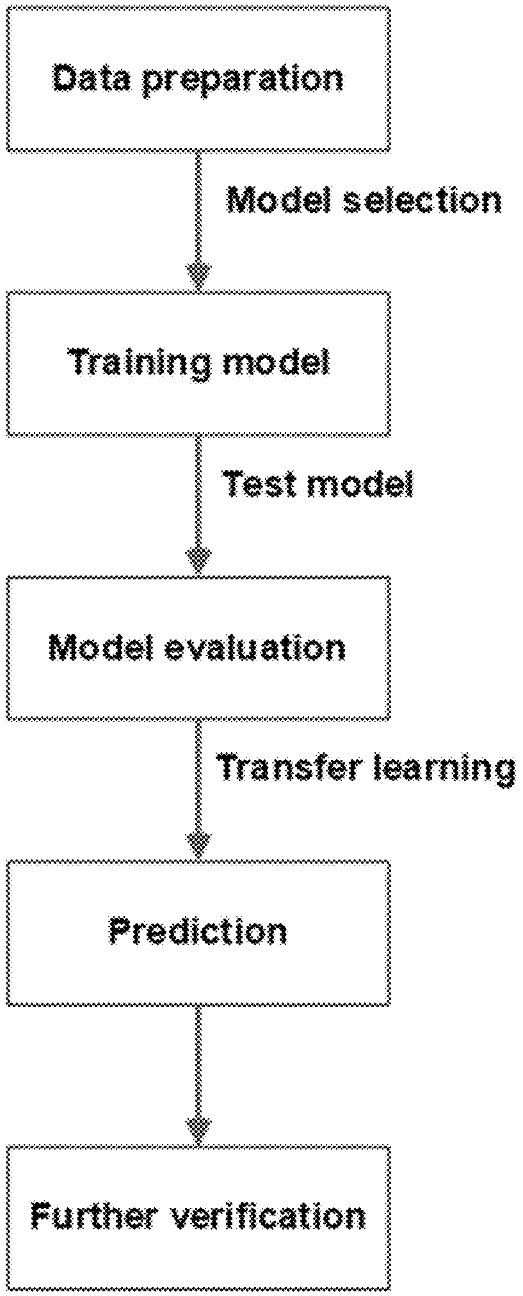

Disclosed herein is a method for rationally engineering the oxygen chemical potentials of A- and/or B-site substituted $SrFeO_{3-\delta}$ perovskites for a wide range of CL applications. In one aspect, DFT based high throughput calculations, with procedures depicted in FIG. 2A, were applied to investigate $Sr_xA_{1-x}Fe_yB_{1-y}O_{3-\delta}$ perovskites with 2401 distinct cation compositions. In a further aspect, DFT calculated ΔGs at various oxygen non-stoichiometries (δs) and temperatures were used to screen out promising oxygen carrier materials for CLAS and CL based $CO_2$ splitting. In still another aspect, the effectiveness of the DFT based high throughput screening is supported by 21 literature reported oxygen carriers and 15 new carrier compositions prepared and tested in the current study. In one aspect, the DFT results were used to develop a machine learning model to predict the ΔGs of 227,273 $Sr_x(A/A')_{1-x}Fe_y(B/B')_{1-y}O_{3-\delta}$ high-entropy perovskites containing 5 cation elements. In another aspect machine learning protocol, as illustrated in FIG. 2B, contains the following steps: (1) Data preparation, which includes data collection, normalization, and splitting the data into training and test datasets, as well as defining the input features; (2) Model selection, which involves selecting ML algorithms for the studied datasets based on the trade-off between time-consumption and accuracy; (3) Training model, referring to training the hyperparameters within the framework of the selected algorithm using the training sets to improve the prediction of the ML model; (4) Model evaluation, which entails testing the ML model against an unused dataset (test set) to evaluate its performances; (5) Predict the values of the new targets (ΔGs) for new perovskite compositions, followed by additional DFT and/or experimental verifications. In a further aspect, accuracy of the ML model was validated by additional DFT calculations and experiments. In one aspect, these findings not only significantly expand the materials design space for CL applications but also provide new insights and theoretical guidance for oxygen carrier optimization.

Oxygen-Deficient Mixed Metal Perovskites

Disclosed herein are oxygen-deficient mixed metal perovskites having the formula $Sr_xA_{1-x}Fe_yB_{1-y}O_{3-\delta}$, wherein A is selected from Ca, K, Y, Ba, La, Sm, or any combination thereof; wherein B is selected from Co, Cu, Mn, Mg, Ni, Ti, or any combination thereof; wherein x is from 0 to 1, wherein y is from 0 to 1, and wherein δ is from 0 to 0.5.

In one aspect, x can be 0, or can be from about 0.125 to about 0.875, or can be 0, 0.125, 0.25, 0.375, 0.5, 0.625, 0.75, 0.875, or about 1, or a combination of any of the foregoing values, or a range encompassing any of the foregoing values.

In another aspect, y can be 0, or can be from about 0.125 to about 0.875, or can be 0, 0.125, 0.25, 0.375, 0.5, 0.625, 0.75, 0.875, or about 1, or a combination of any of the foregoing values, or a range encompassing any of the foregoing values.

In still another aspect, δ can vary during the chemical looping process. In one aspect, δ can be between 0 and 0.7, optionally between 0.01 and 0.45 depending on the degree of reduction/oxidation in the chemical looping process.

In another aspect, the oxygen-deficient mixed metal perovskite can have 4 different cations, or can have 5 different cations. In another aspect, A can be selected from Ba, Ca, K, La, Sm, Y, or a combination of La and Sm, while B can be selected from Co, Mn, Mg, Cu, Ni, a combination of Co and Ni, a combination of Mg and Ti, or a combination of Mn and Mg. In some aspects, the oxygen-deficient mixed metal perovskite can be further impregnated with up to about 1 wt % Ru, or with about 0.1, 0.2, 0.3, 0.4, 0.5, 0.6, 0.7, 0.8, 0.9, or about 1 wt % Ru, or a combination of any of the foregoing values, or a range encompassing any of the foregoing values. In other aspects, the oxygen-deficient mixed metal perovskite can be further impregnated with up to about 0.5 wt % Rh, or with about 0.1, 0.2, 0.3, 0.4, or about 0.5 wt % Rh, or a combination of any of the foregoing values, or a range encompassing any of the foregoing values.

In another aspect, the oxygen-deficient mixed metal perovskite can further include an alkali metal salt or mixed alkali metal oxide or any combination thereof. In one aspect, the alkali metal salt can be $a_2WO_4$, $Na_2MoO_4$, $Na_2W_2O_7$, $Na_4Mg(WO_4)_3$, $Li_2CO_3$, $Na_2CO_3$, $K_2CO_3$, NaBr, LiBr, KBr, LiI, NaI, KI, $Na_2W_4O_{13}$, and the mixed alkali metal oxide can be $KFeO_2$ or another mixed alkali metal oxide. In any of these aspects, the oxygen-deficient mixed metal perovskite can be impregnated with up to 30 wt % alkali metal salt or mixed alkali metal oxide, or can be impregnated with 1, 2, 3, 4, 5, 6, 7, 8, 9, 10, 11, 12, 13, 14, 15, 16, 17, 18, 19, 20, 21, 22, 23, 24, 25, 26, 27, 28, 29, or about 30 wt % alkali metal salt or mixed alkali metal oxide, or a combination of any of the foregoing values, or a range encompassing any of the foregoing values.

In any of these aspects, the oxygen-deficient mixed metal perovskite can have a formula selected from: $Sr_{0.875}Ba_{0.125}Fe_{0.5}Co_{0.5}O_{3-\delta}$, $Sr_{0.75}Ca_{0.25}Fe_{0.75}Mn_{0.25}O_{3-\delta}$, $Sr_{0.875}Ca_{0.125}Fe_{0.625}Mg_{0.375}O_{3-\delta}$, $Sr_{0.75}Ca_{0.25}CoO_{3-\delta}$, $Sr_{0.875}K_{0.125}CoO_{3-\delta}$, $Sr_{0.875}La_{0.125}Fe_{0.75}Cu_{0.25}O_{3-\delta}$, $Sr_{0.875}La_{0.125}Fe_{0.125}Co_{0.875}O_{3-\delta}$, $Sr_{0.75}Sm_{0.25}Fe_{0.125}Co_{0.875}O_{3-\delta}$, $Sir_{0.875}Y_{0.125}Fe_{0.75}Ni_{0.25}O_{3-\delta}$, $Sr_{0.625}Ca_{0.375}Fe_{0.75}Cu_{0.25}O_{3-\delta}$, $Sr_{0.875}Ba_{0.125}Fe_{0.375}Mn_{0.625}O_{3-\delta}$, $Sir_{0.75}Y_{0.25}Fe_{0.125}Co_{0.875}O_{3-\delta}$, $Sr_{0.875}K_{0.125}Fe_{0.75}Co_{0.125}Ni_{0.125}O_{3-\delta}$, $Sir_{0.5}Ba_{0.5}Fe_{0.625}Mg_{0.25}Ti_{0.125}O_{3-\delta}$, $Sr_{0.875}Ca_{0.125}Fe_{0.75}Co_{0.125}Ni_{0.125}O_{3-\delta}$, $Sr_{0.875}La_{0.125}Fe_{0.75}Co_{0.125}Ni_{0.125}O_{3-\delta}$, $Sr_{0.875}Sm_{0.125}Fe_{0.75}Co_{0.125}Ni_{0.125}O_{3-\delta}$, $SrFe_{0.5}Cu_{0.125}Mn_{0.125}Mg_{0.25}O_{3-\delta}$, $Sr_{0.5}Y_{0.5}Fe_{0.125}Ti_{0.875}O_{3-\delta}$, $Sr_{0.375}Y_{0.625}Fe_{0.5}Ti_{0.5}O_{3-\delta}$, $Sir_{0.5}Y_{0.5}Fe_{0.375}Ti_{0.625}O_{3-\delta}$, $Sr_{0.375}Sm_{0.625}Fe_{0.375}Ti_{0.625}O_{3-\delta}$, $LaFe_{0.35}Mn_{0.65}O_{3-\delta}$, $YFe_{0.875}Co_{0.125}O_{3-\delta}$, $Sr_{0.125}Sm_{0.875}Fe_{0.75}Cu_{0.25}O_{3-\delta}$, $Sr_{0.375}La_{0.375}Sm_{0.25}Fe_{0.75}Ti_{0.25}O_{3-\delta}$, $Sr_{0.375}La_{0.5}Sm_{0.125}Fe_{0.75}Ti_{0.25}O_{3-\delta}$, and $Sr_{0.125}La_{0.625}Sm_{0.25}Fe_{0.875}Ti_{0.125}O_{3-\delta}$.

Also disclosed herein are redox catalysts that are or include the disclosed oxygen-deficient mixed metal perovskites.

Method for Chemical Looping Air Separation (CLAS)

In one aspect, disclosed herein is a method for chemical looping air separation (CLAS), the method including at least the steps of:

(i) contacting a gas mixture comprising oxygen with the oxygen-deficient mixed metal perovskite of any one of claims 1-12 or the redox catalyst of claim 13, wherein the contacting creates a reduced level of oxygen deficiency in the perovskite; and (ii) exposing the perovskite having the reduced level of oxygen deficiency to a vacuum or steam purge to release concentrated oxygen while recreating the oxygen-deficient perovskite of (i).

In another aspect, the gas mixture can include a partial pressure of oxygen from about 0.01 atm to about 0.2 atm prior to performing the method, or about 0.01, 0.02, 0.03, 0.04, 0.05, 0.06, 0.07, 0.08, 0.09, 0.1, 0.11, 0.12, 0.13, 0.14, 0.15, 0.16, 0.17, 0.18, 0.19, or about 0.2 atm, or a range encompassing any of the foregoing values.

In another aspect, the gas mixture can be substantially free of oxygen following performing the method. In one aspect, the gas mixture can be air. In another aspect, the method can additionally include the step of collecting the oxygen separated from the gas mixture.

Method for Chemical Looping $CO_2$ Splitting and Methane Conversion

In one aspect, disclosed herein is a method for chemical looping $CO_2$ splitting, the method including at least the step of contacting a gas mixture containing carbon dioxide with the oxygen-deficient mixed metal perovskite or redox catalyst disclosed herein.

In one aspect, at least 80% of the carbon dioxide is converted to carbon monoxide and oxygen, or at least 85%, 90%, 95%, or 99% of the carbon dioxide is converted to carbon monoxide and oxygen, or substantially all of the carbon dioxide is converted to carbon monoxide and oxygen.

In one aspect, disclosed herein is a method for chemical looping methane conversion, the method including at least the step of contacting a gas mixture containing methane with the oxygen-deficient mixed metal perovskite or redox catalyst disclosed herein.

In one aspect, at least 70% of the methane is converted to syngas, or at least 75, 80, 85%, 90%, 95%, or 99% of the methane is converted to syngas, or substantially all of the methane is converted to syngas.

Method for Chemical Looping Oxidative Dehydrogenation of Light Alkanes and Alkyl-Benzenes In one aspect, he materials disclosed herein can facilitate Chemical Looping Oxidative Dehydrogenation (CL-ODH) of light alkanes and alkyl-benzenes. In another aspect, the surface of the oxides can be modified by an alkali metal salt (e.g. $Na_2WO_4$, $Na_2MoO_4$, $Na_2W_2O_7$, $Na_4Mg(WO_4)_3$, $Li_2CO_3$, $Na_2CO_3$, $K_2CO_3$, NaBr, LiBr, KBr, LiI, NaI, KI, and/or $Na_2W_4O_{13}$) or mixed alkali metal oxide (e.g. $KFeO_2$), leading to effective redox catalysts for CL-ODH applications. In a further aspect, sample applications include, but are not limited to, ethane CL-ODH to ethylene, propane to propylene, oxidative cracking of naphtha, CL oxidative coupling of methane, CL-ODH of ethylbenzene to styrene, CL-ODH of cumene to alpha methylstyrene. A non-limiting, generalized cyclic reaction scheme is given below:

$$C_nH_{m+2}+1/(\delta'-\delta)Sr_xA_{1-x}Fe_yB_{1-y}O_{3-\delta}\rightarrow C_nH_m+1/(\delta'-\delta)Sr_xA_{1-x}Fe_yB_{1-y}O_{3-\delta'}+H_2O$$

$$1/(\delta'-\delta)Sr_xA_{1-x}Fe_yB_{1-y}O_{3-\delta'}+1/2O_2\rightarrow 1/(\delta'-\delta)Sr_xA_{1-x}Fe_yB_{1-y}O_{3-\delta}$$

FIGS. 10-13 show exemplary reactor schematics for accomplishing the disclosed reactions using the oxygen-deficient mixed metal perovskites as catalysts.

Many modifications and other embodiments disclosed herein will come to mind to one skilled in the art to which the disclosed compositions and methods pertain having the benefit of the teachings presented in the foregoing descriptions and the associated drawings. Therefore, it is to be understood that the disclosures are not to be limited to the specific embodiments disclosed and that modifications and other embodiments are intended to be included within the scope of the appended claims. The skilled artisan will recognize many variants and adaptations of the aspects described herein. These variants and adaptations are intended to be included in the teachings of this disclosure and to be encompassed by the claims herein.

Although specific terms are employed herein, they are used in a generic and descriptive sense only and not for purposes of limitation.

As will be apparent to those of skill in the art upon reading this disclosure, each of the individual embodiments described and illustrated herein has discrete components and features which may be readily separated from or combined with the features of any of the other several embodiments without departing from the scope or spirit of the present disclosure.

Any recited method can be carried out in the order of events recited or in any other order that is logically possible. That is, unless otherwise expressly stated, it is in no way intended that any method or aspect set forth herein be construed as requiring that its steps be performed in a specific order. Accordingly, where a method claim does not specifically state in the claims or descriptions that the steps are to be limited to a specific order, it is no way intended that an order be inferred, in any respect. This holds for any possible non-express basis for interpretation, including matters of logic with respect to arrangement of steps or operational flow, plain meaning derived from grammatical organization or punctuation, or the number or type of aspects described in the specification.

All publications mentioned herein are incorporated herein by reference to disclose and describe the methods and/or materials in connection with which the publications are cited. The publications discussed herein are provided solely for their disclosure prior to the filing date of the present application. Nothing herein is to be construed as an admission that the present invention is not entitled to antedate such publication by virtue of prior invention. Further, the dates of publication provided herein can be different from the actual publication dates, which can require independent confirmation.

While aspects of the present disclosure can be described and claimed in a particular statutory class, such as the system statutory class, this is for convenience only and one of skill in the art will understand that each aspect of the present disclosure can be described and claimed in any statutory class.

It is also to be understood that the terminology used herein is for the purpose of describing particular aspects only and is not intended to be limiting. Unless defined otherwise, all technical and scientific terms used herein have the same meaning as commonly understood by one of ordinary skill in the art to which the disclosed compositions and methods belong. It will be further understood that terms, such as those defined in commonly used dictionaries, should be interpreted as having a meaning that is consistent with their meaning in the context of the specification and relevant art and should not be interpreted in an idealized or overly formal sense unless expressly defined herein.

Prior to describing the various aspects of the present disclosure, the following definitions are provided and should be used unless otherwise indicated. Additional terms may be defined elsewhere in the present disclosure.

Definitions

As used herein, "comprising" is to be interpreted as specifying the presence of the stated features, integers, steps, or components as referred to, but does not preclude the presence or addition of one or more features, integers, steps, or components, or groups thereof. Moreover, each of the terms "by," "comprising," "comprises," "comprised of," "including," "includes," "included," "involving," "involves," "involved," and "such as" are used in their open, non-limiting sense and may be used interchangeably. Further, the term "comprising" is intended to include examples and aspects encompassed by the terms "consisting essentially of" and "consisting of." Similarly, the term "consisting essentially of" is intended to include examples encompassed by the term "consisting of.

As used in the specification and the appended claims, the singular forms "a," "an" and "the" include plural referents unless the context clearly dictates otherwise. Thus, for example, reference to "a cation," "a redox catalyst," or "a gas mixture," includes, but is not limited to, mixtures or combinations of two or more such cations, redox catalysts, or gas mixtures, and the like.

It should be noted that ratios, concentrations, amounts, and other numerical data can be expressed herein in a range format. It will be further understood that the endpoints of each of the ranges are significant both in relation to the other endpoint, and independently of the other endpoint. It is also understood that there are a number of values disclosed herein, and that each value is also herein disclosed as "about" that particular value in addition to the value itself. For example, if the value "10" is disclosed, then "about 10" is also disclosed. Ranges can be expressed herein as from "about" one particular value, and/or to "about" another particular value. Similarly, when values are expressed as approximations, by use of the antecedent "about," it will be understood that the particular value forms a further aspect. For example, if the value "about 10" is disclosed, then "10" is also disclosed.

When a range is expressed, a further aspect includes from the one particular value and/or to the other particular value. For example, where the stated range includes one or both of the limits, ranges excluding either or both of those included limits are also included in the disclosure, e.g. the phrase "x to y" includes the range from 'x' to 'y' as well as the range greater than 'x' and less than 'y.' The range can also be expressed as an upper limit, e.g. 'about x, y, z, or less' and should be interpreted to include the specific ranges of 'about x,' 'about y', and 'about z' as well as the ranges of 'less than x', less than y', and 'less than z'. Likewise, the phrase 'about x, y, z, or greater' should be interpreted to include the specific ranges of 'about x,' 'about y,' and 'about z' as well as the ranges of 'greater than x,' greater than y,' and 'greater than z.' In addition, the phrase "about 'x' to 'y'", where 'x' and 'y' are numerical values, includes "about 'x' to about 'y'".

It is to be understood that such a range format is used for convenience and brevity, and thus, should be interpreted in a flexible manner to include not only the numerical values explicitly recited as the limits of the range, but also to include all the individual numerical values or sub-ranges encompassed within that range as if each numerical value and sub-range is explicitly recited. To illustrate, a numerical range of "about 0.1% to 5%" should be interpreted to include not only the explicitly recited values of about 0.1% to about 5%, but also include individual values (e.g., about 1%, about 2%, about 3%, and about 4%) and the sub-ranges (e.g., about 0.5% to about 1.1%; about 5% to about 2.4%; about 0.5% to about 3.2%, and about 0.5% to about 4.4%, and other possible sub-ranges) within the indicated range.

As used herein, the terms "about," "approximate," "at or about," and "substantially" mean that the amount or value in question can be the exact value or a value that provides equivalent results or effects as recited in the claims or taught herein. That is, it is understood that amounts, sizes, formulations, parameters, and other quantities and characteristics are not and need not be exact, but may be approximate and/or larger or smaller, as desired, reflecting tolerances, conversion factors, rounding off, measurement error and the like, and other factors known to those of skill in the art such that equivalent results or effects are obtained. In some circumstances, the value that provides equivalent results or effects cannot be reasonably determined. In such cases, it is generally understood, as used herein, that "about" and "at or about" mean the nominal value indicated ±10% variation unless otherwise indicated or inferred. In general, an amount, size, formulation, parameter or other quantity or characteristic is "about," "approximate," or "at or about" whether or not expressly stated to be such. It is understood that where "about," "approximate," or "at or about" is used before a quantitative value, the parameter also includes the specific quantitative value itself, unless specifically stated otherwise.

As used herein, the term "effective amount" refers to an amount that is sufficient to achieve the desired modification of a physical property of the composition or material. For example, an "effective amount" of a catalyst refers to an amount that is sufficient to achieve the desired improvement in the property modulated by the formulation component, e.g. achieving the desired level of syngas production in a methane conversion reaction. The specific level required as an effective amount will depend upon a variety of factors including the amount and purity of the gas mixture to be converted, flow rate of the gas mixture through a reactor, and the like.

As used herein, the terms "optional" or "optionally" means that the subsequently described event or circumstance can or cannot occur, and that the description includes instances where said event or circumstance occurs and instances where it does not.

"Chemical looping" as used herein refers to the decoupling of an overall reaction into multiple reduction and oxidization sub-reactions, whereby an intermediate, also known as an oxygen carrier or a redox catalyst, facilitates such sub-reactions by releasing or replenishing oxygen under temperature and/or oxygen partial pressure ($P_{O2}$) swings "Syngas" is a fuel gas mixture containing carbon monoxide and hydrogen as well as, occasionally, some amount of carbon dioxide. In one aspect, methane can be converted to syngas using the oxygen-deficient mixed metal perovskites and redox catalysts disclosed herein.

Unless otherwise specified, pressures referred to herein are based on atmospheric pressure (i.e. one atmosphere).

Now having described the aspects of the present disclosure, in general, the following Examples describe some additional aspects of the present disclosure. While aspects of the present disclosure are described in connection with the following examples and the corresponding text and figures, there is no intent to limit aspects of the present disclosure to this description. On the contrary, the intent is to cover all alternatives, modifications, and equivalents included within the spirit and scope of the present disclosure.

ASPECTS

The present disclosure can be described in accordance with the following numbered Aspects, which should not be confused with the claims.

Aspect 1. An oxygen-deficient mixed metal perovskite comprising the formula $Sr_x(A/A')_{1-x}Fe_y(B/B')_{1-y}O_{3-\delta}$, wherein A/A' comprises Ca, K, Y, Ba, La, Sm, or any combination thereof;

wherein B/B' comprises Co, Cu, Mn, Mg, Ni, Ti, or any combination thereof;

wherein x is from 0 to 1;

wherein y is from 0 to 1; and wherein δ is from 0 to 0.7.

Aspect 2. The oxygen-deficient mixed metal perovskite of aspect 1, wherein the oxygen-deficient mixed metal perovskite comprises 4 or 5 cations.

Aspect 3. The oxygen-deficient mixed metal perovskite of any one of the preceding aspects, wherein A is selected from Ba, Ca, K, La, Sm, Y, or a combination of La and Sm.

Aspect 4. The oxygen-deficient mixed metal perovskite of any one of the preceding aspects, wherein B is selected from Co, Mn, Mg, Cu, Ni, a combination of Co and Ni, a combination of Mg and Ti, or a combination of Mn and Mg.

Aspect 5. The oxygen-deficient mixed metal perovskite of any one of the preceding aspects, wherein the oxygen-deficient mixed metal perovskite further comprises up to 1 wt % Ru.

Aspect 6. The oxygen-deficient mixed metal perovskite of any one of the preceding aspects, wherein the oxygen-deficient mixed metal perovskite further comprises up to 0.5 wt % Rh.

Aspect 7. The oxygen-deficient mixed metal perovskite of any one of the preceding aspects, wherein the oxygen-deficient mixed metal perovskite is further loaded with up to 30 wt % alkali metal salt, mixed alkali metal oxide, or any combination thereof.

Aspect 8. The oxygen-deficient mixed metal perovskite of aspect 7, wherein the alkali metal salt or mixed alkali metal oxide comprises $Na_2WO_4$, $Na_2MoO_4$, $Na_2W_2O_7$, $Na_4Mg(WO_4)_3$, $Li_2CO_3$, $Na_2CO_3$, $K_2CO_3$, NaBr, LiBr, KBr, LiI, NaI, KI, $Na_2W_4O_{13}$, $KFeO_2$, or any combination thereof.

Aspect 9. The oxygen-deficient mixed metal perovskite of any one of the preceding aspects, wherein x is from 0.125 to 0.875.

Aspect 10. The oxygen-deficient mixed metal perovskite of any one of the preceding aspects, wherein y is from 0.125 to 0.875.

Aspect 11. The oxygen-deficient mixed metal perovskite of any one of the preceding aspects, wherein y is 0.

Aspect 12. The oxygen-deficient mixed metal perovskite of any one of the preceding aspects, having a formula selected from the group consisting of $Sr_{0.875}Ba_{0.125}Fe_{0.5}Co_{0.5}O_{3-\delta}$, $Sr_{0.75}Ca_{0.25}Fe_{0.75}Mn_{0.25}O_{3-\delta}$, $Sr_{0.875}Ca_{0.125}Fe_{0.625}Mg_{0.375}O_{3-\delta}$, $Sr_{0.75}Ca_{0.25}CoO_{3-\delta}$, $Sr_{0.875}K_{0.125}CoO_{3-\delta}$, $Sr_{0.875}La_{0.125}Fe_{0.75}Cu_{0.25}O_{3-\delta}$, $Sr_{0.875}La_{0.125}Fe_{0.125}Co_{0.875}O_{3-\delta}$, $Sr_{0.75}Sm_{0.25}Fe_{0.125}Co_{0.875}O_{3-\delta}$, $Sr_{0.875}Y_{0.125}Fe_{0.75}Ni_{0.25}O_{3-\delta}$, $Sr_{0.625}Ca_{0.375}Fe_{0.75}Cu_{0.25}O_{3-\delta}$, $Sr_{0.875}Ba_{0.125}Fe_{0.375}Mn_{0.625}O_{3-\delta}$, $Sr_{0.75}Y_{0.25}Fe_{0.125}Co_{0.875}O_{3-\delta}$, $Sr_{0.875}K_{0.125}Fe_{0.75}Co_{0.125}Ni_{0.125}O_{3-\delta}$, $Sr_{0.5}Ba_{0.5}Fe_{0.625}Mg_{0.25}Ti_{0.125}O_{3-\delta}$, $SrFe_{0.5}Cu_{0.125}Mn_{0.125}Mg_{0.25}O_{3-\delta}$, $Sr_{0.875}Ca_{0.125}Fe_{0.75}Co_{0.125}Ni_{0.125}O_{3-\delta}$, $Sr_{0.875}La_{0.125}Fe_{0.75}Co_{0.125}Ni_{0.125}O_{3-\delta}$, $Sr_{0.875}Sm_{0.125}Fe_{0.75}Co_{0.125}Ni_{0.125}O_{3-\delta}$, $Sr_{0.5}Y_{0.5}Fe_{0.125}Ti_{0.875}O_{3-\delta}$, $Sr_{0.375}Y_{0.625}Fe_{0.5}Ti_{0.503-6}$, $Sr_{0.5}Y_{0.5}Fe_{0.375}Ti_{0.62503-6}$, $Sr_{0.375}Sm_{0.625}Fe_{0.375}Ti_{0.625}O_{3-\delta}$, $LaFe_{0.35}Mn_{0.65}O_{3-\delta}$, $YFe_{0.875}Co_{0.125}O_{3-\delta}$, $Sr_{0.125}Sm_{0.875}Fe_{0.75}Cu_{0.25}O_{3-\delta}$, $Sr_{0.375}La_{0.375}Sm_{0.25}Fe_{0.75}Ti_{0.25}O_{3-\delta}$, $Sr_{0.375}La_{0.5}Sm_{0.125}Fe_{0.75}Ti_{0.25}O_{3-\delta}$, and $Sr_{0.125}La_{0.625}Sm_{0.25}Fe_{0.875}Ti_{0.125}O_{3-\delta}$.

Aspect 13. A redox catalyst comprising the oxygen-deficient mixed metal perovskite of any one of the preceding aspects.

Aspect 14. A method for chemical looping air separation (CLAS), the method comprising:

(i) contacting a gas mixture comprising oxygen with the oxygen-deficient mixed metal perovskite of any one of aspects 1-12 or the redox catalyst of aspect 13, wherein the contacting creates a reduced level of oxygen deficiency in the perovskite; and (ii) exposing the perovskite having the reduced level of oxygen deficiency to a vacuum or steam purge to release concentrated oxygen while recreating the oxygen-deficient perovskite of (i).

Aspect 15. The method of aspect 14, wherein the gas mixture comprises an oxygen partial pressure of from about 0.01 atm to about 0.2 atm prior to performing the method.

Aspect 16. The method of aspect 14 or 15, wherein the gas mixture is substantially free of oxygen following performing the method.

Aspect 17. The method of any one of aspects 14-16, wherein the gas mixture comprises air.

Aspect 18. The method of any one of aspects 14-17, further comprising collecting oxygen separated from the gas mixture.

Aspect 19. A method for chemical looping (CL) $CO_2$ splitting, the method comprising contacting a gas mixture comprising carbon dioxide with the oxygen-deficient mixed metal perovskite of any of aspects 1-12 or the redox catalyst of aspect 13.

Aspect 20. The method of aspect 19, wherein at least 80% of the carbon dioxide is converted to carbon monoxide and oxygen.

Aspect 21. The method of aspect 19, wherein at least 85% of the carbon dioxide is converted to carbon monoxide and oxygen.

Aspect 22. A method for chemical looping methane conversion, the method comprising contacting a gas mixture comprising methane with the oxygen-deficient mixed metal perovskite of any of aspects 1-12 or the redox catalyst of aspect 13.

Aspect 23. The method of aspect 22, wherein at least 70% of the methane is converted to syngas.

Aspect 24. The method of aspect 22, wherein at least 80% of the methane is converted to syngas.

Aspect 25. A method for producing olefinic compounds using the oxygen-deficient mixed metal perovskite of any one of aspects 1-12 or the redox catalyst of aspect 13, comprising:

(i) contacting the oxygen-deficient mixed metal perovskite or the redox catalyst with one or more dehydrogenation reactants;

(ii) dehydrogenating the one or more dehydrogenation reactants to provide an olefinic compound and hydrogen and a reduced perovskite; and (iii) reoxidizing the reduced perovskite by introducing a gaseous oxidant comprising oxygen to the reduced perovskite to form a reoxidized perovskite; and (iv) re-using the reoxidized perovskite for a subsequent dehydrogenation and selective hydrogen combustion;

wherein at least 30% of the hydrogen released during step (ii) is converted using a lattice oxygen from the perovskite, resulting in formation of steam.

EXAMPLES

The following examples are put forth so as to provide those of ordinary skill in the art with a complete disclosure and description of how the compounds, compositions, articles, devices and/or methods claimed herein are made and evaluated, and are intended to be purely exemplary of the disclosure and are not intended to limit the scope of what the inventors regard as their disclosure. Efforts have been made to ensure accuracy with respect to numbers (e.g., amounts, temperature, etc.), but some errors and deviations should be accounted for. Unless indicated otherwise, parts are parts by weight, temperature is in ° C. or is at ambient temperature, and pressure is at or near atmospheric.

Example 1: Preliminary Screening Based on Structural Stability

The $Sr_xA_{1-x}Fe_yB_{1-y}O_3$ perovskite models were constructed by substituting A- and/or B-site cations in $SrFeO_3$, where A-site cations are typically consisted of alkaline earth, alkali or rare earth metals and B-site cations are usually transition metals. Table 1 summarizes the dopant types and concentrations investigated in this study. By exhausting all possible combinations of A- and/or B-site dopants in the selected cation network, 2401 perovskite models were constructed. Since some of these compositions may not form a stable perovskite phase, pre-screening steps were performed. Firstly, 168 compositions whose total valence cannot be zero were excluded, most of them contain large proportions (>50%) of Mg on the B-site.

TABLE 1

A-and B-site dopant elements, x, y, and δ in $Sr_xA_{1-x}Fe_yB_{1-y}O_{3-\delta}$ investigated

| | |
|---|---|
| A-site dopants | Ca, K, Y, Ba, La, Sm |
| B-site dopants | Co, Cu, Mn, Mg, Ni, Ti |
| x | 0, 0.125, 0.25, 0.375, 0.5, 0.625, 0.75, 0.875, 1 |
| y | 0, 0.125, 0.25, 0.375, 0.5, 0.625, 0.75, 0.875, 1 |
| δ | 0, 0.125, 0.25, 0.375, 0.5 |

Figure 3A:
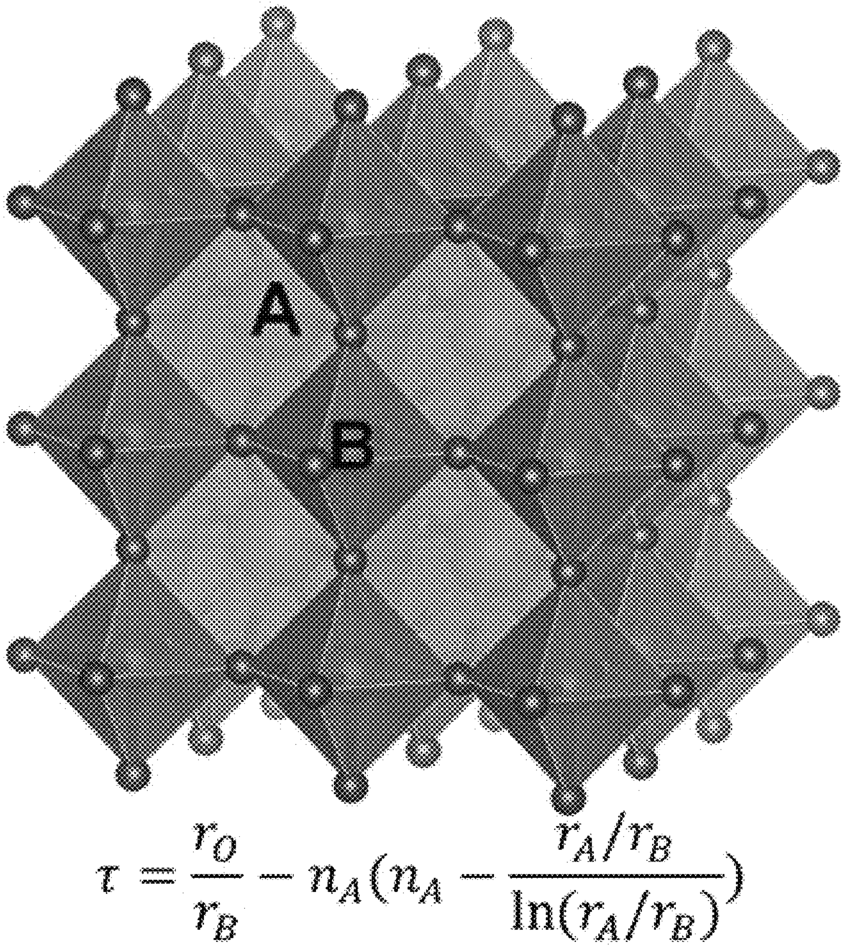
FIGS. 3A-3D show tolerance factor-based material screening.

Besides charge neutrality, the Goldschmidt tolerance factor $$\left(t = \frac{r_A + r_O}{\sqrt{2}(r_B + r_O)}\right)$$

is a frequently used empirical parameter to estimate the stabilities of perovskites. In a recent study, Bartel et al. proposed a modified tolerance factor $$\tau = \frac{r_O}{r_B} - n_A\left(n_A - \frac{r_A/r_B}{\ln(r_A/r_B)}\right),$$

where $r_0$, $r_A$, $r_B$ represent the radii of oxygen anion, and A- and B-site cations. $n_A$ and $n_B$ are the oxidation states of A- and B-site cations, respectively. The modified tolerance factor (i) carries more chemical information and exhibits better predictive ability than the classical Goldschmidt tolerance factor. Therefore, the modified tolerance factor, T, was applied to estimate the stabilities of the perovskite structures (FIG. 3A). Direct estimation of T in $Sr_xA_{1-x}Fe_yB_{1-y}O_{3-\delta}$ is challenging since the oxidation states and the ionic radii of Fe and other multi-valent B site cations are difficult to specify. To accommodate the $Sr_xA_{1-x}Fe_yB_{1-y}O_{3-\delta}$ system, T is expressed as a function of $\tau(n_A,n_B,x,y,\delta)$. For a given composition with a B-site element that has multiple oxidation states, all the parameters are fixed except for $n_B$, which should be between its lowest and highest oxidation states. Therefore, $\tau(n_A,n_B,x,y,\delta)$ should also be within a corresponding range. Since tolerance factor is used only as a preliminary screening step, a less stringent standard was adopted: a composition is considered to be feasible as long as its minimum $\tau(n_A,n_B,x,y,\delta)$ value is lower than a threshold value of 4.3, instead of 4.18 originally proposed by Bartel et al. This is value is used because there are stable perovskites whose Ts are slightly higher than 4.18, as suggested by the same authors.

Figure 3B:
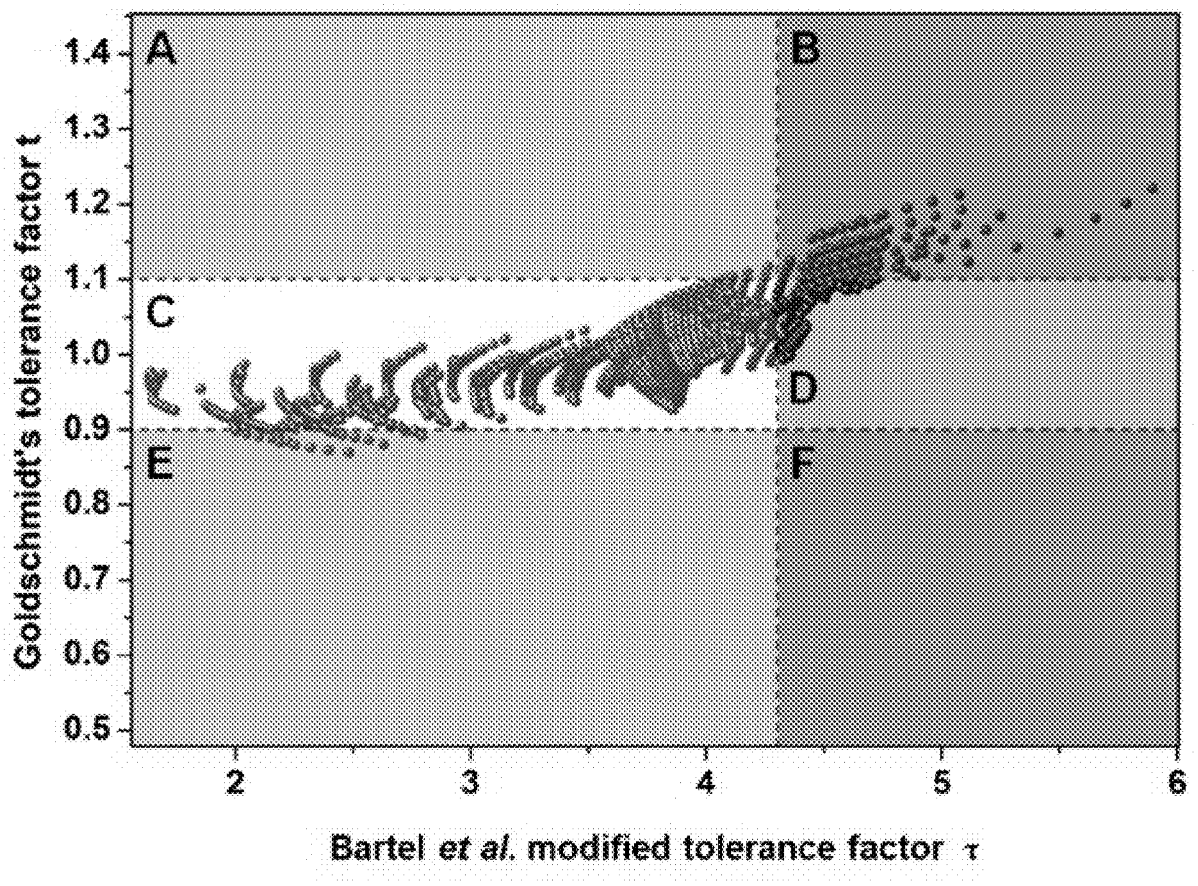
Figure 3C:
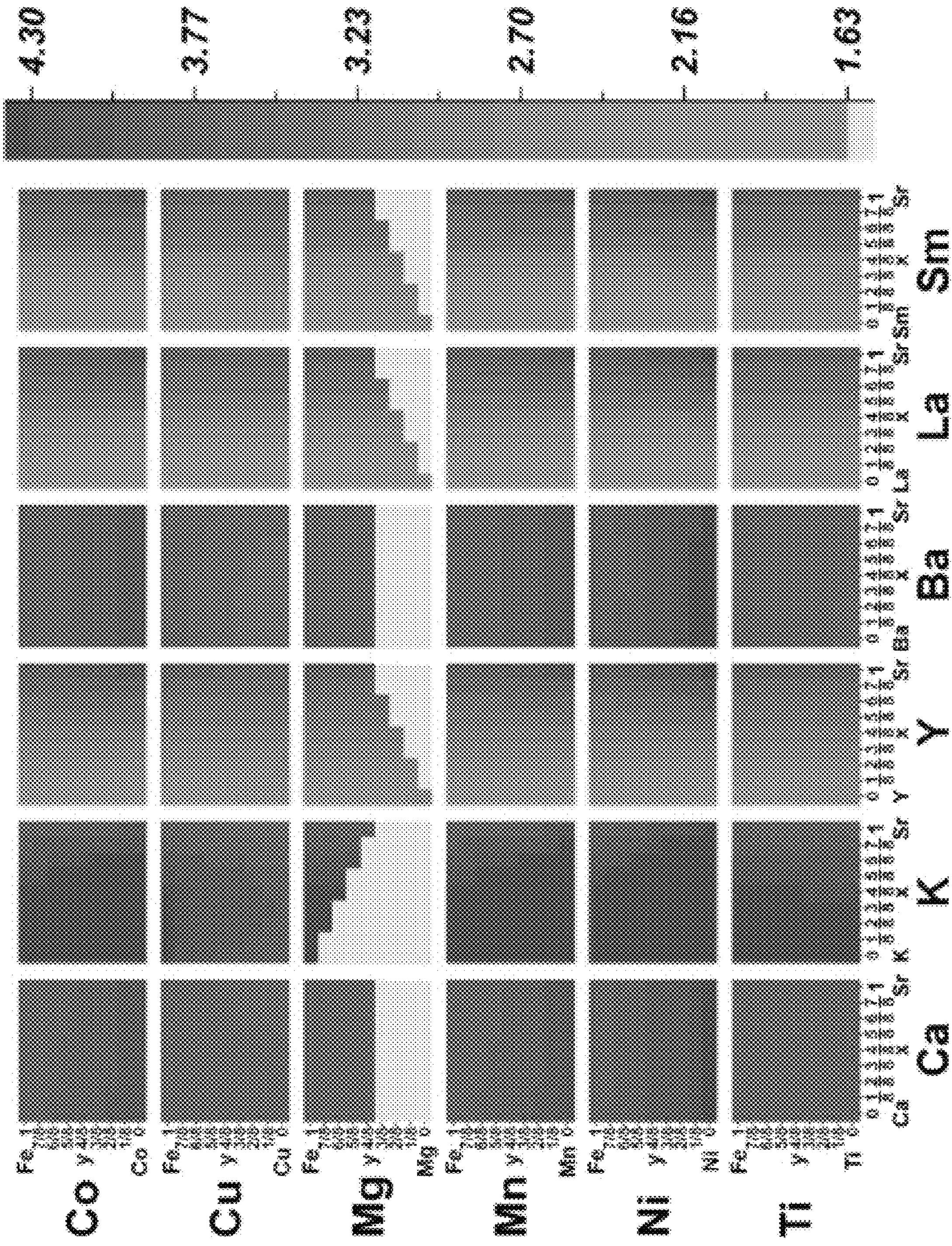
Figure 3D:
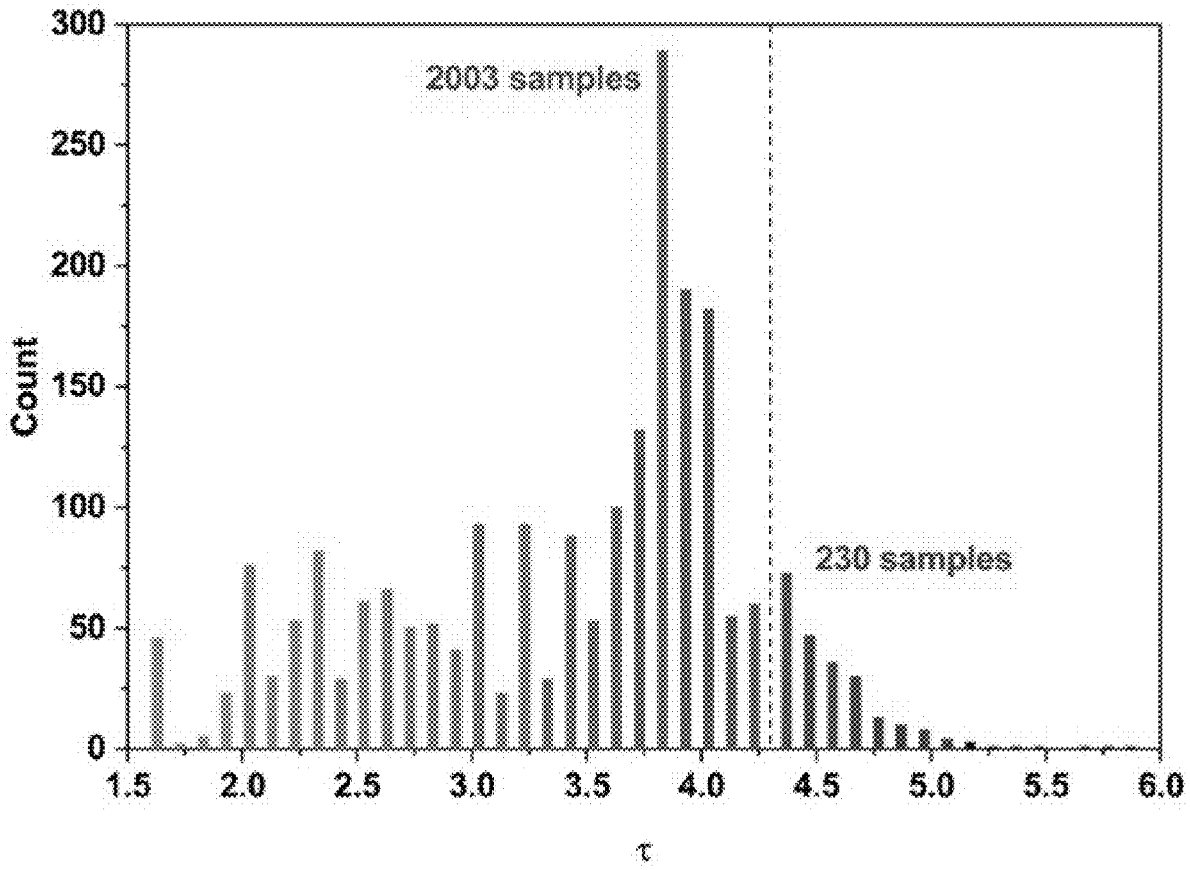

FIG. 3B illustrates the correlation between the Goldschmidt's tolerance factor (t) and the modified tolerance factor (T). Candidates in panels III and IV are considered as stable perovskites according to Goldschmidt's rule and candidates in panels I, III and V are suitable candidates according to the modified tolerance factor T. Although the predictions largely overlap with each other, a main disagreement is seen on panel IV, where the classical criterion indicates that these samples would be stable perovskites. It is noted that most candidates in panel IV contain >50% potassium at the A-sites, which tend to be unstable. This indicates that the modified tolerance factor is likely to be more accurate in predicting the stabilities of perovskites. Therefore, the modified tolerance factor was relied on for this pre-screening step. The candidates excluded either contain a large proportion of potassium at A-site (>50%) or a large proportion of Ni at B-site with A being Ca or Ba (FIG. 3C). Of all the candidates considered, 230 were screened out, leaving 2,003 candidates for high-throughput calculations (FIG. 3D).

Example 2: High Throughput Calculations of ΔG

Figure 4A:
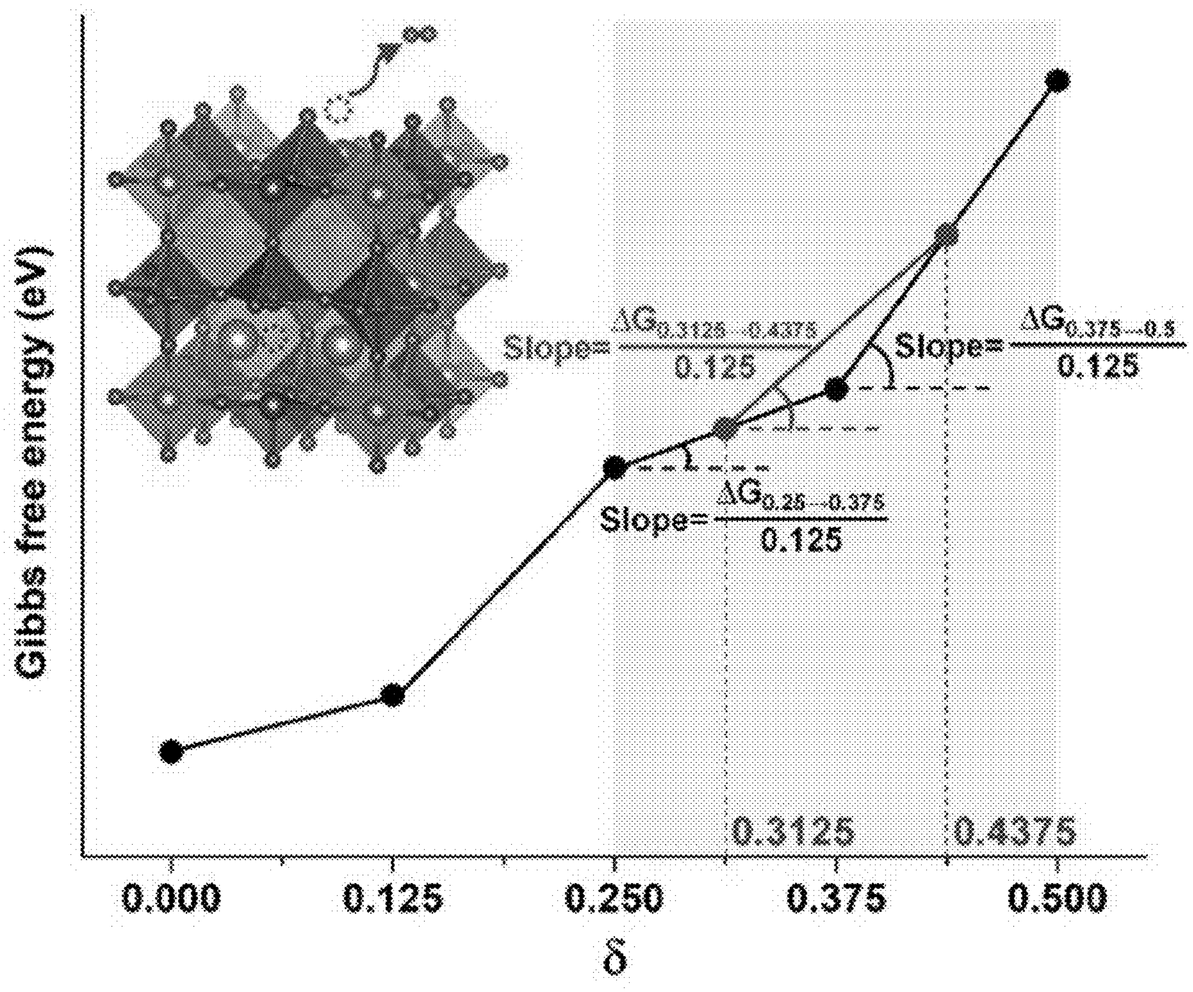
FIGS. 4A-4B show ΔGs for oxygen vacancy formation.

The redox properties of oxygen carriers play a key role in CL processes. However, it is challenging to precisely describe the redox properties of oxygen carriers with simple yet accurate theoretical indicators. Although there are some successful case-studies using the initial vacancy formation energy ($\Delta E_V$) of a perfect perovskite structure as a descriptor, the initial $\Delta E_V$ alone, in most cases, does not correlate well with the experimental observations due to the following reasons: i) the oxygen carriers rarely start from a defect-free state under practical experimental conditions; ii) both vacancy concentration and $\Delta E_V$ change with oxygen partial pressure or temperature swings; iii) $\Delta E_V$ does not account for entropy changes, which can be very important especially at high temperatures. To address these limitations, Gibbs free energy changes (ΔGs) within specified δ ranges were used as the descriptor for the redox properties. The ΔG(δ) can be directly compared to the experimental $P_{O2}$ and its effectiveness has been demonstrated in previous theoretical and experimental works. As illustrated in FIG. 4A, mixed oxide based oxygen carriers' redox thermodynamics can be described by their incremental Gibbs free energy. The slopes (simply written as ΔG) describe the $\mu_{O2}$ (or $P_{O2}$) within a vacancy concentration range (δs) at a given temperature. They can in turn be used to determine the feasibility and capacity of oxygen uptake and release within a given $P_{O2}$ and/or temperature swings. As one can anticipate, suitable ΔG over a large δ range would lead to a larger oxygen capacity. Previous experiments indicate that δ usually varies in the range of 0.25~0.5 in CL processes. It is also noted that every 0.125 change in δ correspond to roughly 1 wt % oxygen capacity. Therefore, the study focused on the ΔG within a δ range of 0.25 and 0.5 with 0.125 increment, i.e. $\Delta G_{0.25\rightarrow0.375}$ and $\Delta G_{0.375\rightarrow0.5}$. as well as their linear interpolation $\Delta G_{0.3125\rightarrow0.4375}$.

Using AGs as the descriptor, high-throughput DFT calculations were carried out on the 2,003 $Sr_xA_{1-x}Fe_yB_{1-y}O_{3-\delta}$ candidates. It is noted that many perovskite structures undergo a disorder-order transition of lattice oxygen during the process of oxygen release, forming a brownmillerite structure at large δs (a perovskite phase tends to be maintained at very high operating temperatures). Such phase transition will have different effects on the calculations of ΔG for different materials. To account for this, both the energies of perovskite and brownmillerite structures were calculated for all the candidates with δ=0.5 and the lower value was used to calculate the corresponding ΔGs at 400-700° C. For higher temperatures (800-950° C.), such transition was not considered since most of the materials should have disordered vacancies.

Figure 4B:
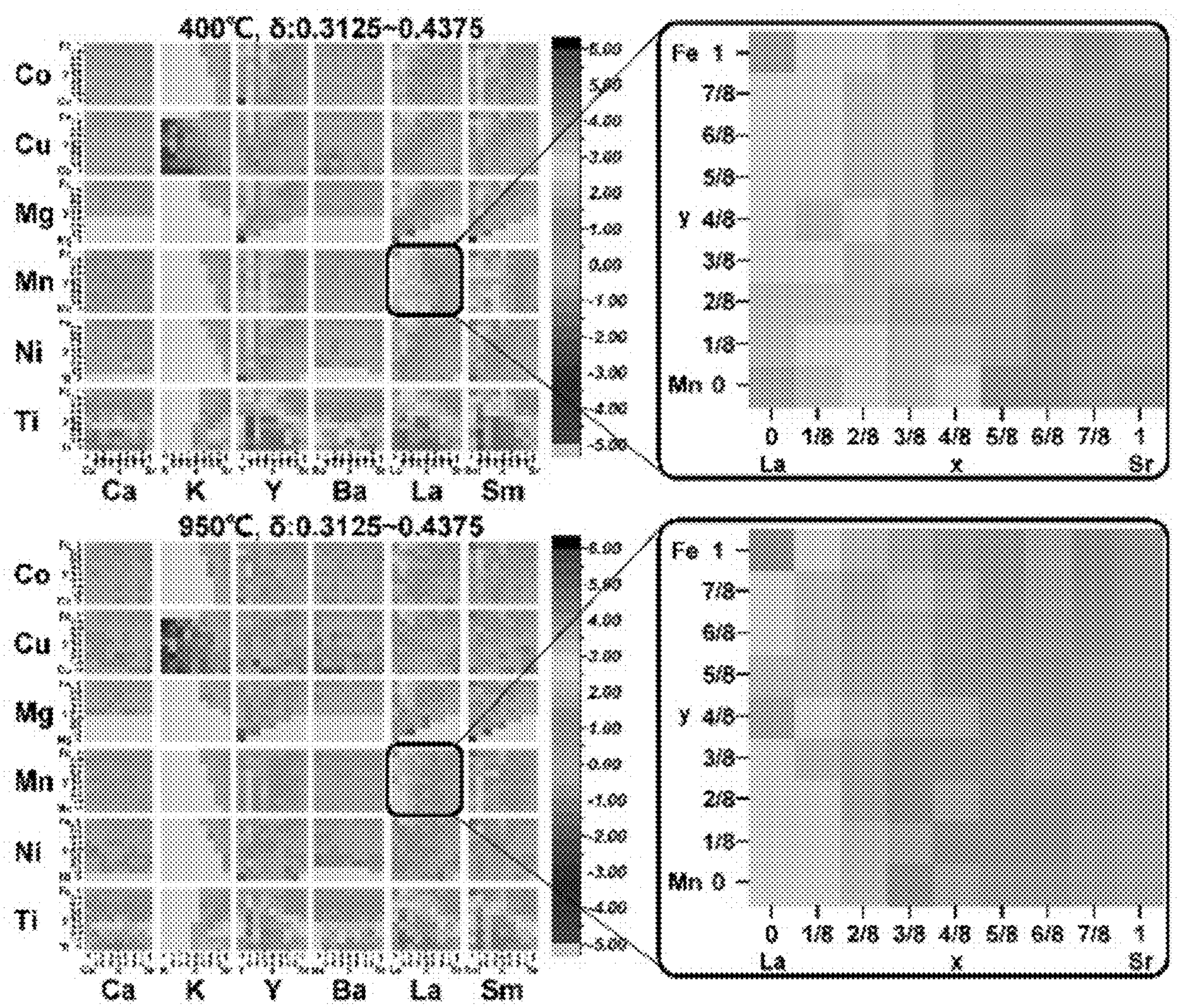

The computation results indicate that substitution of A- and/or B-site cation in $SrFeO_{3-\delta}$ can tune the redox ΔGs over very broad ranges (−6.15 eV~6.70 eV at 400° C. and −6.69 eV~6.14 eV at 950° C.). From the ΔG heatmap patterns, some general correlations between the dopant types, proportions and ΔGs can be captured. For instance, as exemplified by the $\Delta G_{0.3125 \rightarrow 0.4375}$ in FIG. 4B, the horizontal axis in each panel is the composition parameter x of Sr in $Sr_xA_{1-x}Fe_yB_{1-y}O_{3-\delta}$ and the vertical axis is the composition parameter y of Fe. It is clear that specific doping elements or combinations of co-doping elements can significantly affect the ΔG values. For instance, Ti-doping tends to increase the ΔGs, in some cases greater than 6 eV, while Cu-doping, especially Cu—K co-doping, significantly decreases the ΔGs. These findings can reduce the experimental trail-and-error for accelerated material discovery.

Example 3: ML Training and Prediction of Catalytic Performances

Figure 5A:
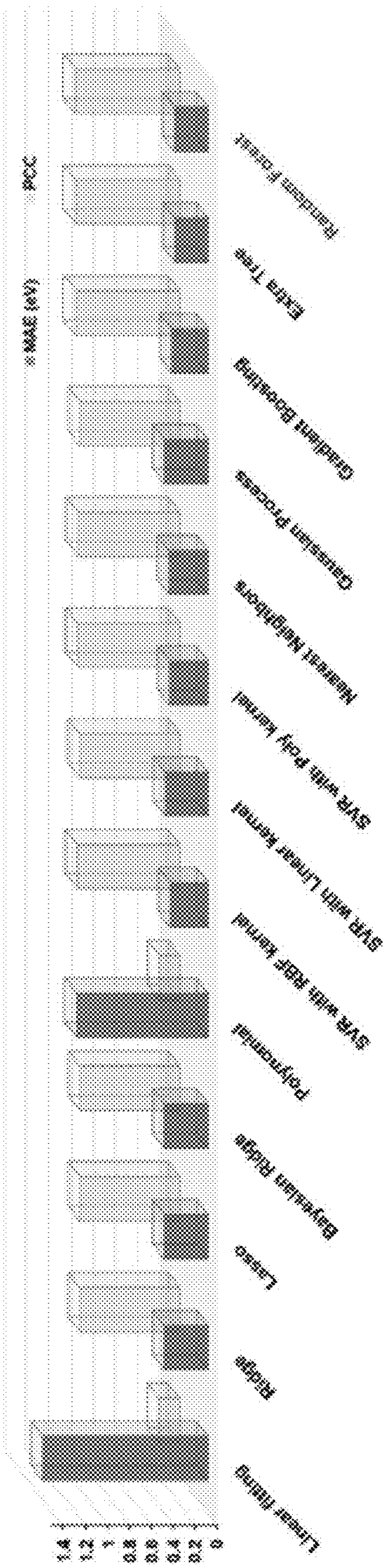
FIGS. 5A-5C show machine learning results.

The large datasets from high-throughput DFT allows us to perform further data analyses with ML to explore the correlations between the composition of perovskites and their ΔGs within the studied δ ranges. To select the appropriate ML model for these datasets, some test fittings were performed using a series of supervised learning algorithms. The studied algorithms include the family of linear models (linear fitting, and its regularized version Ridge and Lasso), support vector machines (SVM) with different kernel functions, nearest neighbors, Gaussian process, and the decision trees, etc. Here, the proportion of each cation element of the 2003 perovskites are used as the input features and their corresponding $\Delta G_{0.3125 \rightarrow 0.4375}$ at 400° C. as the target property. The performance of each learning algorithm with respect to the time-consumption, mean-absolute-error (MAE) and Pearson correlation coefficient (PCC) between the predicted and DFT computed values were presented in FIG. 5A. Results show that the time-consumption in the training step of all the considered algorithms are negligible, with the slowest one (gaussian process) takes only ~1 s to complete. The accuracies of the linear and polynomial regression algorithms are much lower than other algorithms, indicating that the underlying relationships between compositions and ΔGs, like many other quantum chemical problems, are non-linear and cannot be accurately described with linear or polynomial functions. The advantage of most no-linear algorithms is that they mainly contain multiple hyperparameters, i.e. internal model parameters, which can be optimized to adapt to different systems. This allows them to perform well in the current datasets. Especially the random forest (RF), an ensemble learning algorithm based on a multitude of trainable decision trees, has shown superior prediction performances than many other non-linear algorithms like kernel-based ones in handling complex chemical and material problems. As can be seen in FIG. 5A, RF exhibits the best predictive performance (highest PCC and lowest MAE) for the test datasets. It was therefore selected for subsequent training and predictions.

Figure 5B:
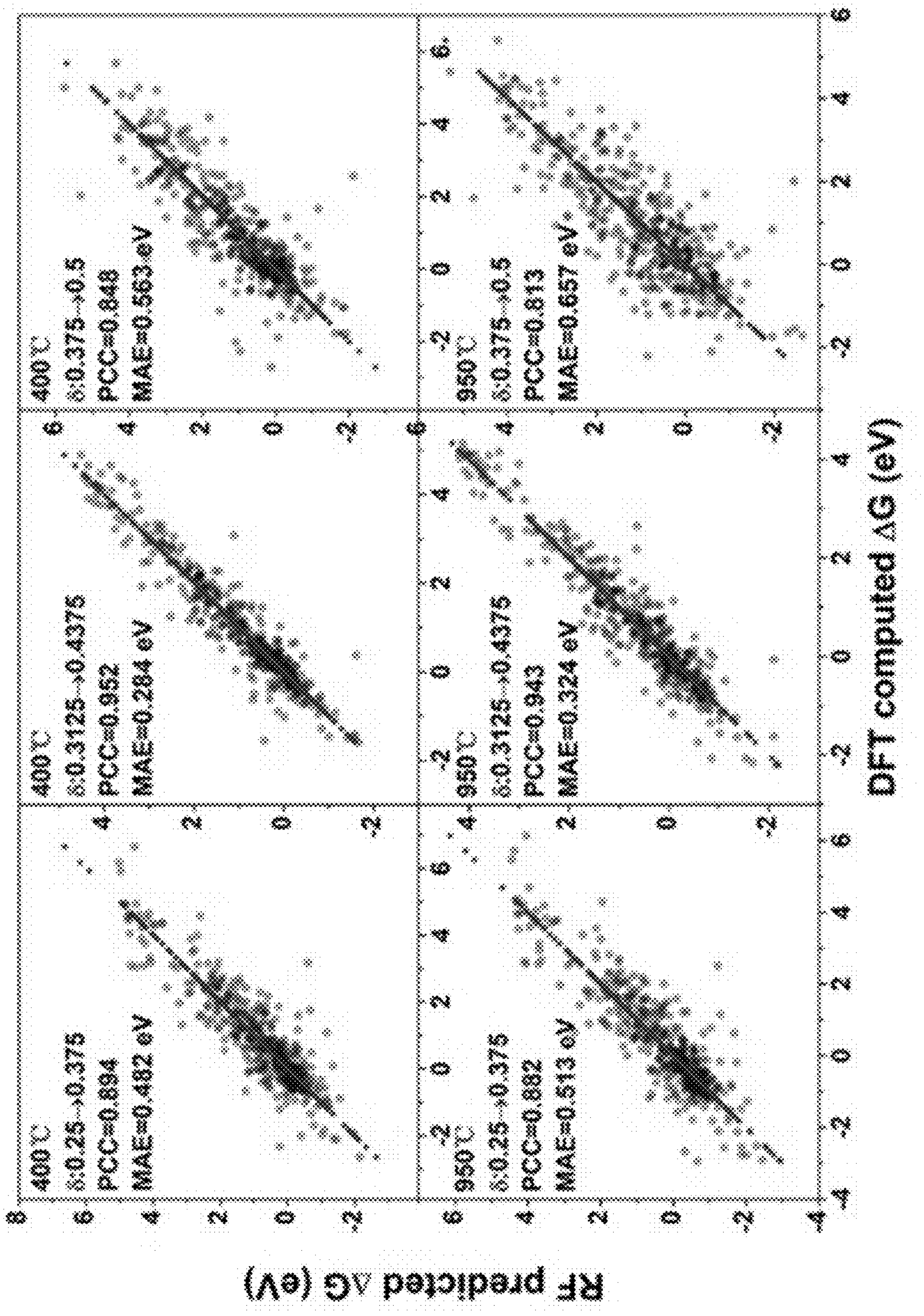

FIG. 5B summarizes the performance of RF on the test datasets in the model evaluation step. As can be seen, RF provides reasonable prediction accuracy for all the ΔGs considered with high PCC (0.813-0.952) and low MAE (0.284-0.657 eV). This is especially the case for $\Delta G_{0.3125 \rightarrow 0.4375}$ at both low (400° C.) and high (950° C.) temperatures, with high PCCs (0.952 and 0.943) and low MAEs (0.284 and 0.324 eV). Such errors are comparable with many DFT errors for perovskites calculations, showing the RF model's potential. In addition, an attempt was made to improve the RF model using additional $\mu_{O2}$-related properties, such as the average charge (Δe) and p-band center ($\varepsilon_p$) of oxygen anions, as the input features in the model training step. However, the introduction of these electronic descriptors did not result in notable improvement of the predictive performances of the RF model. Considering the substantial CPU-time required for the calculations of these descriptors, it was decided to not use them in the subsequent predictions.

Figure 5C:
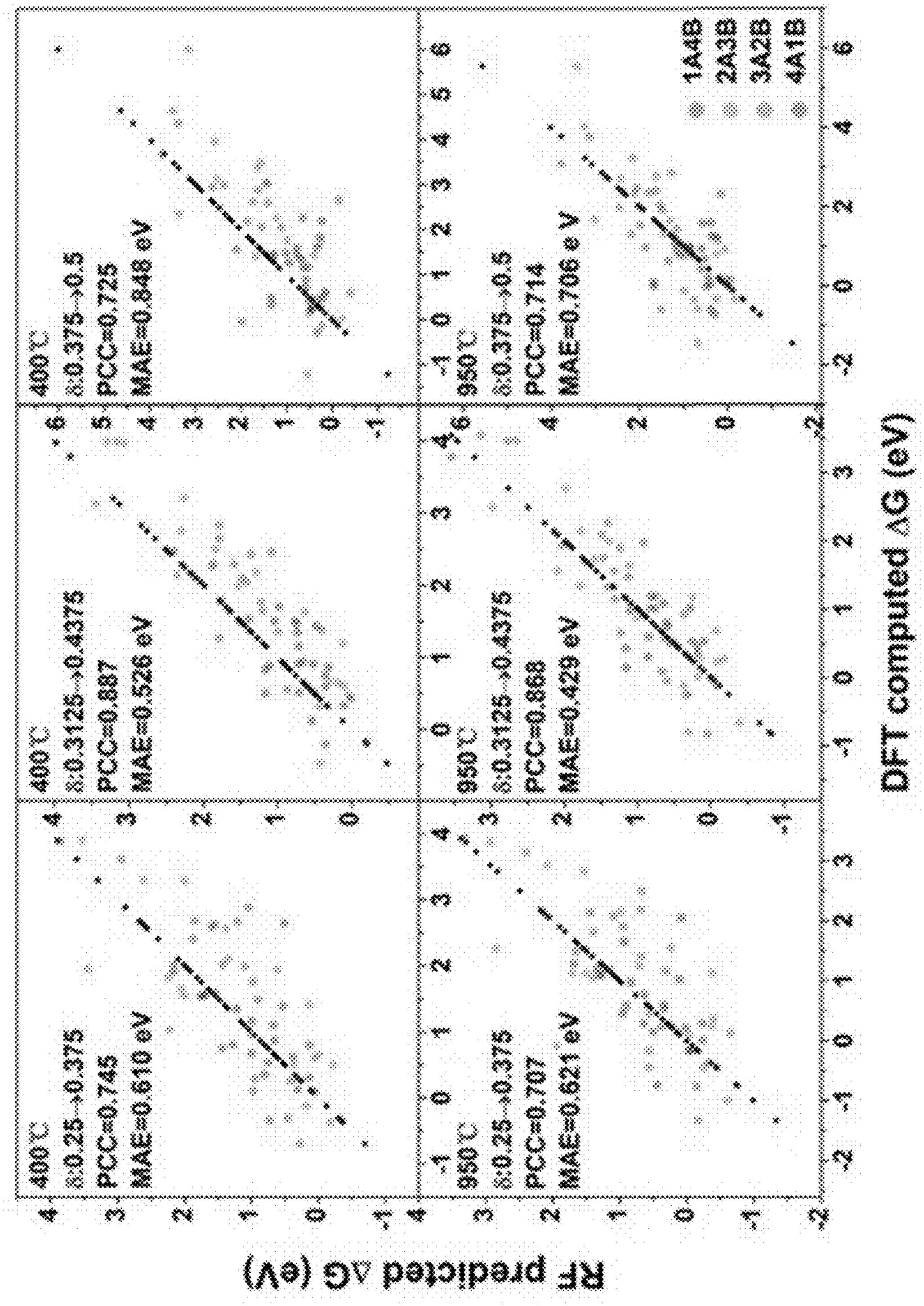

Since the DFT calculation has already exhausted all the perovskites containing 2, 3, and 4 cation elements, the RF based ML model was further extended to predict the properties of perovskites containing 5 cation elements, also known as high-entropy perovskites. 227,273 perovskite compositions, prescreened out of 264,110 compositions based on the Goldschmidt's tolerance factor, were calculated. The modified tolerance factor was not used due to the high complexity of the 5 cation elements perovskites. To examine the reliability and accuracy of these predictions, 60 samples were randomly selected for further DFT calculations and compared the results with the predicted values as shown in FIG. 5C. The results confirm satisfactory correlations especially for the predictions of $\Delta G_{0.3125 \rightarrow 0.4375}$ with PCC=0.887 and 0.868, and MAE=0.526 and 0.429 eV at 400° C. and 950° C., respectively. Such prediction accuracy is acceptable especially when applied to screen CL materials with large chemical potential spans such as CL $CO_2$ splitting. Combined with its efficiency (6 orders of magnitude faster than DFT calculations to produce a set of target ΔGs), ML can be a powerful tool for accelerated material discovery and design. However, further extension of the RF model to predict the property of more complex perovskites, such as the ones containing 6 or more cation elements, becomes unreliable. This is probably because the chemical information contained in the current RF model is insufficient to predict the very complicated couplings of spin and electronic states in systems containing 6 or more cation elements.

Example 4: Applications for Chemical Looping Air Separation and $CO_2$ Splitting The applicability and effectiveness of DFT and ML based high throughput screening are experimentally investigated in the context of chemical looping air separation (CLAS) and CL based $CO_2$ splitting. These two specific applications were selected since they represent two extreme chemical looping cases in terms of $P_{O2}$ and operating temperature, as illustrated in FIG. 1B and Table 2 below. Covering the two extreme cases, with a 550° C. temperature span and 20 orders of magnitudes for $P_{O2}$, would help to demonstrate the general applicability of the computational results.

TABLE 2

| Experimental parameters and screening criteria of CLAS and CL $CO_2$ splitting | | |
|---|---|---|
| Application | CLAS | CL $CO_2$ Splitting |
| Reduction Rxn. | Air $\leftrightarrows N_2$ | $CO + \frac{1}{2} O_2 \leftrightarrows CO_2$ |
| Oxidation Rxn. | $Sr_xA_{1-x}Fe_yB_{1-y}O_{3-\delta 1} \leftrightarrows (\delta_2-\delta_1)/2\ O_2 + Sr_xA_{1-x}Fe_yB_{1-y}O_{3-\delta 2}$ | $CH_4 + \frac{1}{2} O_2 \leftrightarrows CO + 2H_2$ |
| $P_{O2}$ range | ~0.01-0.2 atm | ~$10^{-21}$-$10^{-17}$ atm |
| Temp. range | 400-900° C. (preferably <600° C.) | 750-1,000° C. |
| Ideal ΔG ranges | 0.05-0.13 eV at 400° C. | 2.23-2.24 eV at 400° C. |
| | 0.07-0.19 eV at 700° C. | 2.13-2.41 eV at 700° C. |
| ΔG screening | −0.25-0.63 eV at 400° C. | 1.93-2.74 eV at 400° C. |
| criteria | −0.23-0.69 eV at 700° C. | 1.83-2.91 eV at 700° C. |

CLAS operates within very narrow $P_{O2}$ swings since the thermodynamic driving force for separating $O_2$ from air is intrinsically limited. The target range of ΔG per O atom can be calculated from the $P_{O2}$ (or $\mu_{O2}$) swing:

$$\Delta G_{exp} = -\frac{1}{2} RT \ \ln\frac{P_{O_2}}{P^0}$$

where R is the ideal gas constant and $P^0$ is the standard atmospheric pressure. A $P_{O2}$ swing between 0.01 and 0.2 atm is typical when considering both the oxygen release and regeneration requirements. This corresponds to very small ΔG ranges of 0.05-0.13 eV at 400° C., and 0.07-0.19 eV at 700° C. The narrow ranges are challenging for DFT due to its relatively large errors when calculating redox thermodynamics of perovskites (up to 0.98 eV) according to previous reports, let alone the ML predictions which would have even larger errors. The errors from the DFT calculations in the current study are relatively small (0.05~0.70 eV) based on a comparison between the calculated results of 9 samples with those reported in experimental literatures. The higher accuracy compared to previous DFT studies may have resulted from (1) the δ ranges investigated are closer to the experimental ranges; (2) the model created was based on an advanced sampling method (MCSQS), allowing the model to better represent a randomly distributed solid solution; (3) more accurate thermodynamic analyses implemented by phonopy were applied to estimate the enthalpy and entropy contributions.

Given that the goal of the high throughput calculation is to screen out promising materials, target ΔG ranges are relaxed to account for the uncertainty in DFT results. It is noted that DFT tends to overestimate the ΔG, the upper limit of $\Delta G_{exp}$ were modified empirically by adding 0.5 eV while extending the lower limit by 0.3 eV. As such, the target ΔG ranges are modified to $$\Delta G_{Target}\begin{cases} \in [-0.25, 0.63] \text{ eV at } 400^\circ \text{ C.} \\ \in [-0.23, 0.69] \text{ eV at } 700^\circ \text{ C.} \end{cases}.$$

Figure 6A:
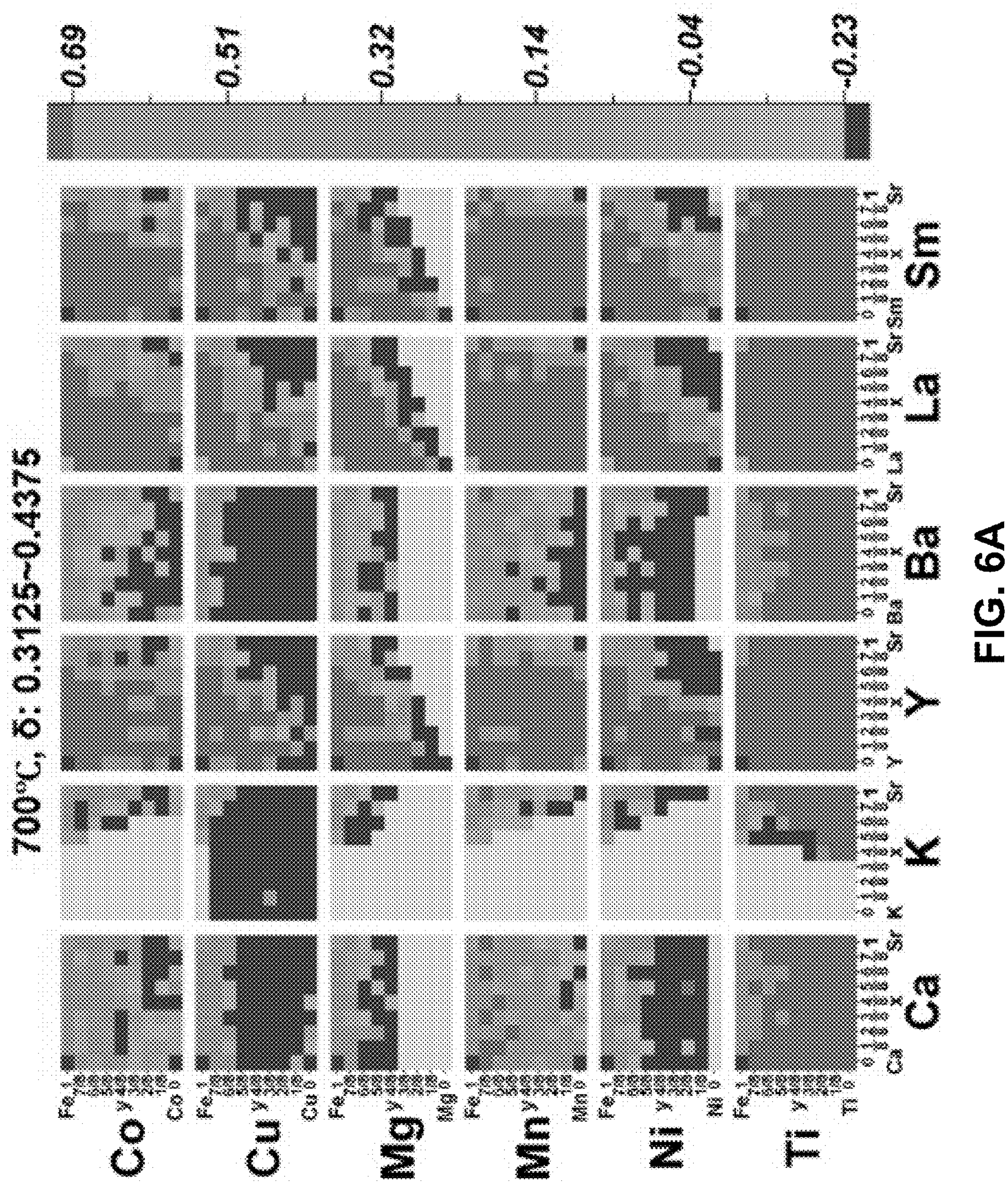
FIGS. 6A-6D show high throughput screening results and experimental validations.

Using these target ranges, the promising materials were screened as shown in FIG. 6A, in which the blue and red colors represent the samples whose ΔGs are higher or lower than the target region, respectively. An additional 1,270 candidates whose ΔGs are within the target range at either temperature. These materials have the potential for CLAS either at 400 or 700° C. When applying a tighter criterion requiring satisfactory ΔGs at both 400 and 700° C. covering the entire δ range of 0.25-0.5, 113 promising CLAS candidates were further screened out. Using the same target ΔG ranges, 17047 samples with 5 cation elements were predicted by ML.

Figure 6B:
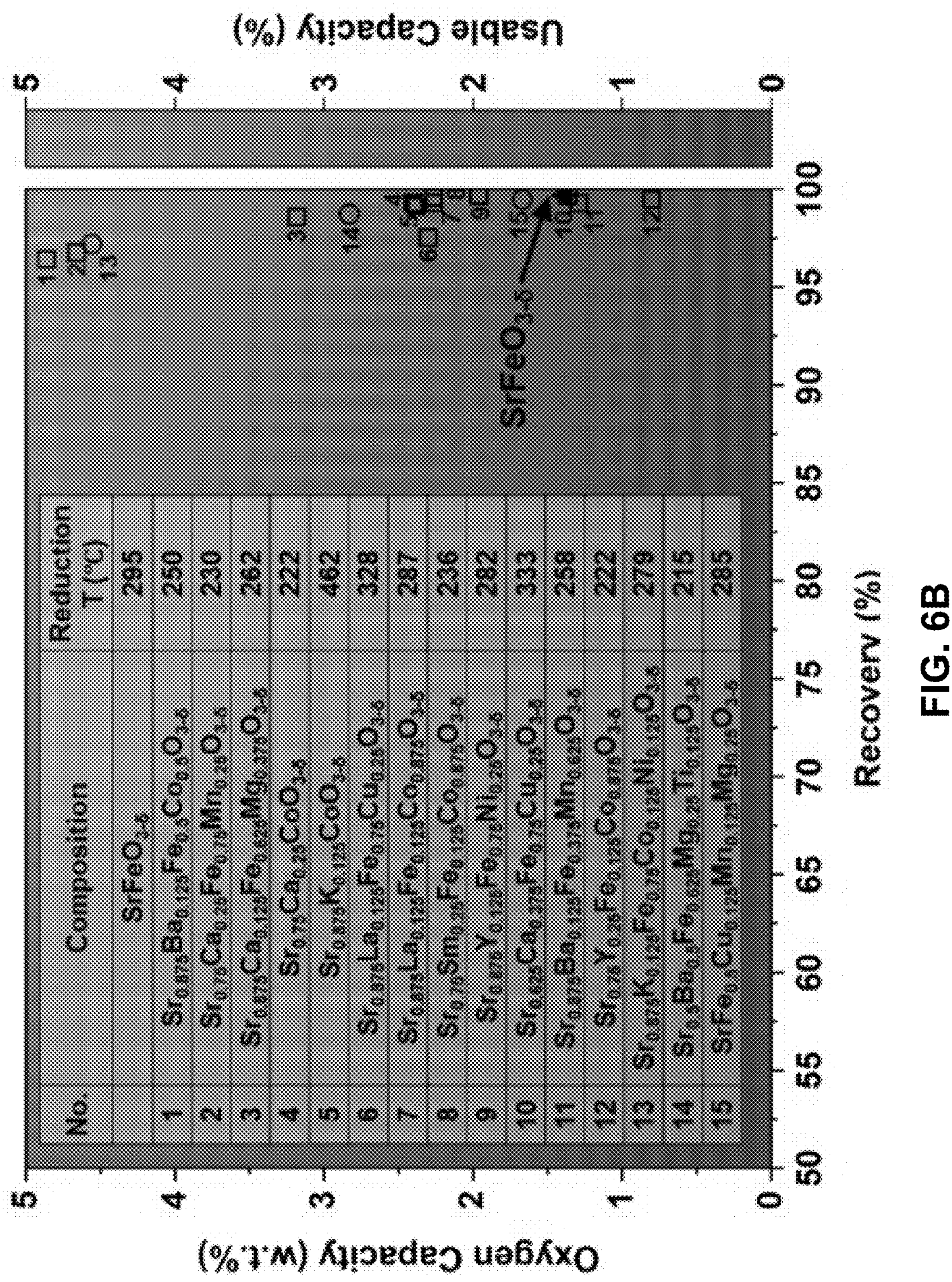

Of the 113 CLAS materials predicted by DFT, 36 with very similar compositions have been confirmed by 12 experimental systems and showed excellent results. Of the 77 DFT predicted materials that have not been reported previously, 12 materials were selected for experimental validation. 3 ML predicted materials were also experimentally investigated. These experimental findings, both from literature and the current experimental study, are summarized in Table 3. Given that experimental procedures in literatures tend to vary, FIG. 6B only summarized the performance of the 15 samples tested in the present study using an identical testing procedure. Table 3 summarizes the performance details of the 36 literature reported materials as well as the 15 samples tested in this study. As can be seen, a large fraction of the DFT predicted materials demonstrated satisfactory CLAS performance: 13 out of the 15 samples experimentally tested in this work exhibited better performance than the baseline $SrFeO_3$ oxygen carrier in at least one of the performance metric; 10 samples are far superior (>50% increase in capacity vs. $SrFeO_3$). In addition, 5 of the 15 materials tested demonstrated better performance than most, if not all, the previously reported materials. Interestingly, some of the compositions, such as $Sr_{0.875}Ca_{0.125}Fe_{0.625}Mg_eO_{3-\delta}$ and $Sr_{0.875}K_{0.125}Fe_{0.75}Co_{0.125}Ni_{0.125}O_{3-\delta}$, are quite atypical when compared to the compositions reported in literature. Investigation of these unique compositions would have been extremely unlikely if heuristic-based or trial and error approaches are adopted. This clearly demonstrates the effectiveness of the high throughput approach in this study. While it is not within the scope of this study to extensively test the ML predicted materials, these experimental results do indicate that ML can also provide valuable guidance on the design of complex mixed oxides. Experimental XRD patterns of the 15 samples indicate that their main phases are perovskites with some samples contain minor phase impurities. It is also noted that the poor-performance by $Sr_{0.875}Ba_{0.125}Fe_{0.375}Mn_{0.625}O_{3-\delta}$ is probably caused by phase segregation, with notable SrO and BaO phases. This is likely to be due the hygroscopic nature of the Mn nitrate precursor, leading to lower amounts of Mn being incorporated into the perovskite. This issue occurred for all materials with Mn on the B site, including $SrFe_{0.5}Co_{0.125}Mn_{0.125}Mg_{0.25}O_{3-\delta}$ and $Sr_{0.75}Ca_{0.25}Fe_{0.75}Mn_{0.25}O_{3-\delta}$. The Ti containing phase suffered from a similar issue, as the Ti Butoxide precursor, a viscous liquid, tends to aggregate along the walls of the transfer vessel. $Sr_{0.625}Ca_{0.375}Fe_{0.76}Cu_{0.26}O_{3-\delta}$ also suffers from phase segregation, with CuO and CaO both presenting in the XRD spectra. Segregation of CuO from perovskite was commonly encountered in previous literature. It is also noted that many of these compositions, although appear to be complex, can be prepared by relative simple methods such as solid-state reaction due to their thermodynamic stability.

Experimental performance of the DFT/ML predicted materials for CLAS

| $Sr_{1-x}A_xFe_{1-y}B_yO_3$ | Tested Composition | Model Predicted Composition | Temperature | Environment | Key Results* |
|---|---|---|---|---|---|
| $SrFeO_3$ | Base Material | N/A | 100° C.-1000° C. | 50% $O_2$ | 1.38%, R = 99.9%, TR = 297° C. |
| A = Ca | $Sr_{0.75}Ca_{0.24}FeO_{3-\delta}$ | $Sr_{0.875}Ca_{0.125}FeO_{3-\delta}$ | 600° C. | 5%-20% $O_2$ | 1.2% |
| A = K | $Sr_{0.9}K_{0.1}FeO_{3-\delta}$ | $Sr_{0.875}K_{0.125}FeO_{3-\delta}$, $Sr_{0.625}K_{0.375}FeO_{3-\delta}$ | 700° C. | 1%-20% $O_2$ | 1.35% |
| B = Co | $SrFe_{0.75}Co_{0.25}O_{3-\delta}$ | $SrFe_{0.625}Co_{0.375}O_{3-\delta}$, $SrFe_{0.375}Co_{0.625}O_{3-\delta}$ | — | — | Vacancy Formation Energy of 0.5 eV |
| B = Cu | $SrFe_{0.85}Cu_{0.15}O_{3-\delta}$ | $SrFe_{0.75}Cu_{0.25}O_{3-\delta}$ | 350° C.-1000° C. | 90%-0.01% $O_2$ | ~2.9%, Δδ = 0.35 |
| B = Mn | $SrFe_{0.8}Mn_{0.1}O_{3-\delta}$ | $SrFe_{0.825}Mn_{0.375}O_{3-\delta}$, $SrFe_{0.5}Mn_{0.5}O_{3-\delta}$, $SrFe_{0.375}Mn_{0.625}O_{3-\delta}$, $SrFe_{0.25}Mn_{0.75}O_{3-\delta}$ | 700° C. | 1%-20% $O_2$ | 1.33%. $E_a$ = 45 kJ/mol |
| A = Ba; B = Co | $Sr_{0.9}Ba_{0.1}Fe_{0.5}Co_{0.2}O_{3-\delta}$, $Sr_{0.7}Ba_{0.3}Fe_{0.5}Co_{0.2}O_{3-\delta}$, $Sr_{0.5}Ba_{0.5}Fe_{0.5}Co_{0.2}O_{3-\delta}$ | $Sr_{0.125}Ba_{0.575}Fe_{0.375}Co_{0.625}O_{3-\delta}$, $Sr_{0.25}Ba_{0.75}Fe_{0.825}Co_{0.375}O_{3-\delta}$, $Sr_{0.5}Ba_{0.5}Fe_{0.5}Co_{0.5}O_{3-\delta}$, $Sr_{0.75}Ba_{0.25}Fe_{0.8}Co_{0.5}O_{3-\delta}$, $Sr_{0.875}Ba_{0.125}Fe_{0.375}Co_{0.625}O_{3-\delta}$, $Sr_{0.75}Ba_{0.25}Fe_{0.75}Co_{0.25}O_{3-\delta}$, $Sr_{0.875}Ba_{0.125}Fe_{0.5}Co_{0.5}O_{3-\delta}$ | 500K-1300K | $N_2$ | Δδ = 0.25, ~1.7 wt % |
| A = Ca; B = Co | $Sr_{0.8}Ca_{0.2}Fe_{0.4}Co_{0.6}O_{3-\delta}$ | $Sr_{0.75}Ca_{0.25}CoO_{3-\delta}$, $Sr_{0.125}Ca_{0.875}Fe_{0.25}Co_{0.75}O_{3-\delta}$, $Sr_{0.375}Ca_{0.625}Fe_{0.125}Ca_{0.875}O_{3-\delta}$, $Sr_{0.625}Co_{0.375}Fe_{0.75}Co_{0.25}O_{3-\delta}$, $Sr_{0.75}Ca_{0.25}Fe_{0.375}Co_{0.625}O_{3-\delta}$, $Sr_{0.75}Ca_{0.25}Fe_{0.5}Co_{0.5}O_{3-\delta}$, $Sr_{0.825}Ca_{0.125}Fe_{0.375}Co_{0.625}O_{3-\delta}$, $Sr_{0.825}Ca_{0.125}Fe_{0.625}Co_{0.375}O_{3-\delta}$, $Sr_{0.825}Ca_{0.125}Fe_{0.75}Co_{0.25}O_{3-\delta}$ | 400° C. | 5%-20% $O_2$ | 1.2 wt %, 95% purity |
| A = Ca; B = Mn | $Sr_{0.2}Ca_{0.8}MnO_{3-\delta}$ | $Sr_{0.375}Ca_{0.625}Fe_{0.625}Mn_{0.375}O_{3-\delta}$, $Sr_{0.625}Ca_{0.375}Fe_{0.25}Mn_{0.75}O_{3-\delta}$, $Sr_{0.625}Ca_{0.375}Fe_{0.75}Mn_{0.25}O_{3-\delta}$, $Sr_{0.75}Ca_{0.825}Fe_{0.25}Mn_{0.75}O_{3-\delta}$, $Sr_{0.75}Ca_{0.25}Fe_{0.75}Mn_{0.25}O_{3-\delta}$, $Sr_{0.875}Ca_{0.125}Fe_{0.25}Mn_{0.75}O_{3-\delta}$, $Sr_{0.875}Ca_{0.125}Fe_{0.375}Mn_{0.625}O_{3-\delta}$ | 1200° C.-400° C. | Ar | 2.25% |
| A = La; B = Co | $Sr_{0.9}La_{0.1}Fe_{0.1}Co_{0.5}O_{3-\delta}$, $Sr_{0.9}La_{0.1}Fe_{0.5}Co_{0.5}O_{3-\delta}$ | $Sr_{0.675}La_{0.125}Fe_{0.125}Co_{0.875}O_{3-\delta}$, $Sr_{0.875}La_{0.125}Fe_{0.25}Co_{0.75}O_{3-\delta}$, $Sr_{0.675}La_{0.125}Fe_{0.5}Co_{0.5}O_{3-\delta}$ | 25° C.-800° C. | He | 2.5%, fast kinetics, cycle stability |
| A = Ba; B = Co | This Study (see next column) | $Sr_{0.875}Ba_{0.125}Fe_{0.5}Co_{0.5}O_{3-\delta}$ | 100° C.-1000° C. | 50% $O_2$ | 4.86%, R = 96.7%, TR = 250° C. |
| A = Ca; B = Mn | This Study | $Sr_{0.75}Ca_{0.25}Fe_{0.75}Mn_{0.25}O_{3-\delta}$ | 100° C.-1000° C. | 50% $O_2$ | 4.66%, R = 97%, TR = 230° C. |
| A = Ca; B = Mg | This Study | $Sr_{0.875}Ca_{0.125}Fe_{0.825}Mg_{0.375}O_{3-\delta}$ | 100° C.-1000° C. | 50% $O_2$ | 3.18%, R = 98.9% TR = 262° C. |
| A = Ca; B = Co | This Study | $Sr_{0.875}K_{0.125}CoO_{3-\delta}$ | 100° C.-1000° C. | 50% $O_2$ | 2.4%, R = 99.6%. TR = 222° C. |
| A = K; B = Co | This Study | $Sr_{0.875}K_{0.125}CoO_{3-\delta}$ | 100° C.-1000° C. | 50% $O_2$ | 2.38%, R = 99% TR = 262° C. |
| A = La; B = Cu | This Study | $Sr_{0.875}La_{0.125}Fe_{0.75}Cu_{0.25}O_{3-\delta}$ | 100° C.-1000° C. | 50% $O_2$ | 2.3%, R = 97.8%. TR = 328° C. |
| A = La; B = Co | This Study | $Sr_{0.875}La_{0.125}Fe_{0.125}Co_{0.875}O_{3-\delta}$ | 100° C.-1000° C. | 50% $O_2$ | 2.26%, R = 99.9% TR = 287° C. |

-continued

Experimental performance of the DFT/ML predicted materials for CLAS

| $Sr_{1-x}A_xFe_{1-y}B_yO_3$ | Tested Composition | Model Predicted Composition | Temperature | Environment | Key Results* |
|---|---|---|---|---|---|
| A = Sm;<br>B = Co | This Study | $Sr_{0.75}Sm_{0.25}Fe_{0.125}Co_{0.875}O_{3-\delta}$ | 100° C.-1000° C. | 50% $O_2$ | 2.26%,<br>R = 99.6%,<br>TR = 236° C. |
| A = Y;<br>B = Ni | This Study | $Sr_{0.875}Y_{0.125}Fe_{0.75}Ni_{0.25}O_{3-\delta}$ | 100° C.-1000° C. | 50% $O_2$ | 1.96%,<br>R = 100%,<br>TR = 282° C. |
| A = Ca;<br>B = Cu | This Study | $Sr_{0.825}Ca_{0.375}Fe_{0.75}Mn_{0.25}O_{3-\delta}$ | 100° C.-1000° C. | 50% $O_2$ | 1.36%,<br>R = 100%<br>TR = 333° C. |
| A = Ba;<br>B = Mn | This Study | $Sr_{0.875}B_{0.125}Fe_{0.375}Mn_{0.825}O_{3-\delta}$ | 100° C.-1000° C. | 50% $O_2$ | 1.29%,<br>R = 99.6,<br>TR = 258° C. |
| A = Y;<br>B = Co | This Study | $Sr_{0.75}Y_{0.25}Fe_{0.125}Co_{0.875}O_{3-\delta}$ | 100° C.-1000° C. | 50% $O_2$ | 0.80%,<br>R = 99.8%,<br>TR = 222 ° C. |
| A = K;<br>$B_1$ = Co,<br>$B_2$ = Ni | This Study (ML) | $Sr_{0.875}K_{0.125}Fe_{0.75}Co_{0.125}Ni_{0.125}O_{3-\delta}$ | 100° C.-1000° C. | 50% $O_2$ | 4.56%,<br>R = 97.5%,<br>TR = 279° C. |
| A = Ba;<br>$B_1$ = Mg,<br>$B_2$ = Ti | This Study (ML) | $Sr_{0.5}Ba_{0.5}Fe_{0.625}Mg_{0.25}Ti_{0.125}O_{3-\delta}$ | 100° C.-1000° C. | 50% $O_2$ | 2.83%,<br>R = 99%,<br>TR = 215° C. |
| $B_1$ = Cu,<br>$B_2$ = Mn,<br>$B_3$ = Mg | This Study (ML) | $SrFe_{0.5}Cu_{0.325}Mn_{0.125}Mg_{0.25}O_{3-\delta}$ | 100° C.-1000° C. | 50% $O_2$ | 1.67%,<br>R = 99.8%,<br>TR = 285° C. |

*The first number refers to weight-based oxygen storage capacity, R refers to percent of recoverable oxygen capacity, TR refers to the initial reduction temperature.

A similar screening method was adopted for CL $CO_2$-splitting. From a thermodynamic perspective, a high equilibrium $P_{O2}$ leads to low $CO_2$ conversion in the splitting step and over oxidation of the syngas product in the methane $P_{Ox}$ step. In contrast, a low $P_{O2}$ can lead to low methane conversion. An optimal range of $P_{O2}$, illustrated in FIG. 1B, can be calculated via Gibbs free energy minimization. This corresponds to a target range of $$\Delta G_{exp}\begin{cases} \in [2.23, 2.24]\text{ eV at }800^\circ\text{ C.} \\ \in [2.13, 2.41]\text{ eV at }950^\circ\text{ C.} \end{cases}.$$

To account for DFT calculation errors, the target ΔG ranges are relaxed to $$\Delta G_{target}\begin{cases} \in [1.93, 2.74]\text{ eV at }800^\circ\text{ C.} \\ \in [1.83, 2.91]\text{ eV at }950^\circ\text{ C.} \end{cases}.$$

Figure 6C:
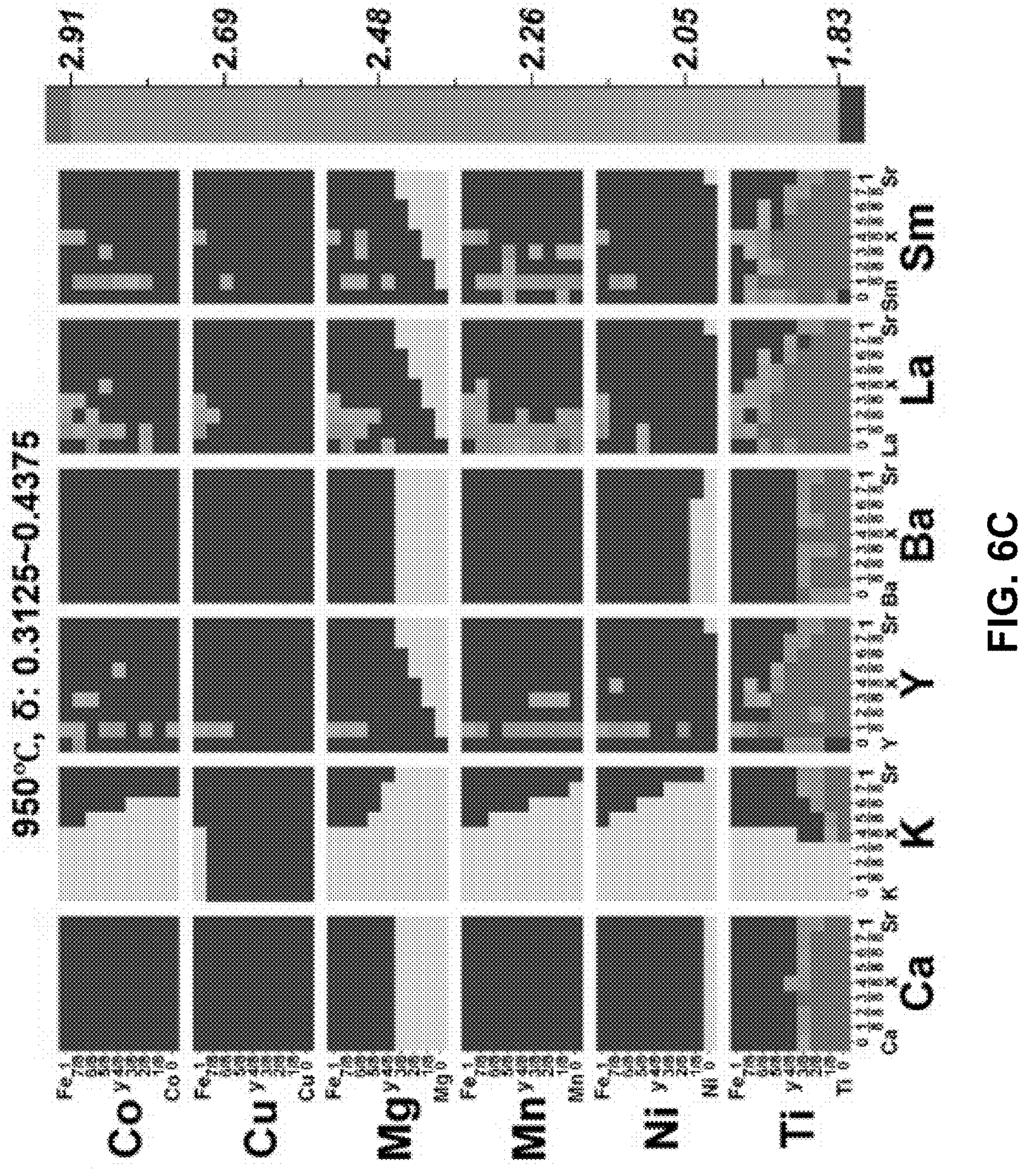

Promising candidates that fall within this target ΔG range are shown in FIG. 6C. At least 482 candidates with ΔGs exist within the target range at least under one of the temperatures. Under a tighter criterion of satisfactory ΔGs at both 800 and 950° C. for δ between 0.25 and 0.5, 30 promising candidates were identified. For some samples with larger $\Delta G_{0.25\rightarrow 0.375}$ (>3 eV), their δs are not likely to reach above 0.25. Therefore, δ ranges of 0-0.125, 0.125-0.25, and 0.0625-0.1875 were also taken into account, leading to 55 additional samples that are promising. Using the same criteria, 4267 samples with 5 cation elements were predicted by M L.

Figure 6D:
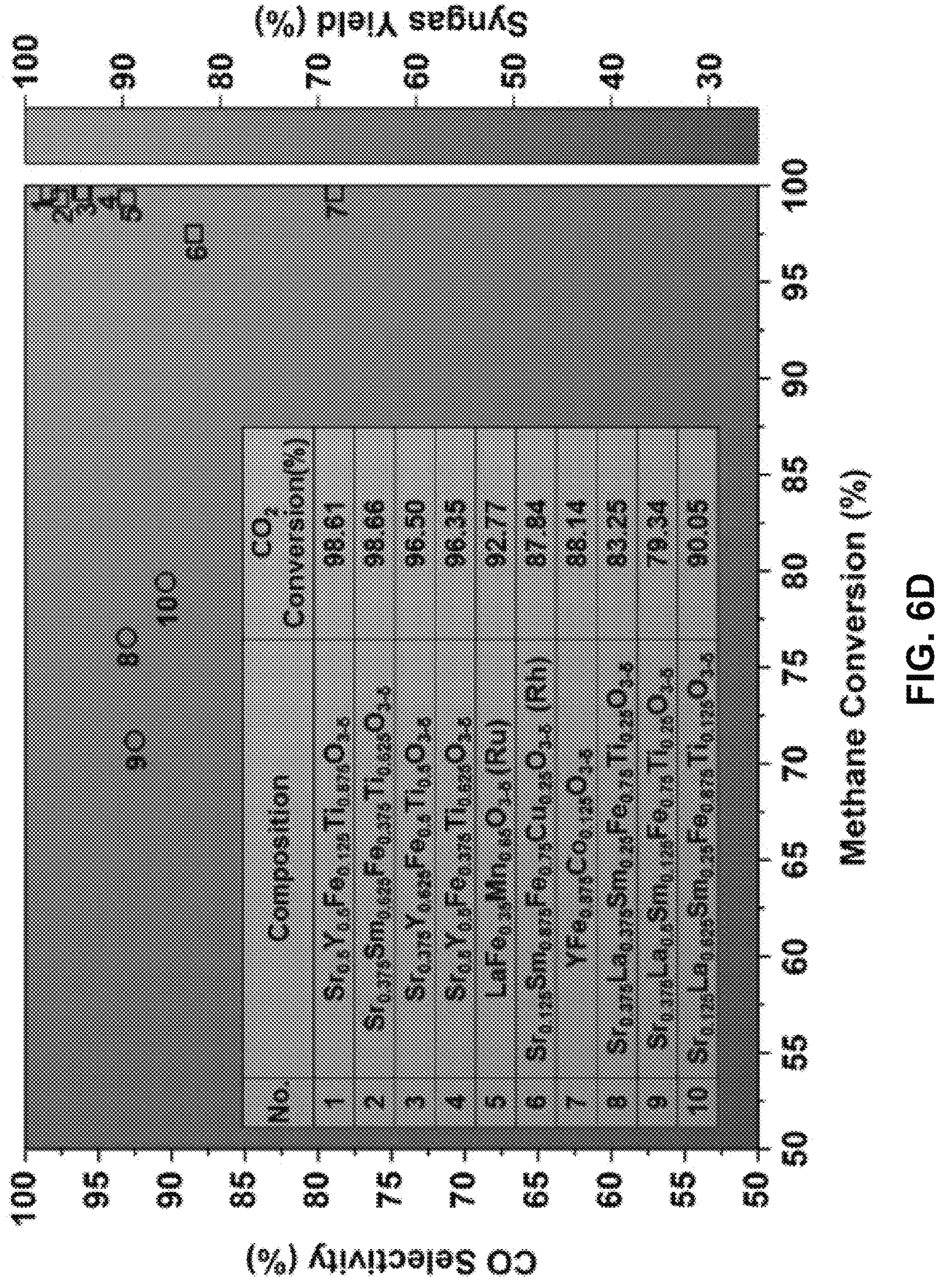
Figure 7A:
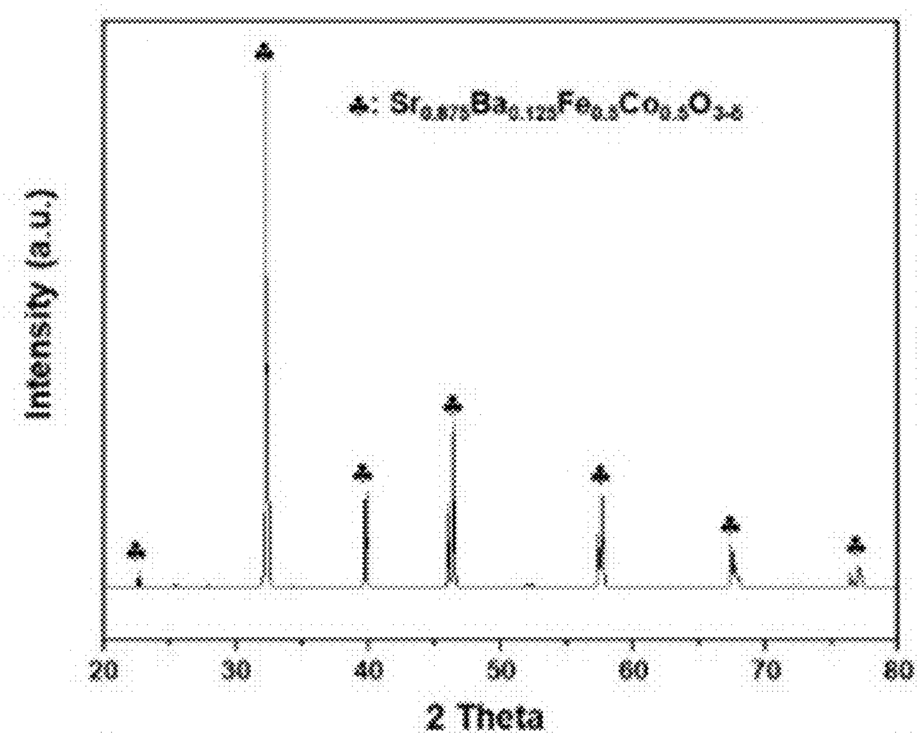
FIGS. 7A-7O show experimental XRD patterns of as-prepared perovskites for CLAS. All samples showed main phases of perovskites. Some showed minor impurities of metal oxides.
Figure 7B:
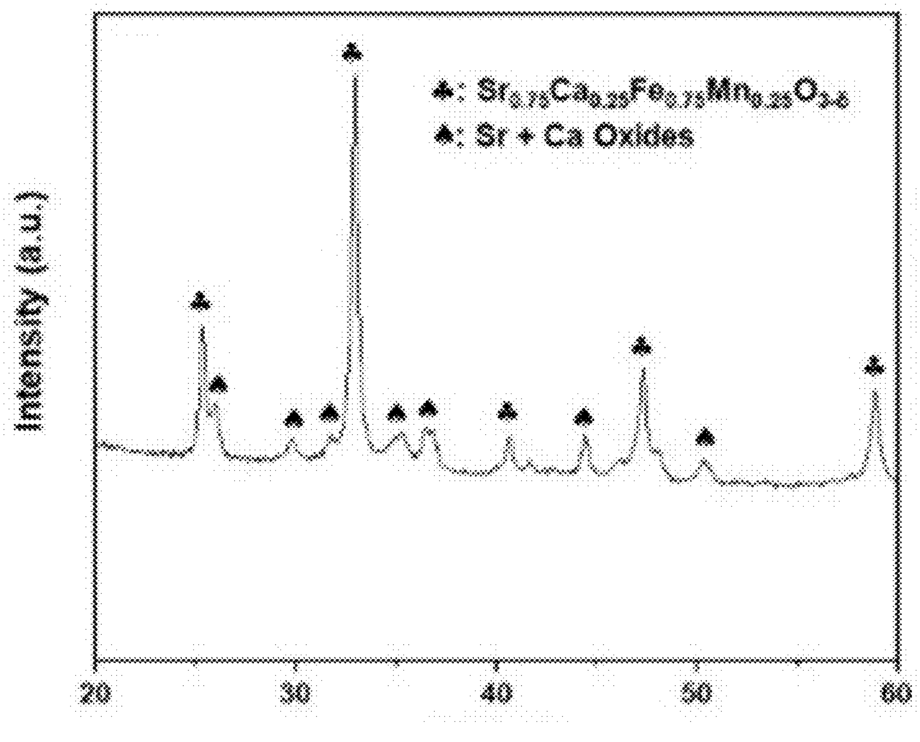
Figure 7C:
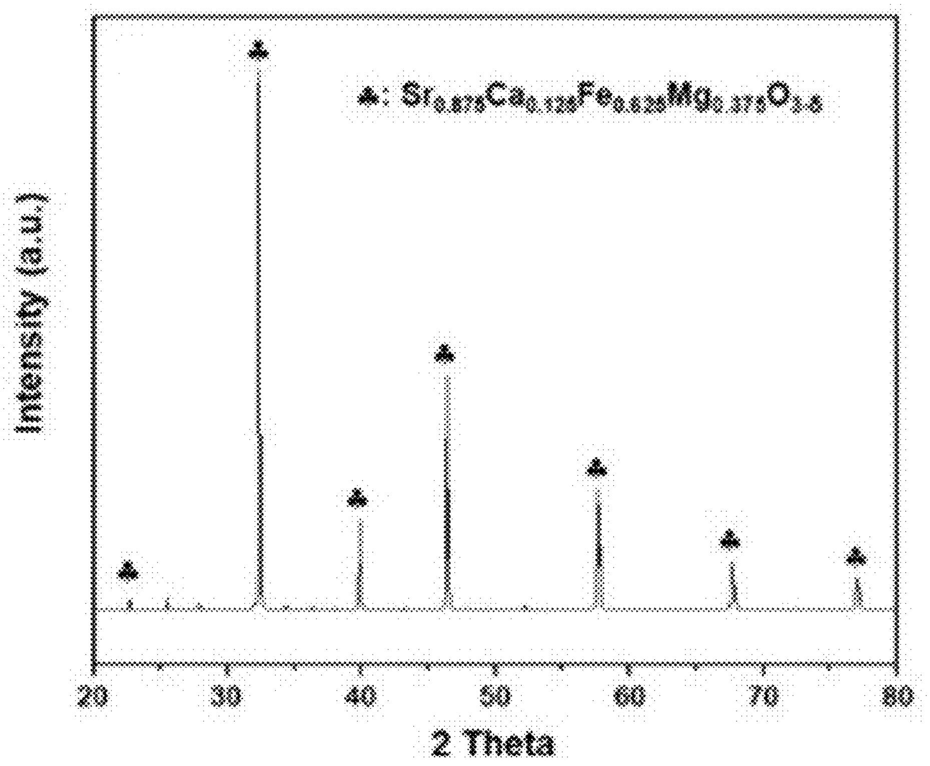
Figure 7D:
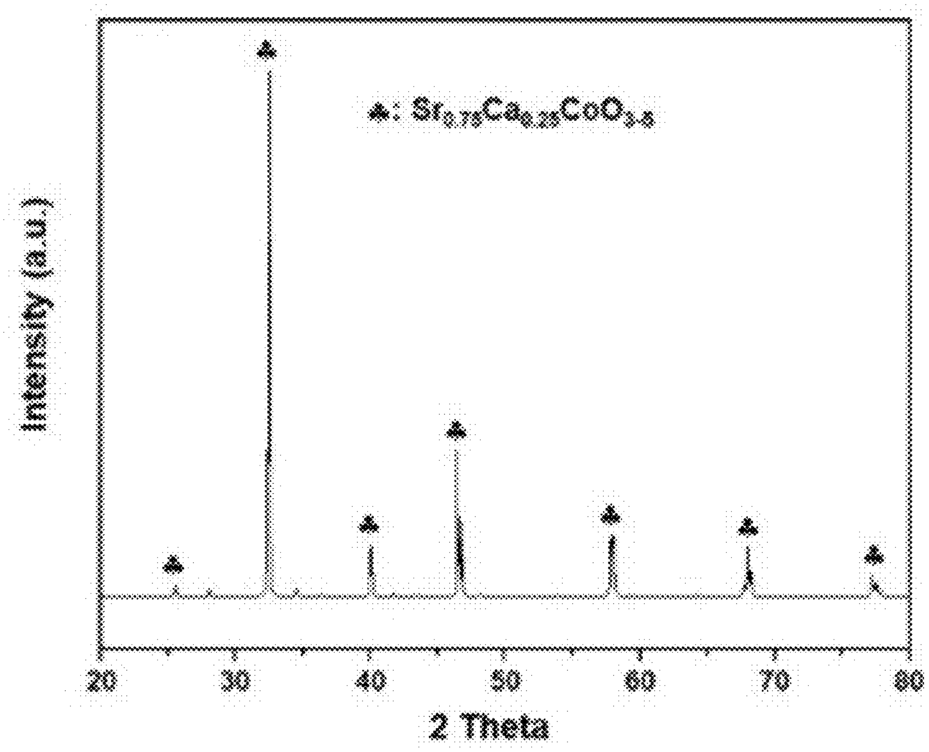
Figure 7E:
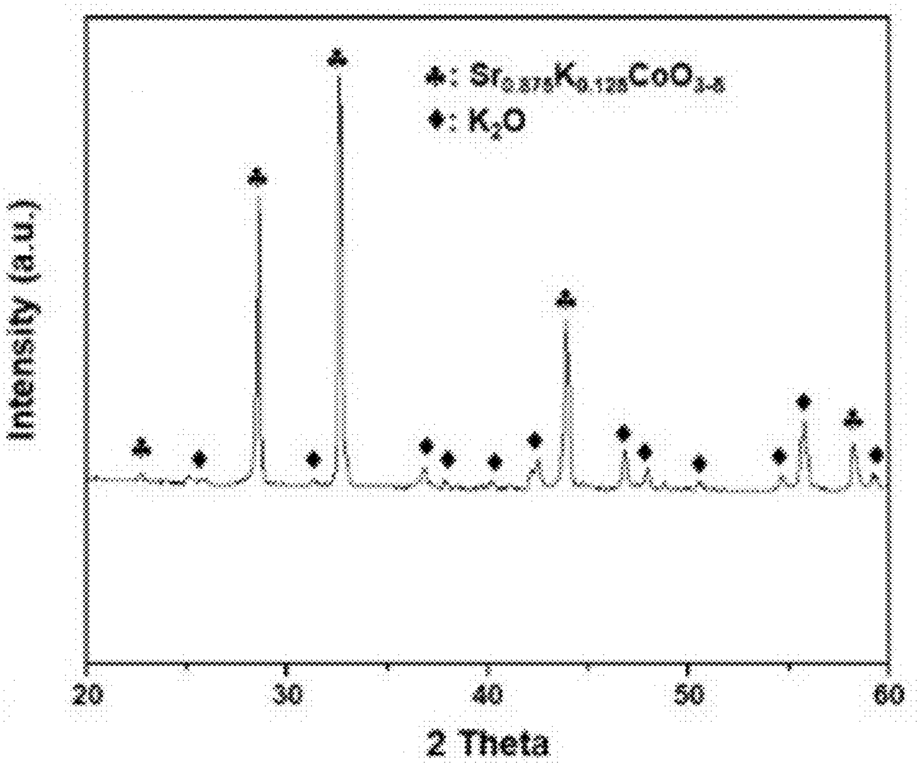
Figure 7F:
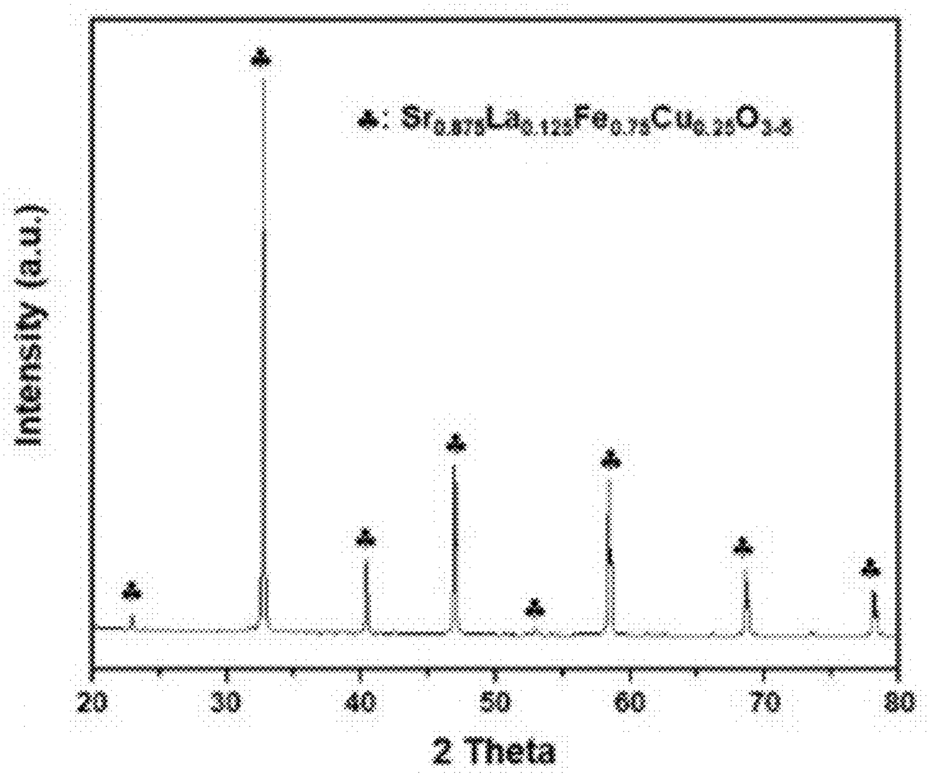
Figure 7G:
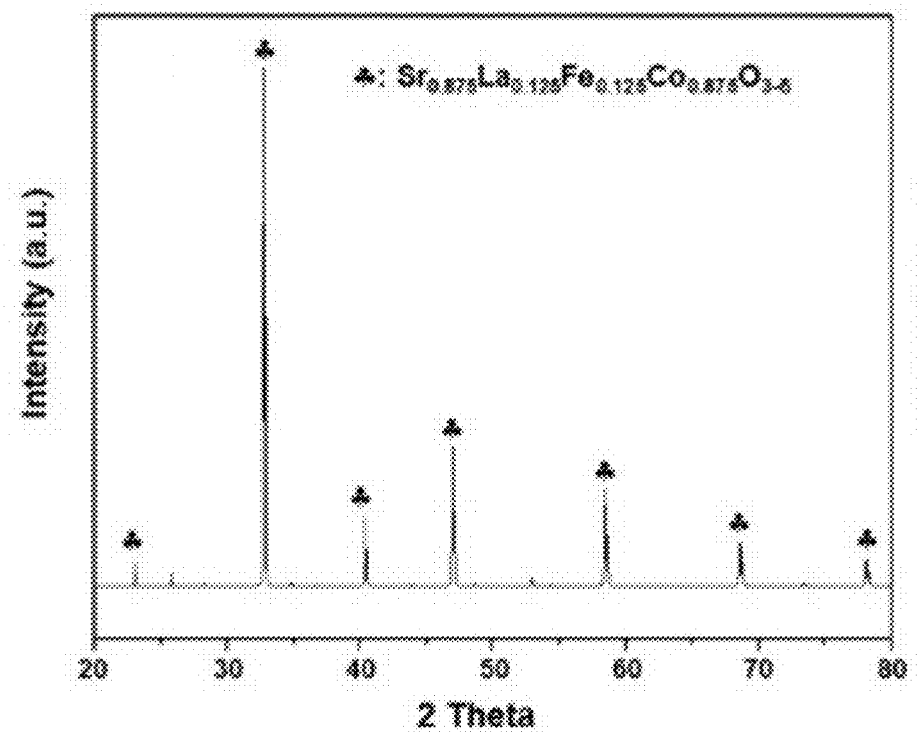
Figure 7H:
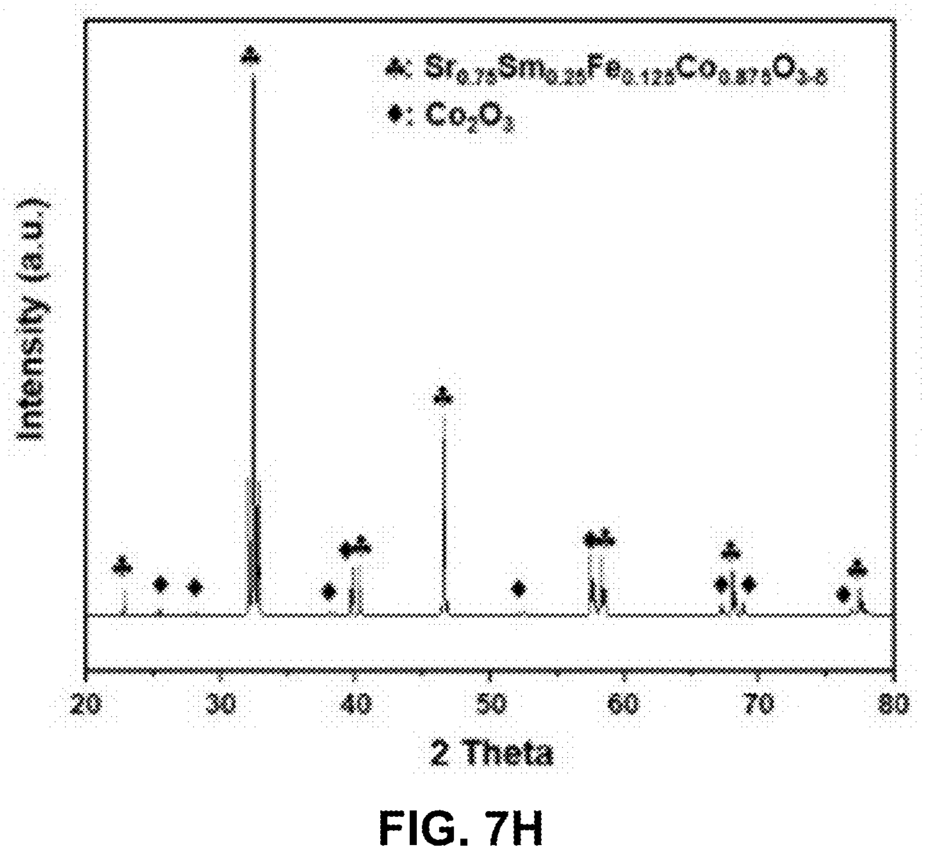
Figure 7I:
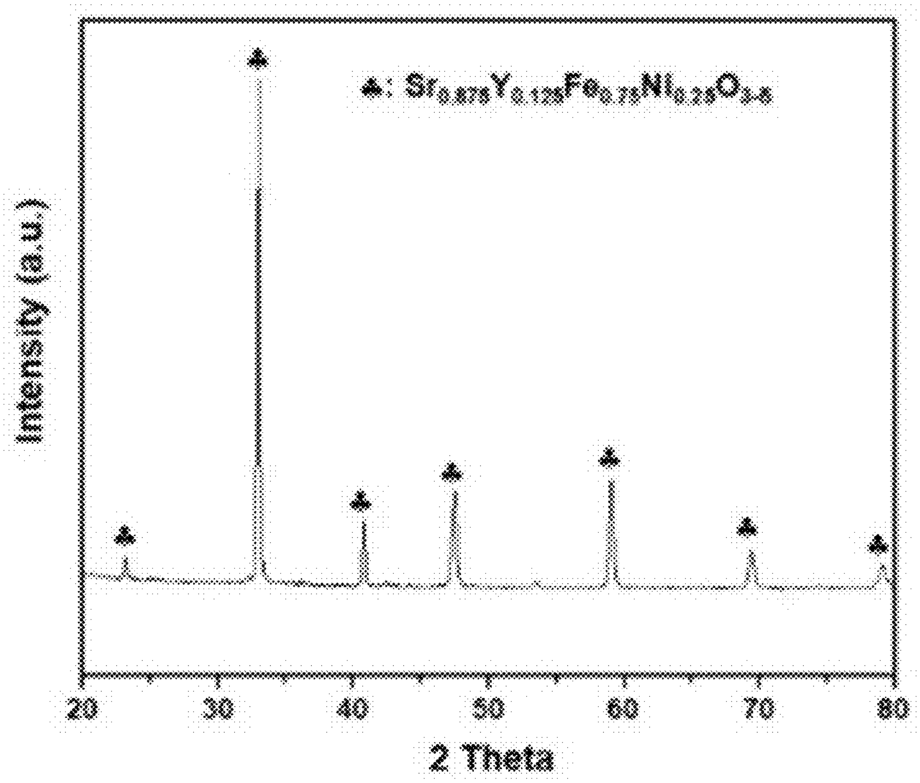
Figure 7J:
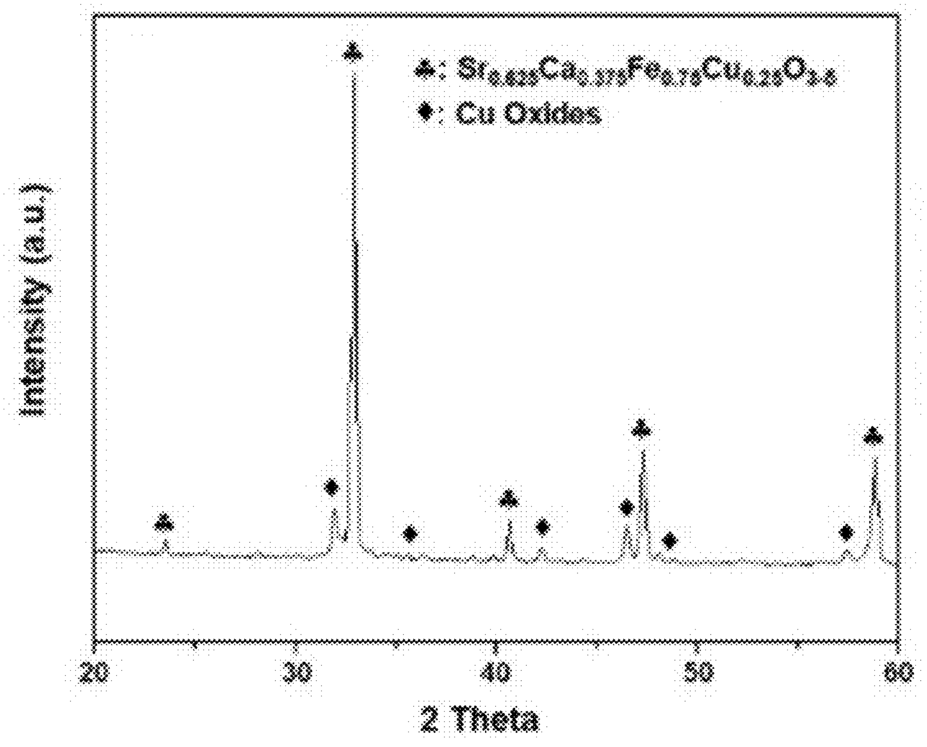
Figure 7K:
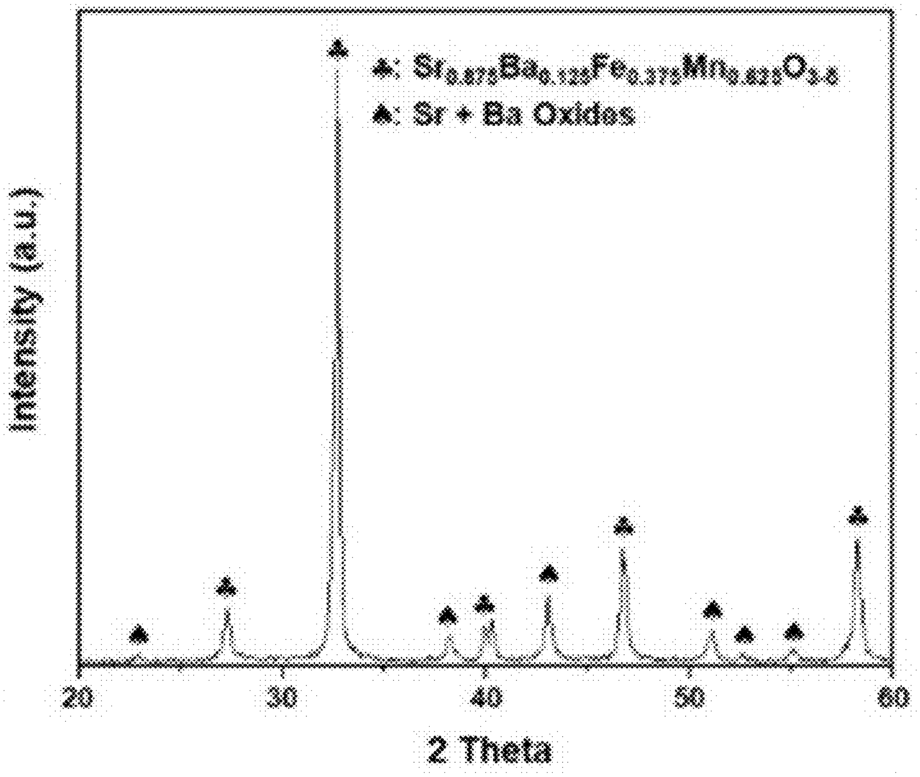
Figure 7L:
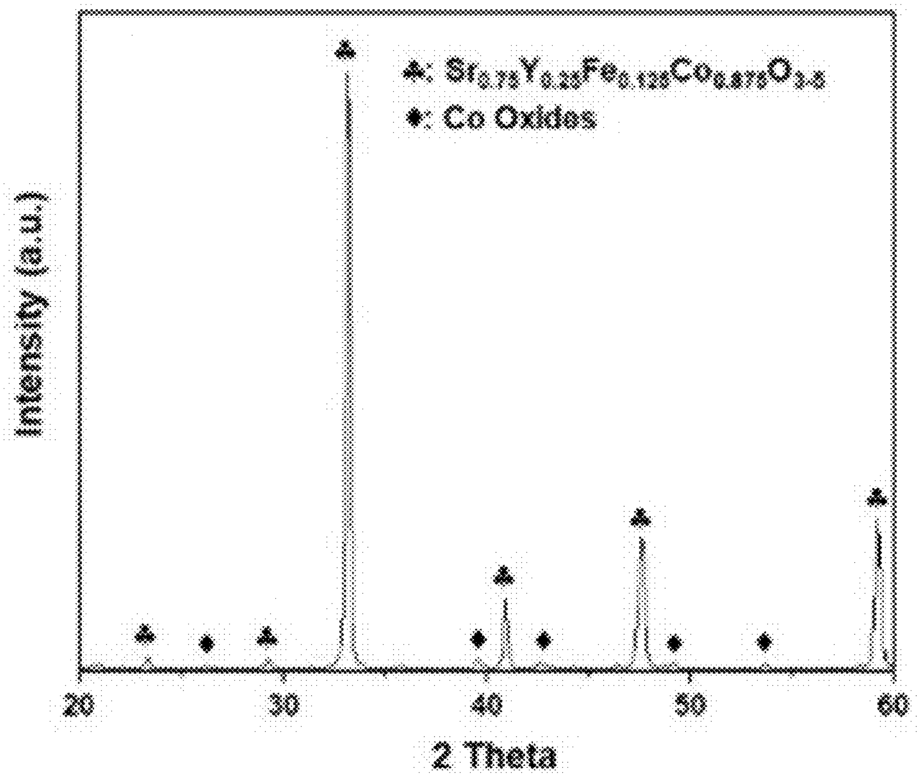
Figure 7M:
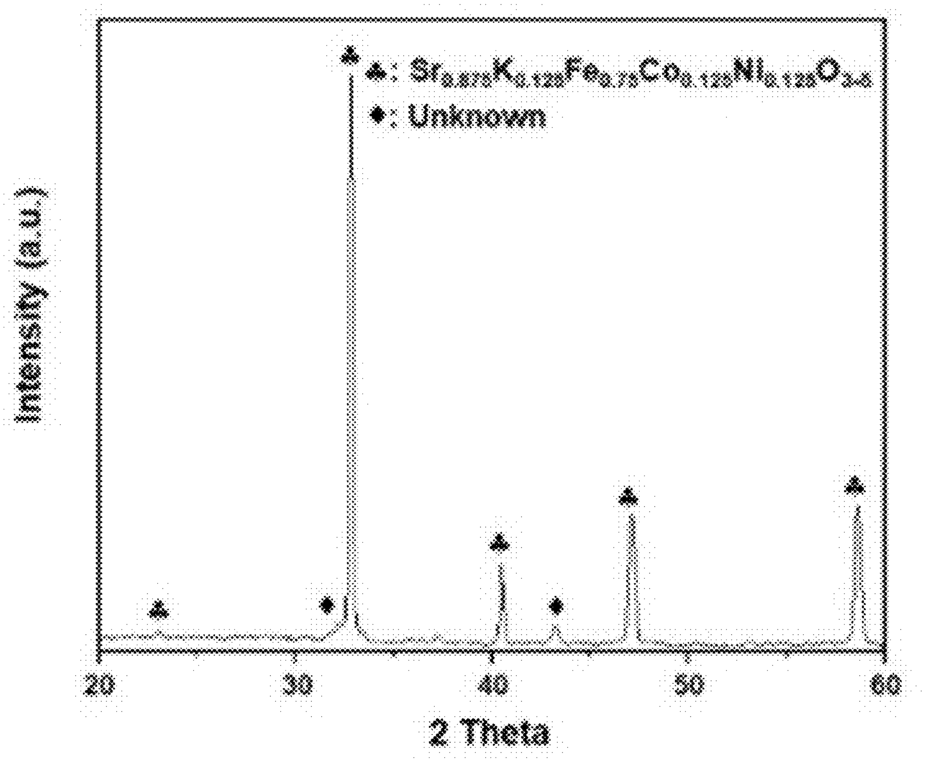
Figure 7N:
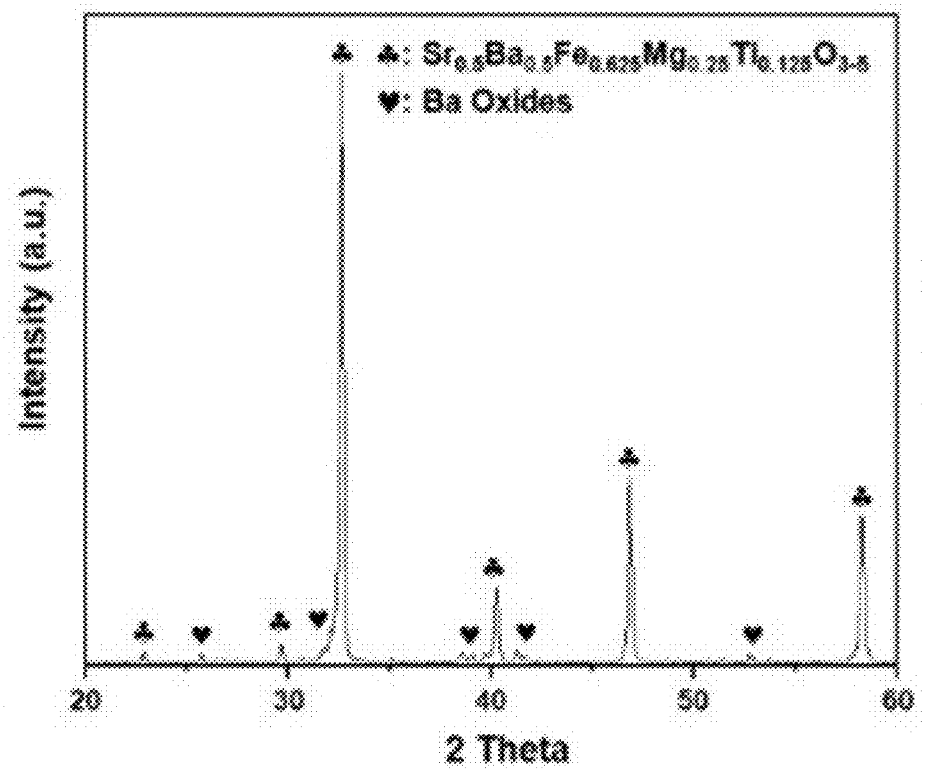
Figure 7O:
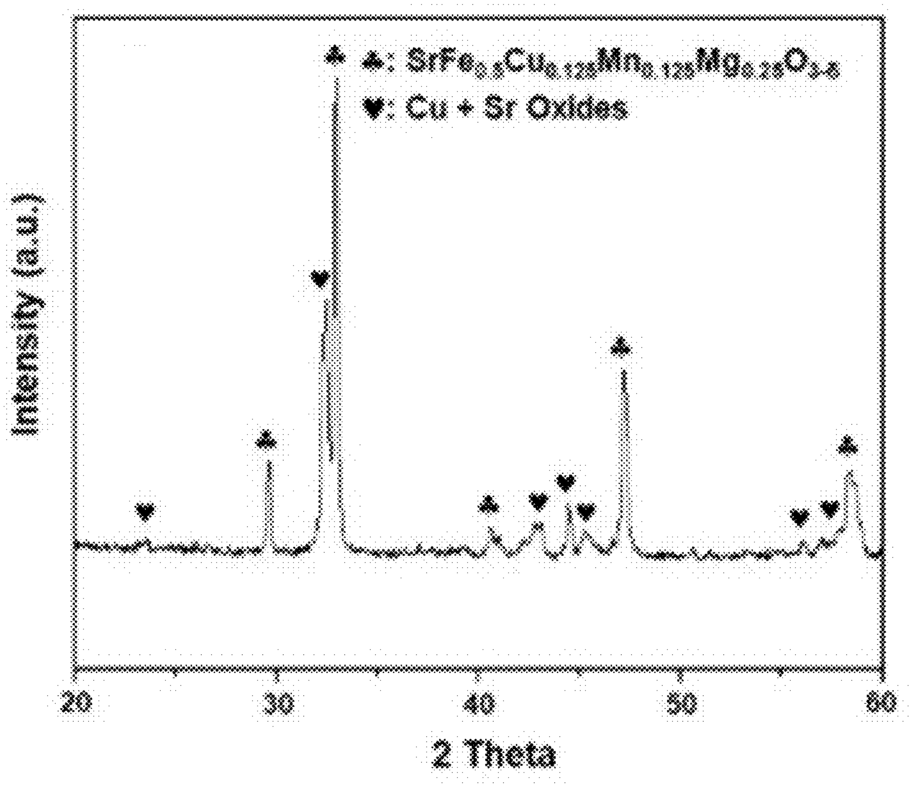
Figure 8A:
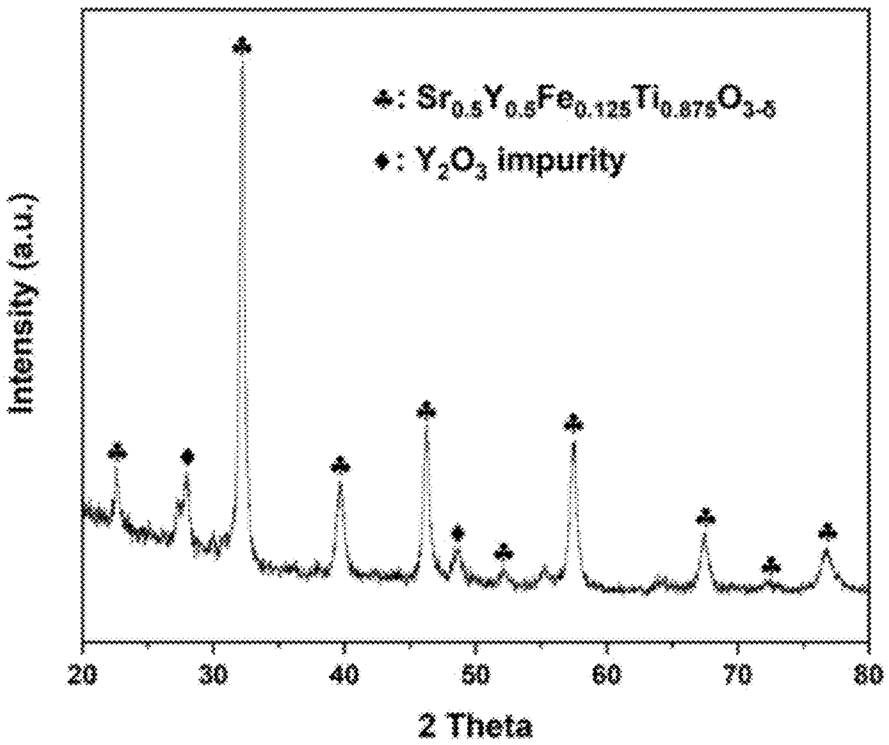
FIGS. 8A-8G show experimental XRD patterns of as-prepared perovskites for CL $CO_2$ splitting. All samples showed main phases of perovskites. Some showed minor impurities of metal oxides.
Figure 8B:
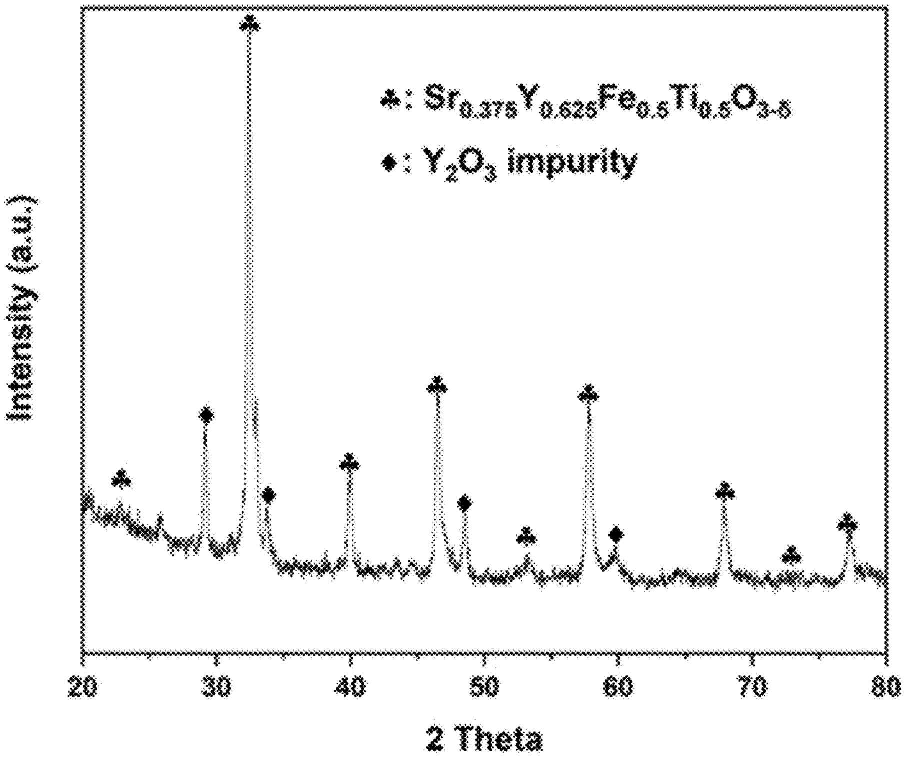
Figure 8C:
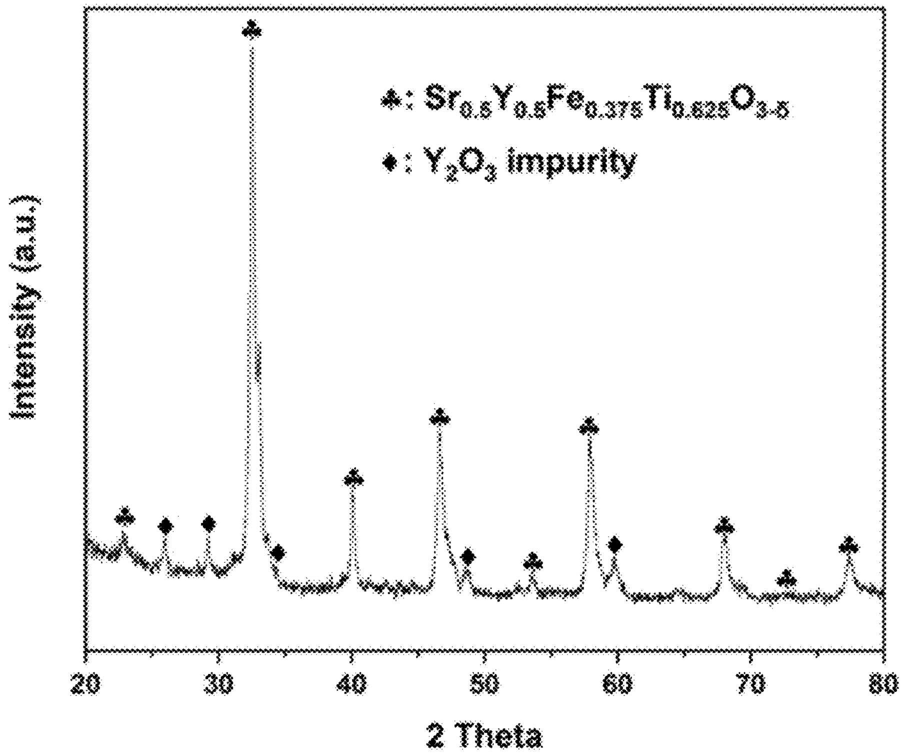
Figure 8D:
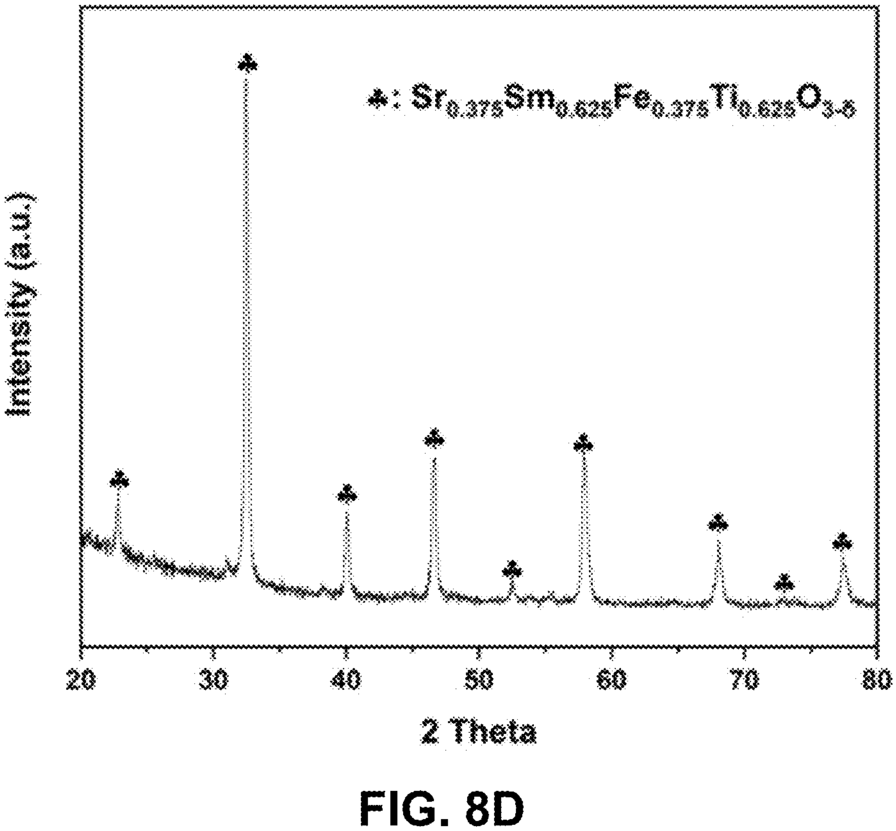
Figure 8E:
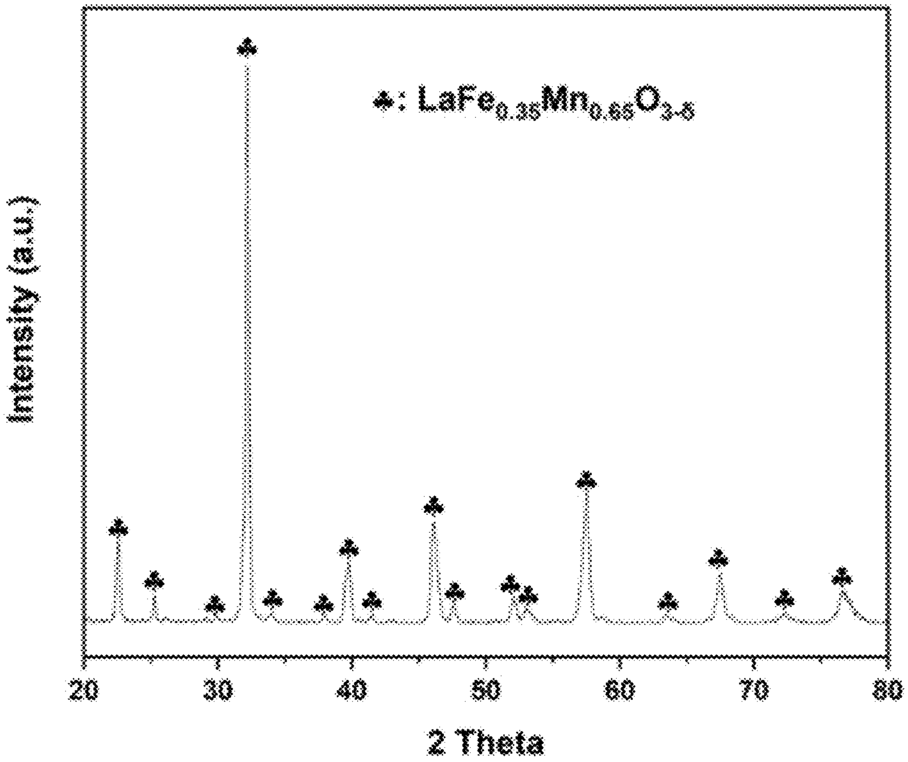
Figure 8F:
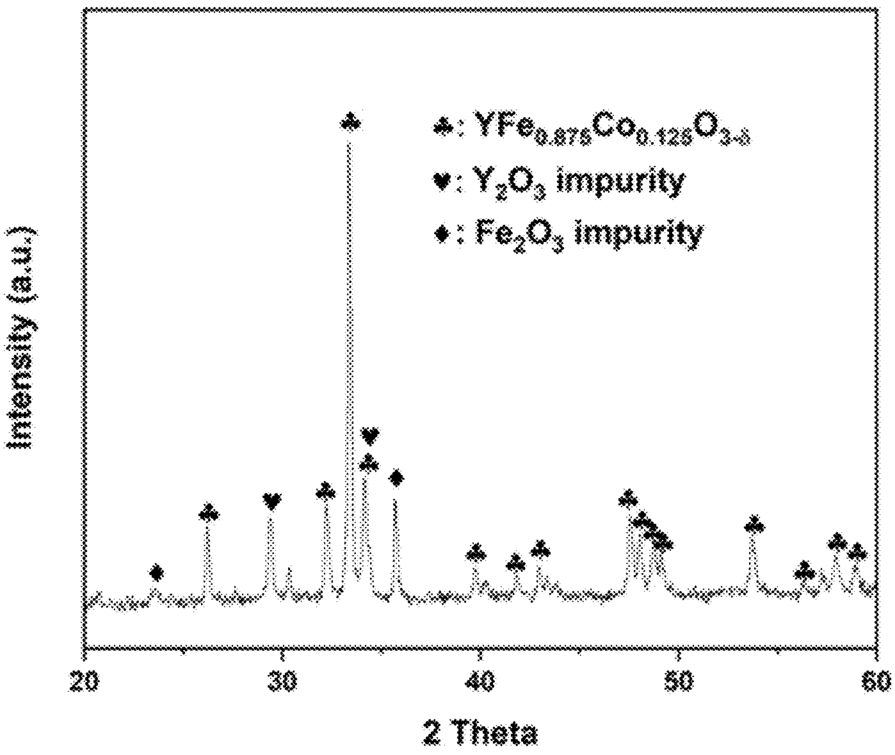
Figure 8G:
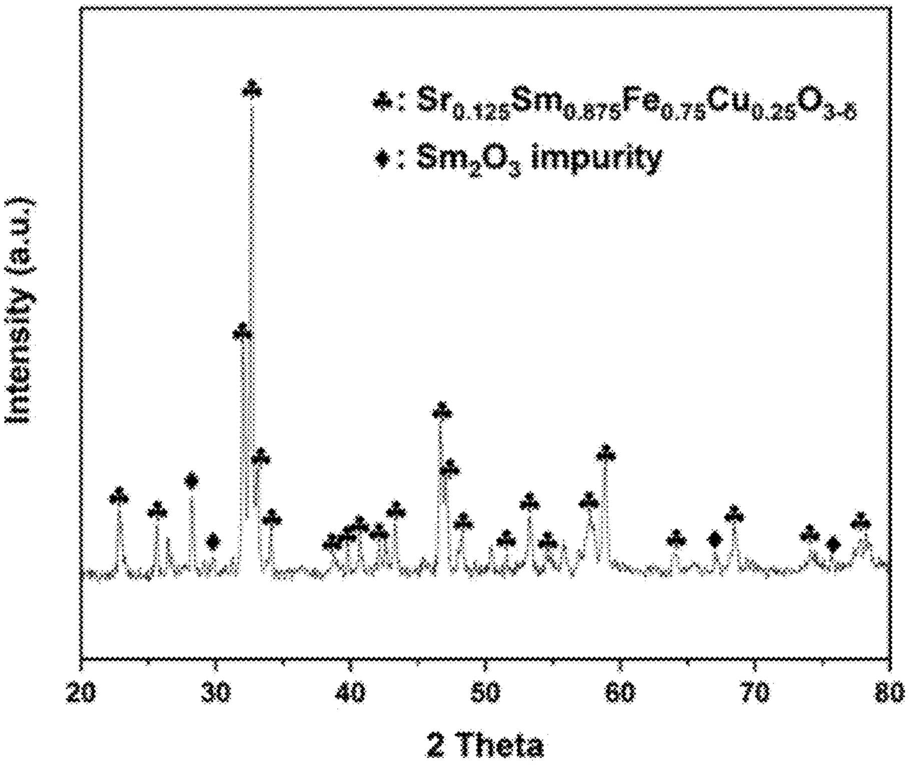

Of the 85 materials predicted by DFT, 4 with very similar compositions have been reported in experimental literature and showed excellent results. 3 additional previously reported compositions were covered by the loose criteria. The lack of literature reports compared to CLAS materials is largely due to relatively few studies on this subject. Of the 81 DFT predicted materials that have not been reported previously, 7 were synthesized for experimental validation. 3 ML predicted materials were also investigated experimentally. These experimental findings are summarized in Table 4. FIG. 6D illustrates the performances of the 10 samples tested in the present study. As can be seen, all 7 DFT-predicted samples exhibited >80% syngas yield and >85% $CO_2$ conversion. And all 3 ML-predicted samples exhibited >70% syngas yield and >80% $CO_2$ conversion. Nearly all these samples are in line with or superior to previously reported materials. Thus, a family of perovskite materials with substantial amount of Ti doping in the B-site, such as $Sr_{0.5}Y_{0.5}Fe_{0.125}Ti_{0.875}O_{3-\delta}$ and $Sr_{0.375}Sm_{0.625}Fe_{0.375}Ti_{0.625}O_{3-\delta}$ were successfully predicted and experimentally verified, and they showed outstanding CL $CO_2$-splitting performances. These materials would be unlikely to be investigated without the high throughput study. The main phases of the 10 samples are all perovskites with some having minor impurities, as verified by XRD.

TABLE 4

Experimental performance of the DFT/ML predicted materials for CL $CO_2$-splitting.

| $Sr_{1-x}A_xFe_{1-y}B_yO_3$ | Tested Composition | Model Predicted Composition | Temperature | Gas Flow* | Results |
|---|---|---|---|---|---|
| A = La | $LaFeO_{3-\delta}$, $Sr_{0.3}La_{0.7}FeO_{3-\delta}$ | $LaFeO_{3-\delta}$[a]<br>$Sr_{0.25}La_{0.75}FeO_{3-\delta}$ | 850° C. | $CH_4/N_2$ = 20/30<br>$H_2O/N_2$ = 578/50 | $X_{CH4}$~50-80%, $S_{CO}$~90% |
| A = La;<br>B = Co | $LaFe_{0.7}Co_{0.3}O_{3-\delta}$,<br>$LaFe_{0.5}Co_{0.5}O_{3-\delta}$,<br>$LaFe_{0.3}Co_{0.7}O_{3-\delta}$ | $Sr_{0.125}La_{0.875}Fe_{0.5}Co_{0.5}O_{3-\delta}$ | 850° C. | $CH_4/N_2$ = 20/30<br>$H_2O/N_2$ = 578/50 | $X_{CH4}$~90%, $S_{CO}$~45% |
| A = La;<br>B = Mn | $LaFe_{0.7}Mn_{0.3}O_{3-\delta}$,<br>$LaFe_{0.5}Mn_{0.5}O_{3-\delta}$ | $LaFe_{0.375}Mn_{0.625}O_{3-\delta}$,<br>$LaFe_{0.625}Mn_{0.375}O_{3-\delta}$ | 850° C. | $CH_4/N_2$ = 20/30<br>$H_2O/N_2$ = 578/50 | $X_{CH4}$~90%, $S_{CO}$~95%,<br>$H_2$ generation<br>capacity~4 mmol/g |
| A = La;<br>B = Ni | $LaFe_{0.5}Ni_{0.1}O_{3-\delta}$ | $LaFe_{0.75}Ni_{0.25}O_{3-\delta}$[a] | 850° C. | $CH_4/N_2$ = 20/30<br>$H_2O/N_2$ = 578/50 | $X_{CH4}$~90% |
| A = La;<br>B = Ni | $LaFe_{0.65}Ni_{0.35}O_{3-\delta}$ | $LaFe_{0.625}Ni_{0.375}O_{3-\delta}$[a] | 750° C. | $CH_4/N_2$ = 2.8/25<br>$CO_2/N_2$ = 1/25 | $X_{CH4}$ = 31%, $S_{CO}$ = 90%,<br>$X_{CO2}$ = 37% |
| A = La;<br>B1 = Cr;<br>B2 = Co | $La_{0.8}Sr_{0.4}Cr_{0.8}Co_{0.2}O_{3-\delta}$ | Cr is not considered in this study | 900° C. | $CH_4/N_2$ = 0.75/14.25<br>$CO_2/N_2$ = 48/252 | CO production rate<br>~100 ml $min^{-1}$ $g^{-1}$ |
| A = La;<br>B = Cr | $Sr_{0.3}La_{0.7}Fe_{0.9}Cr_{0.1}O_{3-\delta}$ | Cr is not considered in this study | 1000° C. | $CH_4/H_2O$<br>Pulse experiment | $X_{CH4}$~70% |
| A = Y;<br>B = Ti | This Study<br>(see the next column) | $Sr_{0.5}Y_{0.5}Fe_{0.125}Ti_{0.875}O_{3-\delta}$ | 950° C. | $CH_4/N_2$ = 2.5/22.5<br>$CO_2/N_2$ = 2.5/22.5 | $X_{CH4}$~100%, $S_{CO}$ = 98%,<br>$X_{CO2}$ = 99%, $Y_{syngas}$ = 98%<br>Oxygen capacity = 0.70 wt % |
| A = Y,<br>B = Ti | This Study | $Sr_{0.375}Y_{0.825}Fe_{0.5}Ti_{0.5}O_{3-\delta}$ | 950° C. | $CH_4/N_2$ = 2.5/22.5<br>$CO_2/N_2$ = 2.5/22.5 | $X_{CH4}$~100%, $S_{CO}$ = 96%,<br>$X_{CO2}$ = 96%, $Y_{syngas}$ = 96%<br>Oxygen capacity = 0.69 wt % |
| A = Y,<br>B = Ti | This Study | $Sr_{0.5}Y_{0.5}Fe_{0.375}Ti_{0.625}O_{3-\delta}$ | 950° C. | $CH_4/N_2$ = 2.5/22.5<br>$CO_2/N_2$ = 2.5/22.5 | $X_{CH4}$~100%, $S_{CO}$ = 96%,<br>$X_{CO2}$ = 96%, $Y_{syngas}$ = 96%<br>Oxygen capacity = 0.69 wt % |
| A = Sm;<br>B = Ti | This Study | $Sr_{0.875}Sm_{0.625}Fe_{0.375}Ti_{0.825}O_{3-\delta}$ | 950° C. | $CH_4/N_2$ = 2.5/22.5<br>$CO_2/N_2$ = 2.5/22.5 | $X_{CH4}$~100%, $S_{CO}$ = 98%,<br>$X_{CO2}$ = 99%, $Y_{syngas}$ = 97%<br>Oxygen capacity = 0.70 wt % |
| A = La,<br>B = Mn | This Study | $LaFe_{0.35}Mn_{0.65}O_{3-\delta}$<br>(1 wt % Ru impregnated) | 950° C. | $CH_4/N_2$ = 2.5/22.5<br>$CO_2/N_2$ = 2.5/22.5 | $X_{CH4}$~100%, $S_{CO}$ = 93%,<br>$X_{CO2}$ = 93%, $Y_{syngas}$ = 93%<br>Oxygen capacity = 0.66 wt % |

TABLE 4-continued

Experimental performance of the DFT/ML predicted materials for CL $CO_2$-splitting.

| $Sr_{1-x}A_xFe_{1-y}B_yO_3$ | Tested Composition | Model Predicted Composition | Temperature | Gas Flow* | Results |
|---|---|---|---|---|---|
| A = Y;<br>B = Co | This Study | $YFe_{0.875}Co_{0.125}O_{3-\delta}$ | 950° C. | $CH_4/N_2$ = 2.5/22.5<br>$CO_2/N_2$ = 2.5/22.5 | $X_{CH4}$~100%, $S_{CO}$ = 80%,<br>$X_{CO2}$ = 80%, $Y_{syngas}$ = 80%<br>Oxygen capacity = 0.63 wt % |
| A = Sm;<br>B = Cu | This Study | $Sr_{0.125}Sm_{0.875}Fe_{0.75}Cu_{0.25}O_{3-\delta}$<br>(0.5 wt % Rh impregnated) | 950° C. | $CH_4/N_2$ = 2.5/22.5<br>$CO_2/N_2$ = 2.5/22.5 | $X_{CH4}$ = 98%, $S_{CO}$ = 89%,<br>$X_{CO2}$ = 88%, $Y_{syngas}$ = 87%<br>Oxygen capacity = 0.63 wt % |
| $A_1$ = La,<br>$A_2$ = Sm;<br>B = Ti | This Study (ML) | $Sr_{0.375}La_{0.375}Sm_{0.25}Fe_{0.75}Ti_{0.25}O_{3-\delta}$ | 950° C. | $CH_4/N_2$ = 2.5/22.5<br>$CO_2/N_2$ = 2.5/22.5 | $X_{CH4}$ = 77%, $S_{CO}$ = 93%,<br>$X_{CO2}$ = 83%, $Y_{syngas}$ = 71%<br>Oxygen capacity = 0.59 wt % |
| $A_1$ = La,<br>$A_2$ = Sm;<br>B = Ti | This Study (ML) | $Sr_{0.875}La_{0.5}Sm_{0.125}Fe_{0.75}Ti_{0.25}O_{3-\delta}$ | 950° C. | $CH_4/N_2$ = 2.5/22.5<br>$CO_2/N_2$ = 2.5/22.5 | $X_{CH4}$ = 71%, $S_{CO}$ = 93%,<br>$X_{CO2}$ = 80%, $Y_{syngas}$ = 71%<br>Oxygen capacity = 0.57 wt % |
| $A_1$ = La,<br>$A_2$ = Sm;<br>B = Ti | This Study (ML) | $Sr_{0.125}La_{0.625}Sm_{0.25}Fe_{0.875}Ti_{0.125}O_{3-\delta}$ | 950° C. | $CH_4/N_2$ = 2.5/22.5<br>$CO_2/N_2$ = 2.5/22.5 | $X_{CH4}$ = 80%, $S_{CO}$ = 90%,<br>$X_{CO2}$ = 90%, $Y_{syngas}$ = 72%<br>Oxygen capacity = 0.64 wt % |

[a]denotes that these materials are screened with a loose criteria.
*All gas flow units are in mL/min.

Example 5: Experimental Conclusions

Using $Sr_xA_{1-x}Fe_yB_{1-y}O_{3-\delta}$ as a model system, the present study developed and experimentally validated DFT and ML based high-throughput simulation approaches to rationally tailor the redox oxygen chemical potential of perovskite oxides. The DFT-based high-throughput model is shown to be effective to identify cation dopant types and concentrations to flexibly adjust the equilibrium oxygen partial pressures of the mixed oxides over 20 orders of magnitude ($10^{-21}$ atm-0.1 atm) and across a large temperature range (400-900° C.). Overall, the oxygen chemical potentials for 2401 perovskite oxides containing up to 4 cation elements were simulated as a function of their oxygen vacancy concentrations (δ). Using these results, 113 materials were predicted to be suitable for chemical looping air separation (CLAS) whereas 85 materials were projected to be ideal for CL based $CO_2$-splitting. The validity of these predictions from DFT was verified experimentally, both in the current study and through previous experimental literature. In total, 43 of the compositions predicted were verified in previous publications, showing excellent performance. Additionally, 25 additional model predicted materials were prepared and evaluated. Out of these, 23 oxygen carriers exhibited satisfactory performances, and 15 showed superior performance compared to most, if not all, the previously reported oxygen carriers. The DFT based high-throughput simulation results were further applied to develop a machine learning (ML) model, which showed satisfactory accuracy. Using the ML model, redox thermodynamics of 227,273 perovskites containing 5 cation elements were investigated, leading to ~20,000 promising oxygen carrier candidates. The prediction by the ML model was further validated by DFT calculations as well as experimental investigations of selected perovskite compositions. Interestingly, the DFT and ML based high-throughput approaches have led to many non-obvious oxygen carrier compositions with superior chemical looping performance, e.g. tripling the oxygen capacity vs. the benchmark oxygen carrier for CLAS. Discovery of these unique compositions, such as $Sr_{0.875}K_{0.125}Fe_{0.75}Co_{0.125}Ni_{0.125}O_{3-\delta}$ and $Sr_{0.375}La_{0.5}Sm_{0.125}Fe_{0.75}Ti_{0.25}O_{3-\delta}$, would be highly unlikely if one adopts conventional oxygen carrier design approaches. As such, the findings in the current study open up a new and effective strategy for rational design of high-performance oxygen carriers. It can also be generalized for tailoring the redox properties of complex oxides beyond chemical looping applications.

Example 6: DFT Calculations

First-principles simulations were performed at the DFT level implemented by the Vienna ab initio Simulation package (VASP) with the frozen-core all-electron projector augmented wave (PAVV) model and Perdew-Burke-Ernzerhof (PBE) functions. A kinetic energy cutoff of 450 eV was used for the plane-wave expansion of the electronic wave function, and the convergence criterions of force and energy were set as 0.01 eV $Å^{-1}$ and $10^{-5}$ eV, respectively. A Gaussian smearing of 0.1 eV was applied for optimizations. Gamma k-point was used for the 2×2×2 $Sr_xA_{1-x}Fe_yB_{1-y}O_{3-\delta}$ perovskite supercells, which contain 40-8δ atoms, to reduce the computational intensity. 1×2×2 Gamma-centered k-points were chosen for brownmillerite structures. The strong on-site coulomb interaction on the d-orbital electrons on the Fe, Co, Cu, Mn, Ni and Ti-sites were treated with the GGA+U approach with $U_{eff}$=4, 3.4, 4, 3.9, 6 and 3 respectively, which gave reasonable predictions of geometric and electronic structures based on previous reports. To make the simulations tractable, only FM phase magnetic ordering was applied for all the doped structures given that magnetic ordering has relatively small effects on the oxygen vacancy formation and migration. The initial spin moment for Fe, Co, Mn, Ni were set to 4, 5, 5, 5, respectively. To make the $Sr_xA_{1-x}Fe_yB_{1-y}O_{3-\delta}$ models closer to randomly disordered solid solution phases, the Monte Carlo special quasirandom structures (MCSQS) method was applied to determine the position of all A- and B-site dopants and oxygen vacancies. The zero-point energy (ZPE), enthalpic (H) and entropic ($S_{vib}$) contributions from phonons were computed by the Phonopy code, while the configurational entropy ($S_{conf}$) were estimated by $\Delta S_{conf}=aR[2\delta\ln(2\delta)+(1-2\delta)\ln(1-2\delta)]$, where R is the ideal gas constant and a is the factor referring to the interaction of oxygen vacancies with a=2 describing an ideal solid solution with no defect interaction. To address the well-known overbinding issue of the $O_2$ molecule within DFT, enthalpy of $O_2$ is computed using $$H_{O_2}(T) = 2H_O^{PAW/PBE}(T) + H_{binding}^{CBS-QB3}(T),$$

$$\text{in which } H_{binding}^{CBS-QB3}(T) = H_{O_2}^{CBS-QB3}(T) - 2H_O^{CBS-QB3}(T),$$

where the CBS-QB3 method is implemented using Gaussian 16.

Example 7: The ML Protocol

All ML algorithms were implemented by Scikit-learn. The random forest (RF) algorithm was applied to establish the relationship between the selected features (the proportion of each A and B site element) and target (ΔG within selected δ ranges) due to its robustness, noise tolerance, and ability to handle complex nonlinear relationships. The RF model is composed of 100 decision trees. Continue increasing the number of trees did not give improved prediction performances. The nodes are expanded until all leaves are pure or until all leaves contain less than 2 samples. A total number of 10,015 datasets were randomly divided into two parts: randomly selected 8,012 datasets were used for training and the remaining 2003 were used for testing. Since the data of features (element ratio) are already from 0 to 1, normalization was unnecessary. The accuracy and robustness of the final machine learning results were verified by a cross-validation technique: all the datasets were randomly and evenly distributed into 5 bins in this procedure with each bin used as a test set while the remaining 4 bins as training sets. Prediction accuracy and errors were evaluated by Pearson correlation coefficients (r) and mean-absolute-errors (MAE).

Example 8: Sample Synthesis and Characterization

The materials were synthesized using either a modified Pechini method or a solid-state reaction method. In a typical synthesis of $A_xA'_{1-x}B_xB'_{1-x}O_3$, stoichiometric amounts of the associated metal nitrates were dissolved in deionized water, roughly 15 mL. Then, citric acid was added to the solution at a molar ratio of 2.5 to 1 and stirred at room temperature for 30 min. In synthesis of Ti-containing materials in the B-site, stoichiometric amount of titanium (IV) butoxide was added into the solution. Then, ethanol was also added into the solution with a mass ratio of ethanol/titanium (IV)

butoxide=10/1. Next, ethylene glycol was added at a molar ratio of 1.5 (ethylene glycol) to 1 (citric acid), and the solution was heated to 80° C. and held for 3 h while being stirred until a gel is formed. The resulting material was heated in an oven at 120° C. for 16 h. The dried sample was calcined in air at 1,000° C. for 8 h to remove the organic compounds and to form the perovskite phase. Finally, the resulting sample was sieved to desired particle size ranges (150-250 μm for TGA testing and 250-450 μm for packed bed experiments). It is noted that Y doped samples needed a slightly lower sintering temperature (900° C. for 10 hours). Solid-state reaction method involves mixing the cation precursor particles in a ball mill followed with similar sintering procedures detailed above. The crystalline phases of the materials synthesized were determined with powder X-ray diffraction (XRD) using a Rigaku SmartLab X-ray diffractometer with Cu Kα (λ=0.15418 nm). The radiation was operated at 40 kV and 44 mA. 2θ angle between 15-60 or 15-80° were used to scan for XRD patterns. All 25 samples prepared contain perovskite as the majority phase. Phase impurities were completely absent in 11 of them, negligibly small in 7, and notable in the remaining 7 samples.

Example 9: Sample Evaluation

CL Air Separation

The capacity, recovery, and initial temperature of weight loss were collected using a thermogravimetric analyzer (TGA Q650). Approximately 50 mg of material was added to an alumina sample cup and placed in the TGA. The flowrate was set to 200 sccm, 100 sccm of oxygen and 100 sccm of Ar, the balance gas. The oxygen concentration was also monitored using a Setnag oxygen analyzer. Initially, the material was heated to 600° C. slowly to remove any water or carbonates present in the material. Then, the program was devised to ramp at 20° C./min to 1000° C. under a 50% oxygen environment, hold at 1,000° C. for 10 minutes, and then cool back to 100° C. at a same ramp rate.

CL $CO_2$ Splitting

The reactivity performance of the synthesized materials were tested in a ⅛ in. ID packed-bed quartz U-tube reactor inside of a tubular furnace. Prior to testing, the materials were pelletized and sieved to 250-450 μm diameter particle size. Then, 0.5 g of the sieved particles were placed into the U-tube. The furnace was then raised to 950° C. under 25 mL/min of Ar flow. Then, an additional 2.8 mL/min $CH_4$ flow was added for 2 min as the $CH_4$ partial oxidation step. Then, the $CH_4$ flow was stopped and the U-tube was purged with Ar for 5 mins. Subsequently, 1.4 mL/min of $CO_2$ was introduced for 4 mins as the $CO_2$ splitting step. After the $CO_2$ splitting step, the U-tube was purged with Ar again for 5 mins prior to the next cycle. The products were measured with a downstream quadruple mass spectroscopy (QMS, MKS Cirrus II). At least 10 cycles were conducted to assure that the reactive performances reach a steady state.

Example 10: Light Hydrocarbon Oxidative Dehydrogenation

Figure 9A:
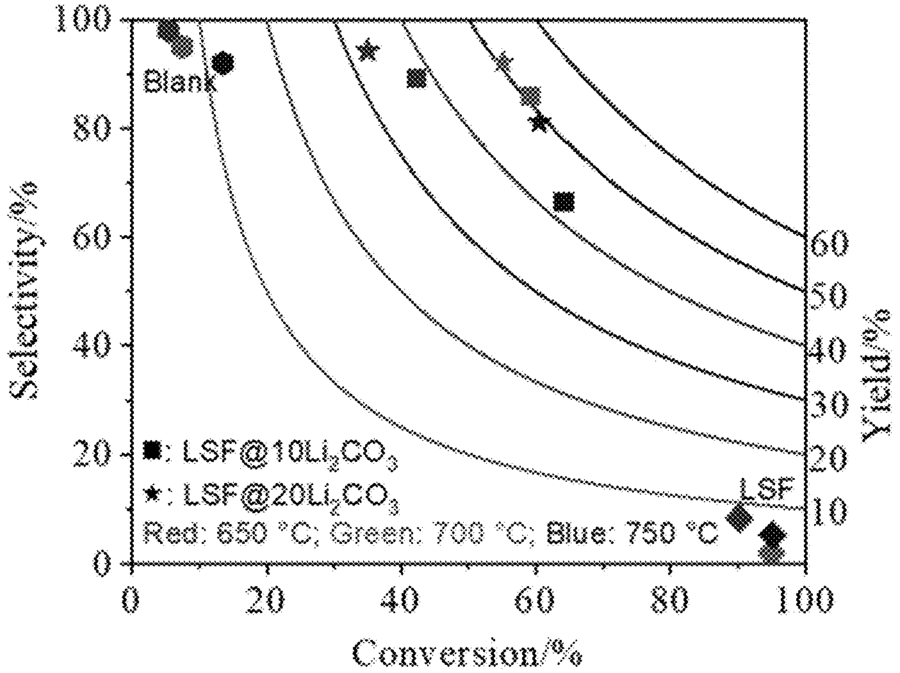
FIG. 9A shows temperature effect and $Li_2CO_3$ loading effect on $La_xSr_{1-x}FeO_3$ LSF≃$Li_2CO_3$ (in this case x=0.2): Space velocity=480 $h^{-1}$. Temperature=700° C.
Figure 9B:
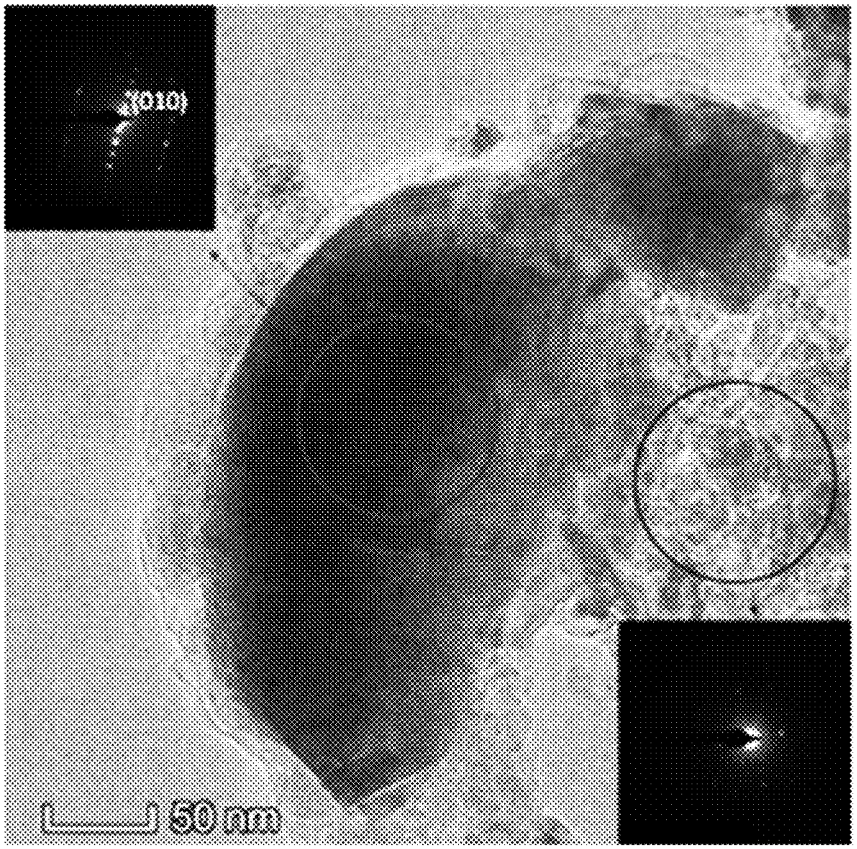
FIG. 9B shows TEM of LSF©$10Li_2CO_3$ (cycled ending in oxidation).
Figure 9C:
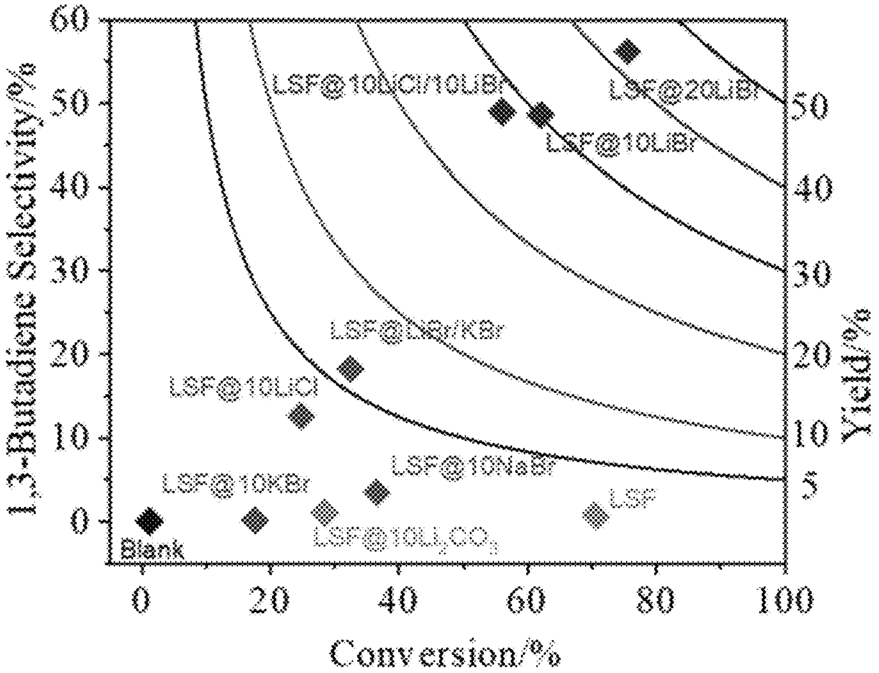
FIG. 9C shows butane ODH performance comparison of LSF, blank and LSF with different promoters: temperature=500° C.; space velocity=450 $h^{-1}$.

Perovskites with low $P_{O2}$ such as $La_{0.8}Sr_{0.2}FeO_3$ or $La_{0.8}Sr_{0.2}Co_{0.2}Fe_{0.8}O_3$ can exhibit high activities for light hydrocarbon (ethane, propane, or butane) oxidative dehydrogenation (ODH) after impregnating their surfaces with alkali carbonate ($Li_2CO_3$, $Na_2CO_3$ and $K_2CO_3$) or alkali halide (LiCl, LiBr, NaCl, NaBr, KCl and KBr). For example, pure $La_{0.8}Sr_{0.2}FeO_3$ exhibits poor selectivity towards ethylene in ethane ODH reaction and mostly combusts ethane into $CO_2$. After impregnating with $Li_2CO_3$, the ethylene selectivity is significantly improved and around 50% of ethylene yield can be achieved at 700° C. (FIG. 9A). Transmission electron microscopy (TEM) showed that an amorphous layer of $Li_2CO_3$ covered the $La_{0.8}Sr_{0.2}FeO_3$ core (FIG. 9B), blocking the unselective sites and creating active peroxide species for ethane ODH. Meanwhile, alkali halide salts can promote butane ODH into butadiene. As shown in FIG. 9C, both pure $La_{0.8}Sr_{0.2}FeO_3$ and $Li_2CO_3$ impregnated $La_{0.8}Sr_{0.2}FeO_3$ exhibit poor selectivity towards butadiene but LiBr impregnated $La_{0.8}Sr_{0.2}FeO_3$ can achieve up to 55% selectivity of butadiene and more than 40% of butadiene yield at 500° C. TEM (FIG. 9D) showed that $La_{0.8}Sr_{0.2}FeO_3$ surface is enriched with Br, indicating that LiBr forms a shell on top of $La_{0.8}Sr_{0.2}FeO_3$.

In another aspect, disclosed herein is method for producing olefinic compounds using the oxygen-deficient mixed metal perovskites disclosed herein, the method including at least the steps of:

(i) contacting the oxygen-deficient mixed metal perovskite or the redox catalyst with one or more dehydrogenation reactants;

(ii) dehydrogenating the one or more dehydrogenation reactants to provide an olefinic compound and hydrogen and a reduced perovskite; and (iii) reoxidizing the reduced perovskite by introducing a gaseous oxidant comprising oxygen to the reduced perovskite to form a reoxidized perovskite; and (iv) re-using the reoxidized perovskite for a subsequent dehydrogenation and selective hydrogen combustion;

wherein at least 30% of the hydrogen released during step (ii) is converted using a lattice oxygen from the perovskite, resulting in formation of steam.

Example 11: Preferred Compositions for CLAS and CL-Based $CO_2$ Splitting and Alkane Conversion Tables 5-7 show the preferred compositions for CLAS and CL-based $CO_2$ splitting and alkane conversion. FIGS. 7A-8G confirmed that the desired phase was formed for the complex oxides predicted, while tables 8 and 9 shows the experimental performance of the preferred compositions.

TABLE 5

113 Desirable Compositions Screened Predicted by DFT Computation for CLAS at 400° C. and 700° C.[a]

| | ΔG (eV) | | | | | |
|---|---|---|---|---|---|---|
| | T = 400° C. | | | T = 700° C. | | |
| δ | 0.25-0.375 | 0.375-0.5 | 0.3125-0.4375 | 0.25-0.375 | 0.375-0.5 | 0.3125-0.4375 |
| BaFeCo-1-0.875-0.125 | 0.48271 | 0.33693 | 0.40982 | −0.03574 | 0.28383 | 0.12405 |
| BaFeTi-1-0.875-0.125 | 0.5933 | 0.36382 | 0.47856 | 0.49613 | 0.08819 | 0.29216 |

TABLE 5-continued

113 Desirable Compositions Screened Predicted by DFT Computation for CLAS at 400° C. and 700° C.[a]

| | ΔG (eV) | | | | | |
|---|---|---|---|---|---|---|
| | T = 400° C. | | | T = 700° C. | | |
| δ | 0.25-0.375 | 0.375-0.5 | 0.3125-0.4375 | 0.25-0.375 | 0.375-0.5 | 0.3125-0.4375 |
| CaFeCo-1-0.5-0.5 | 0.08972 | 0.56377 | 0.32674 | −0.03696 | 0.33952 | 0.15128 |
| CaFeMn-1-0.625-0.375 | 0.50979 | 0.4605 | 0.48514 | 0.30081 | 0.15275 | 0.22678 |
| LaCu-1-1 | 0.58164 | 0.3715 | 0.47657 | 0.07186 | 0.07078 | 0.07132 |
| SrBaFe-0.125-0.875-1 | 0.53478 | 0.10298 | 0.31888 | 0.28772 | −0.17794 | 0.05489 |
| SrBaFeCo-0.125-0.875-0.375-0.625 | 0.14835 | 0.0959 | 0.12213 | −0.19153 | −0.17867 | −0.1851 |
| SrBaFeCo-0.25-0.75-0.625-0.375 | 0.38635 | 0.32112 | 0.35373 | 0.23514 | 0.00333 | 0.11923 |
| SrBaFeCo-0.5-0.5-0.5-0.5 | 0.30449 | 0.59474 | 0.44961 | 0.09269 | 0.2085 | 0.15059 |
| SrBaFeCo-0.625-0.375-0.5-0.5 | 0.03721 | 0.13755 | 0.08738 | −0.18969 | −0.17432 | −0.182 |
| SrBaFeCo-0.75-0.25-0.5-0.5 | 0.23642 | 0.27035 | 0.25339 | 0.02808 | −0.11008 | −0.041 |
| SrBaFeCo-0.75-0.25-0.75-0.25 | 0.28408 | 0.16514 | 0.22461 | 0.05287 | −0.16683 | −0.05698 |
| SrBaFeCo-0.875-0.125-0.375-0.625 | 0.16511 | 0.52432 | 0.34472 | −0.05709 | 0.26353 | 0.10322 |
| SrBaFeCo-0.875-0.125-0.5-0.5 | 0.05355 | 0.12663 | 0.09009 | −0.21381 | −0.00867 | −0.11124 |
| SrBaFeCu-0.5-0.5-0.75-0.25 | 0.11351 | 0.19492 | 0.15422 | −0.17456 | −0.10925 | −0.1419 |
| SrBaFeMg-0.375-0.625-0.5-0.5 | −0.01091 | 0.34401 | 0.16655 | −0.10427 | 0.11638 | 0.00606 |
| SrBaFeMg-0.375-0.625-0.875-0.125 | 0.16771 | 0.07822 | 0.12296 | −0.05453 | −0.11482 | −0.08467 |
| SrBaFeMg-0.75-0.25-0.75-0.25 | −0.09957 | 0.45867 | 0.17955 | −0.13136 | 0.19618 | 0.03241 |
| SrBaFeMg-0.875-0.125-0.75-0.25 | 0.18231 | −0.06099 | 0.06066 | −0.10135 | −0.20737 | −0.15436 |
| SrBaFeMn-0.125-0.875-0.75-0.25 | 0.21511 | 0.52965 | 0.37238 | −0.00363 | 0.24004 | 0.11821 |
| SrBaFeMn-0.25-0.75-0.5-0.5 | 0.37246 | 0.3374 | 0.35493 | 0.18143 | 0.08588 | 0.13366 |
| SrBaFeMn-0.375-0.625-0.2-0.75 | 0.01613 | 0.25094 | 0.13354 | −0.20936 | −0.06259 | −0.13598 |
| SrBaFeMn-0.5-0.5-0.75-0.25 | 0.17028 | 0.2868 | 0.22854 | −0.07792 | 0.12363 | 0.02285 |
| SrBaFeMn-0.625-0.375-0.5-0.5 | 0.0704 | 0.24001 | 0.15521 | −0.20419 | 0.05717 | −0.07351 |
| SrBaFeMn-0.75-0.25-0.25-0.75 | 0.22292 | 0.58233 | 0.40263 | 0.01588 | 0.18357 | 0.09972 |
| SrBaFeMn-0.75-0.25-0.75-0.25 | 0.57074 | 0.43875 | 0.53474 | 0.405 | 0.22733 | 0.31616 |
| SrBaFeMn-0.875-0.125-0.125-0.875 | 0.34797 | 0.17679 | 0.26238 | 0.08093 | −0.06899 | 0.00597 |
| SrBaFeMn-0.875-0.125-0.375-0.625 | 0.17094 | 0.40018 | 0.28556 | −0.05548 | 0.15608 | 0.0503 |
| SrBaFeMn-0.875-0.125-0.5-0.5 | 0.0472 | 0.38986 | 0.21853 | −0.21607 | 0.16122 | −0.02743 |
| SrBaFeNi-0.125-0.875-0.875-0.125 | −0.0962 | 0.19215 | 0.04798 | −0.22659 | −0.0426 | −0.1346 |
| SrBaFeNi-0.375-0.625-0.625-0.375 | 0.16963 | 0.35434 | 0.26199 | −0.09042 | 0.18209 | 0.04584 |
| SrBaFeNi-0.5-0.5-0.75-0.25 | 0.08683 | 0.05129 | 0.06908 | −0.18171 | −0.2099 | −0.19581 |
| SrBaFeNi-0.875-0.125-0.75-0.25 | 0.28202 | 0.35396 | 0.31799 | 0.00711 | 0.1003 | 0.0537 |
| SrCaCo-0.75-0.25-1 | 0.19103 | 0.40577 | 0.2984 | $-6.57 \times 10^{-4}$ | −0.00444 | −0.00255 |
| SrCaFe-0.875-0.125-1 | 0.57668 | 0.57066 | 0.57367 | 0.33086 | 0.34956 | 0.34021 |
| SrCaFeCo-0.125-0.875-0.25-0.75 | 0.05621 | 0.5843 | 0.32026 | −0.22208 | 0.35893 | 0.06842 |
| SrCaFeCo-0.375-0.625-0.125-0.875 | 0.07644 | 0.60242 | 0.33943 | −0.16904 | 0.2367 | 0.03383 |
| SrCaFeCo-0.625-0.375-0.75-0.25 | 0.56823 | 0.41351 | 0.49087 | 0.3065 | 0.21367 | 0.26009 |
| SrCaFeCo-0.75-0.25-0.375-0.625 | 0.06354 | 0.51569 | 0.28961 | −0.03607 | 0.03434 | $-8.66 \times 10^{-4}$ |
| SrCaFeCo-0.75-0.25-0.5-0.5 | 0.09002 | 0.36471 | 0.22736 | −0.06313 | 0.07222 | 0.09455 |
| SrCaFeCo-0.875-0.125-0.375-0.625 | 0.14885 | 0.42105 | 0.28495 | −0.01168 | 0.11173 | 0.05002 |
| SrCaFeCo-0.875-0.125-0.625-0.375 | 0.2067 | 0.44884 | 0.32777 | −0.09003 | 0.07789 | −0.00607 |
| SrCaFeCo-0.875-0.125-0.75-0.25 | 0.29804 | 0.5948 | 0.44642 | −0.01324 | 0.29377 | 0.15351 |
| SrCaFeCu-0.5-0.5-0.75-0.25 | 0.1229 | 0.2283 | 0.1756 | −0.16621 | −0.0796 | −0.1229 |
| SrCaFeCu-0.625-0.375-0.75-0.25 | 0.10208 | 0.26519 | 0.18363 | −0.21872 | 0.00503 | −0.10685 |
| SrCaFeMg-0.125-0.875-0.875-0.125 | 0.34851 | 0.61895 | 0.48373 | 0.13317 | 0.43354 | 0.28336 |
| SrCaFeMg-0.375-0.625-0.875-0.125 | 0.08192 | 0.44763 | 0.26478 | −0.16645 | 0.07125 | −0.0476 |
| SrCaFeMg-0.625-0.375-0.875-0.125 | 0.30938 | 0.34544 | 0.32741 | 0.08771 | 0.07317 | 0.08044 |
| SrCaFeMg-0.875-0.125-0.625-0.375* | 0.14483 | 0.28894 | 0.21689 | −0.07514 | 0.03269 | −0.02122 |
| SrCaFeMn-0.375-0.625-0.625-0.375 | 0.37453 | 0.23396 | 0.30424 | 0.05294 | −0.05668 | −0.00187 |
| SrCaFeMn-0.625-0.375-0.25-0.75 | 0.40468 | 0.24711 | 0.3259 | 0.04259 | −0.15028 | −0.05384 |
| SrCaFeMn-0.625-0.375-0.75-0.25 | 0.10572 | 0.5147 | 0.31021 | −0.10615 | 0.08098 | −0.01258 |
| SrCaFeMn-0.75-0.25-0.25-0.75 | 0.00385 | 0.34819 | 0.17602 | −0.21444 | 0.02792 | −0.09326 |
| SrCaFeMn-0.75-0.25-0.75-0.25 | 0.53013 | 0.3619 | 0.44602 | 0.42755 | 0.02462 | 0.22609 |
| SrCaFeMn-0.875-0.125-0.25-0.75 | 0.35706 | 0.52131 | 0.43919 | 0.03505 | 0.27756 | 0.15631 |
| SrCaFeMn-0.875-0.125-0.375-0.625 | 0.2352 | 0.56394 | 0.39957 | −0.01947 | 0.34458 | 0.16255 |
| SrCaFeNi-0.125-0.875-0.25-0.75 | 0.06578 | 0.18893 | 0.12736 | −0.05503 | −0.21339 | −0.13421 |
| SrCaFeNi-0.25-0.75-0.75-0.25 | −0.01217 | 0.10001 | 0.04392 | −0.10069 | −0.15425 | −0.12747 |
| SrCaFeNi-0.625-0.375-0.625-0.375 | 0.11689 | 0.2378 | 0.17734 | −0.04446 | −0.19482 | −0.11964 |
| SrCaMn-0.5-0.5-1 | 0.24631 | 0.17118 | 0.20874 | −0.04433 | −0.1354 | −0.08987 |
| SrCaMn-0.675-0.125-1 | 0.26709 | 0.12885 | 0.19797 | −0.11171 | −0.16091 | −0.13631 |
| SrFeCo-1-0.375-0.625 | 0.12955 | 0.41986 | 0.27471 | −0.11361 | 0.15769 | 0.02204 |
| SrFeCo-1-0.625-0.375 | 0.19303 | 0.41837 | 0.3057 | 0.07862 | 0.114 | 0.99631 |
| SrFeCu-1-0.75-0.25 | 0.30731 | 0.41729 | 0.3623 | 0.07264 | 0.10923 | 0.09093 |
| SrFeMn-1-0.25-0.75 | 0.13157 | 0.28482 | 0.2082 | −0.16554 | 0.03328 | −0.06613 |
| SrFeMn-1-0.375-0.625 | 0.00106 | 0.05198 | 0.02652 | −0.20494 | −0.21165 | −0.20829 |
| SrFeMn-1-0.5-0.5 | 0.52152 | 0.21742 | 0.36947 | 0.29186 | −0.02942 | 0.13122 |
| SrFeMn-1-0.625-0.375 | 0.51378 | 0.15933 | 0.33655 | 0.35306 | −0.04384 | 0.15461 |
| SrKCo-0.875-0.125-1 | 0.32613 | 0.09959 | 0.21286 | 0.10637 | −0.14991 | −0.02177 |
| SrKFe-0.625-0.375-1 | 0.27688 | 0.12352 | 0.2002 | 0.01242 | −0.15055 | −0.06906 |
| SrKFe-0.875-0.125-1 | 0.4351 | 0.57842 | 0.50676 | 0.17555 | 0.22575 | 0.20065 |
| SrKFeCo-0.875-0.125-0.75-0.25 | 0.44088 | 0.46146 | 0.45117 | 0.20654 | 0.14667 | 0.17661 |
| SrKFeMg-0.875-0.125-0.625-0.375 | 0.0851 | −0.0433 | 0.0209 | −0.20243 | −0.21451 | −0.20847 |
| SrKFeMn-0.875-0.125-0.375-0.625 | 0.10576 | 0.35482 | 0.23029 | −0.10413 | 0.09299 | 0.00557 |

TABLE 5-continued

113 Desirable Compositions Screened Predicted by DFT Computation for CLAS at 400° C. and 700° C.[a]

| | ΔG (eV) | | | | | |
|---|---|---|---|---|---|---|
| | T = 400° C. | | | T = 700° C. | | |
| δ | 0.25-0.375 | 0.375-0.5 | 0.3125-0.4375 | 0.25-0.375 | 0.375-0.5 | 0.3125-0.4375 |
| SrKFeMn-0.875-0.125-0.75-0.25 | 0.2193 | 0.27336 | 0.24633 | −0.10859 | −0.02782 | −0.0682 |
| SrLaCo-0.75-0.25-1 | 0.56372 | 0.49102 | 0.52737 | 0.31562 | 0.36582 | 0.34072 |
| SrLaCu0.625-0.375-1 | 0.05413 | 0.24897 | 0.15155 | −0.22745 | −0.08991 | −0.15868 |
| SrLaFeCo-0.875-0.125-0.125-0.875 | 0.42866 | 0.48805 | 0.45436 | 0.10681 | 0.24468 | 0.17575 |
| SrLaFeCo-0.675-0.125-0.25-0.75 | 0.17304 | 0.49265 | 0.33284 | −0.10557 | 0.09846 | −0.00355 |
| SrLaFeCo-0.875-0.125-0.5-0.5 | 0.56692 | 0.54863 | 0.55777 | 0.34608 | 0.09996 | 0.22302 |
| SrLaFeCu-0.5-0.5-0.25-0.75 | 0.31725 | 0.12518 | 0.22122 | 0.02344 | −0.17733 | −0.07695 |
| SrLaFeCu-0.625-0.375-0.625-0.375 | 0.56318 | 0.15869 | 0.36094 | 0.28582 | −0.07373 | 0.10604 |
| SrLaFeCu-0.75-0.25-0.625-0.375 | 0.40215 | 0.32947 | 0.36581 | 0.18322 | −0.03735 | 0.07293 |
| SrLaFeCu-0.875-0.125-0.75-0.25 | 0.38722 | 0.25224 | 0.31973 | 0.12097 | −0.07601 | 0.02248 |
| SrLaFeMg-0.25-0.75-0.375-0.625 | 0.11726 | 0.56336 | 0.34031 | −0.091 | 0.26861 | 0.08881 |
| SrLaFeMg-0.875-0.125-0.75-0.25 | 0.08061 | 0.52183 | 0.30122 | −0.13508 | 0.25454 | 0.05974 |
| SrLaFeMg-0.875-0.125-0.875-0.125 | 0.39941 | 0.58209 | 0.49075 | 0.15359 | 0.29215 | 0.22287 |
| SrLaFeMn-0.875-0.125-0.125-0.875 | 0.62728 | 0.58765 | 0.60747 | 0.31892 | 0.20223 | 0.25657 |
| SrLaFeNi-0.375-0.625-0.125-0.675 | 0.61531 | 0.34358 | 0.47944 | 0.36103 | −0.08201 | 0.13951 |
| SrLaFeNi-0.5-0.5-0.125-0.875 | 0.18316 | 0.52621 | 0.35469 | −0.08638 | 0.14479 | 0.02895 |
| SrLaFeNi-0.5-0.5-0.25-0.75 | 0.36177 | 0.25569 | 0.30868 | 0.06507 | −0.18237 | −0.05865 |
| SrLaFeNi-0.625-0.375-0.375-0.625 | 0.48636 | 0.4003 | 0.44333 | 0.18895 | −0.02978 | 0.07958 |
| SrLaFeNi-0.625-0.375-0.625-0.375 | 0.5621 | 0.39105 | 0.47657 | 0.2683 | 0.0213 | 0.1448 |
| SrLaFeNi-0.675-0.125-0.625-0.375 | 0.19229 | 0.60972 | 0.401 | −0.10601 | 0.11205 | 0.00302 |
| SrLaFeNi-0.875-0.125-0.75-0.25 | 0.29413 | 0.47088 | 0.3825 | 0.0507 | 0.09388 | 0.07229 |
| SrLaMn-0.875-0.125-1 | 0.48708 | 0.55239 | 0.51973 | 0.13338 | 0.14077 | 0.13708 |
| SrLaNi-0.375-0.625-1 | 0.09556 | 0.29927 | 0.19741 | −0.15627 | −0.20972 | −0.183 |
| SrSmFeCo-0.75-0.25-0.125-0.875 | 0.52625 | 0.39269 | 0.45947 | 0.28067 | 0.02112 | 0.1509 |
| SrSmFeCu-0.5-0.5-0.5-0.5 | 0.61119 | 0.58763 | 0.59941 | 0.24668 | 0.28835 | 0.26751 |
| SrSmFeCu-0.625-0.375-0.25-0.75 | 0.10814 | 0.48144 | 0.29479 | −0.19438 | 0.13206 | −0.03116 |
| SrSmFeCu-0.625-0.375-0.375-0.625 | 0.09208 | 0.0648 | 0.07844 | −0.20991 | −0.22447 | −0.21719 |
| SrSmFeCu-0.75-0.25-0.5-0.5 | 0.0751 | 0.59838 | 0.33674 | −0.14225 | 0.20816 | 0.03295 |
| SrSmFeMg-0.875-0.125-0.875-0.125 | 0.5867 | 0.3953 | 0.491 | 0.33577 | 0.19833 | 0.26705 |
| SrSmFeNi-0.5-0.5-0.125-0.875 | 0.27836 | 0.43454 | 0.35645 | −0.00732 | 0.09084 | 0.04176 |
| SrSmFeNi-0.625-0.375-0.25-0.75 | 0.37448 | 0.46016 | 0.41732 | 0.06535 | 0.17652 | 0.12094 |
| SrSmNi-0.625-0.375-1 | 0.45082 | 0.22704 | 0.33893 | 0.28953 | −0.06989 | 0.10982 |
| SrYCo-0.675-0.125-1 | 0.39391 | 0.09703 | 0.24547 | 0.11647 | −0.21155 | −0.04754 |
| SrYFeCo-0.75-0.25-0.125-0.875 | 0.49145 | 0.40729 | 0.44937 | 0.33644 | 0.13717 | 0.23681 |
| SrYFeMg-0.875-0.125-0.875-0.125 | 0.52154 | 0.34521 | 0.43337 | 0.25489 | −0.00302 | 0.12593 |
| SrYFeNi-0.5-0.5-0.125-0.875 | 0.47709 | 0.33722 | 0.40716 | 0.16631 | 0.01549 | 0.0879 |
| SrYFeNi-0.875-0.125-0.675-0.375 | 0.5804 | 0.41389 | 0.49715 | 0.36216 | 0.12503 | 0.2436 |
| SrYFeNi-0.75-0.125-0.75-0.25 | 0.48233 | 0.35114 | 0.41673 | 0.18164 | 0.10616 | 0.1439 |
| SrYNi-0.5-0.5-1 | 0.11067 | 0.19557 | 0.15312 | −0.13807 | −0.14526 | −0.14166 |

Figure 9D:
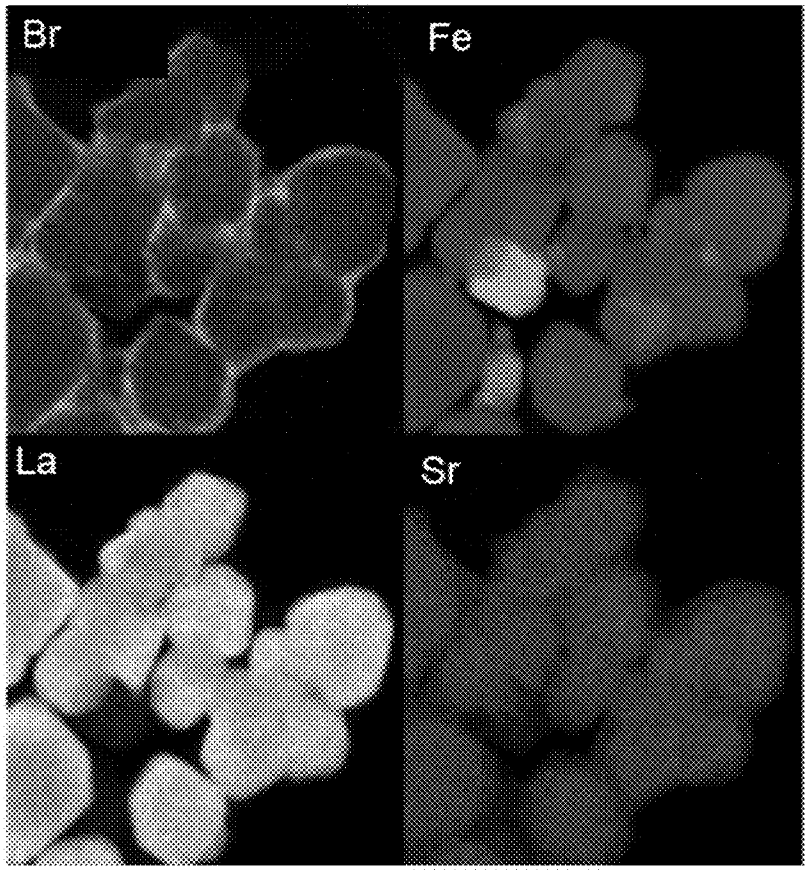
FIG. 9D shows TEM-EDS on LSF@20LiBr.
Figure 10:
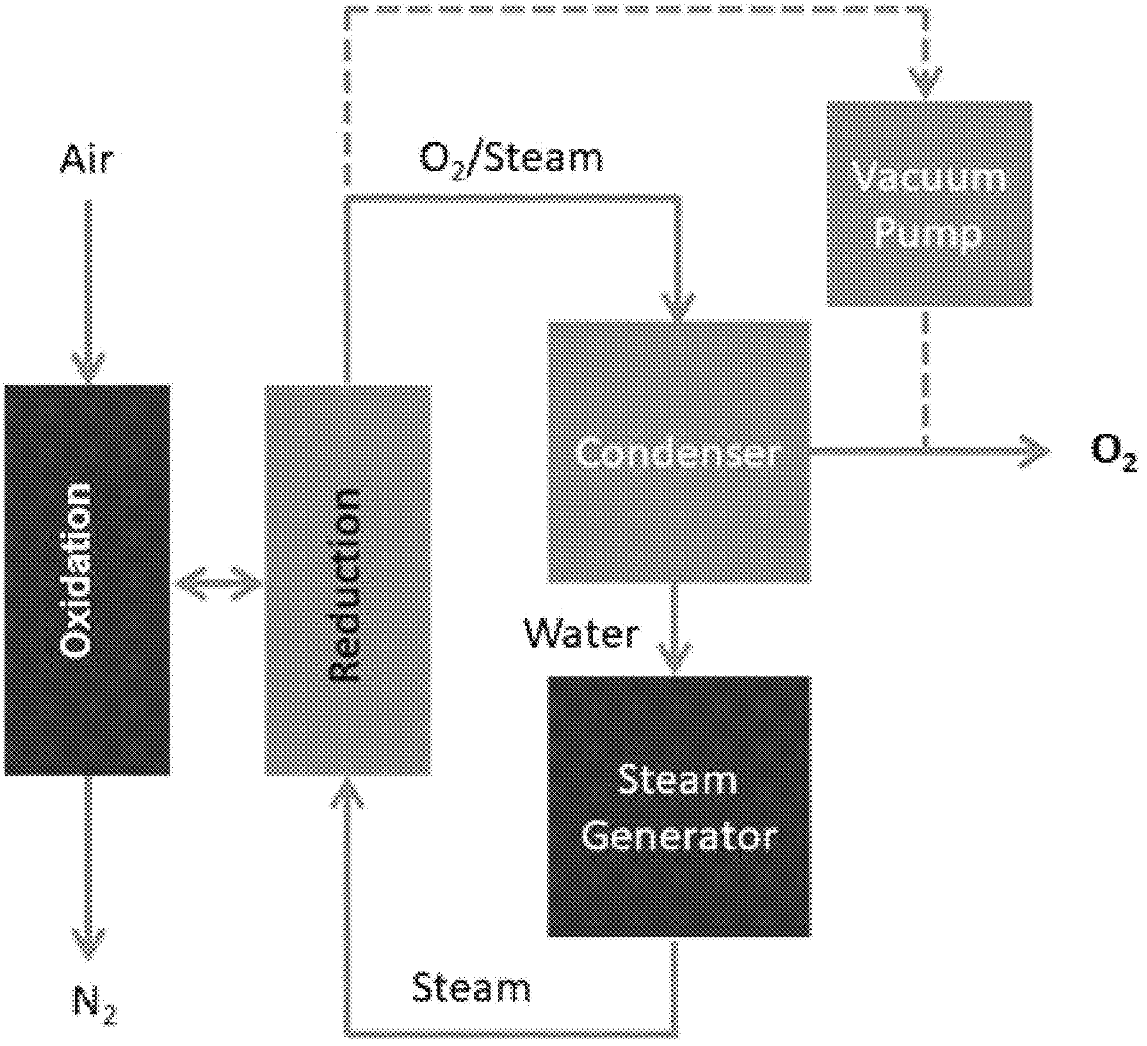
FIG. 10 shows an exemplary schematic for a distributed oxygen production system via steam/vacuum purging using the disclosed perovskites.
Figure 11:
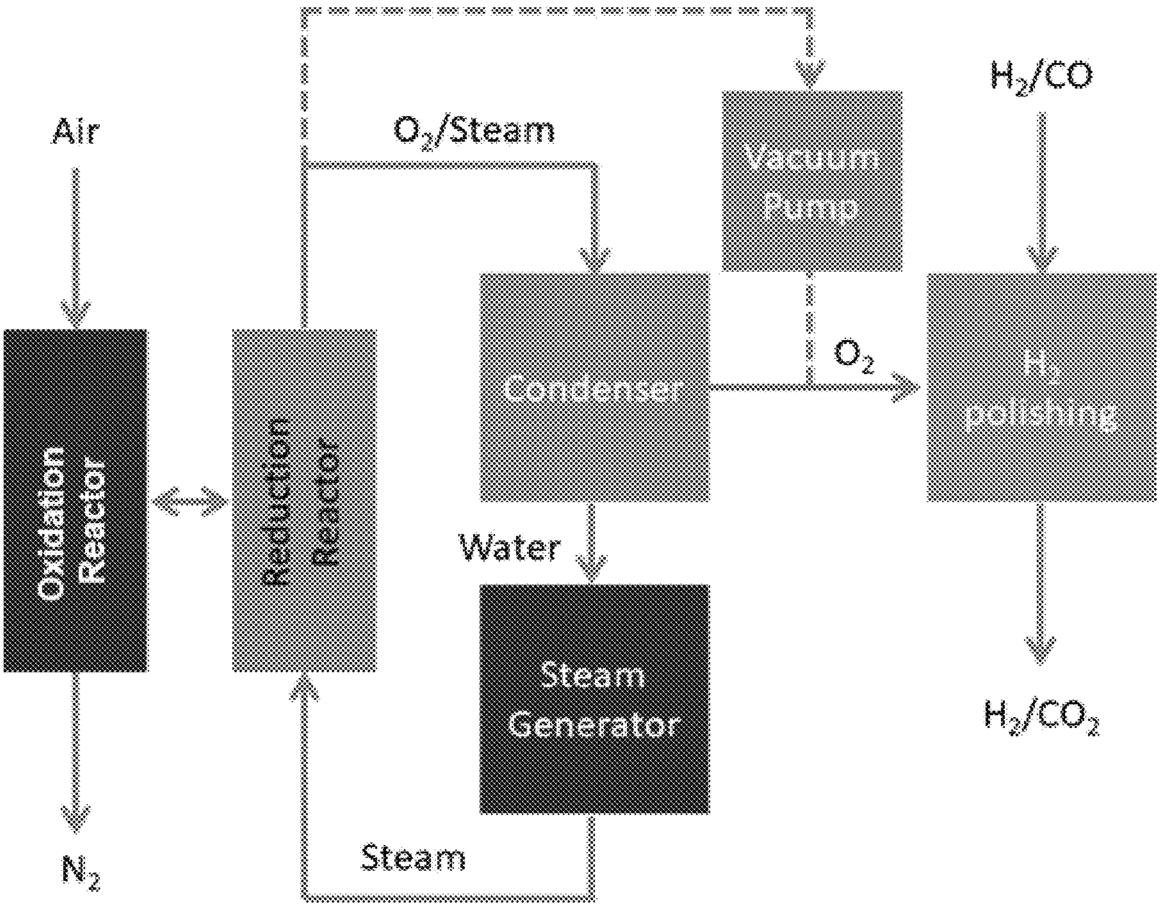
FIG. 11 shows an exemplary schematic for distributed oxygen production for hydrogen purification via selective carbon monoxide oxidation using the disclosed perovskites.
Figure 12:
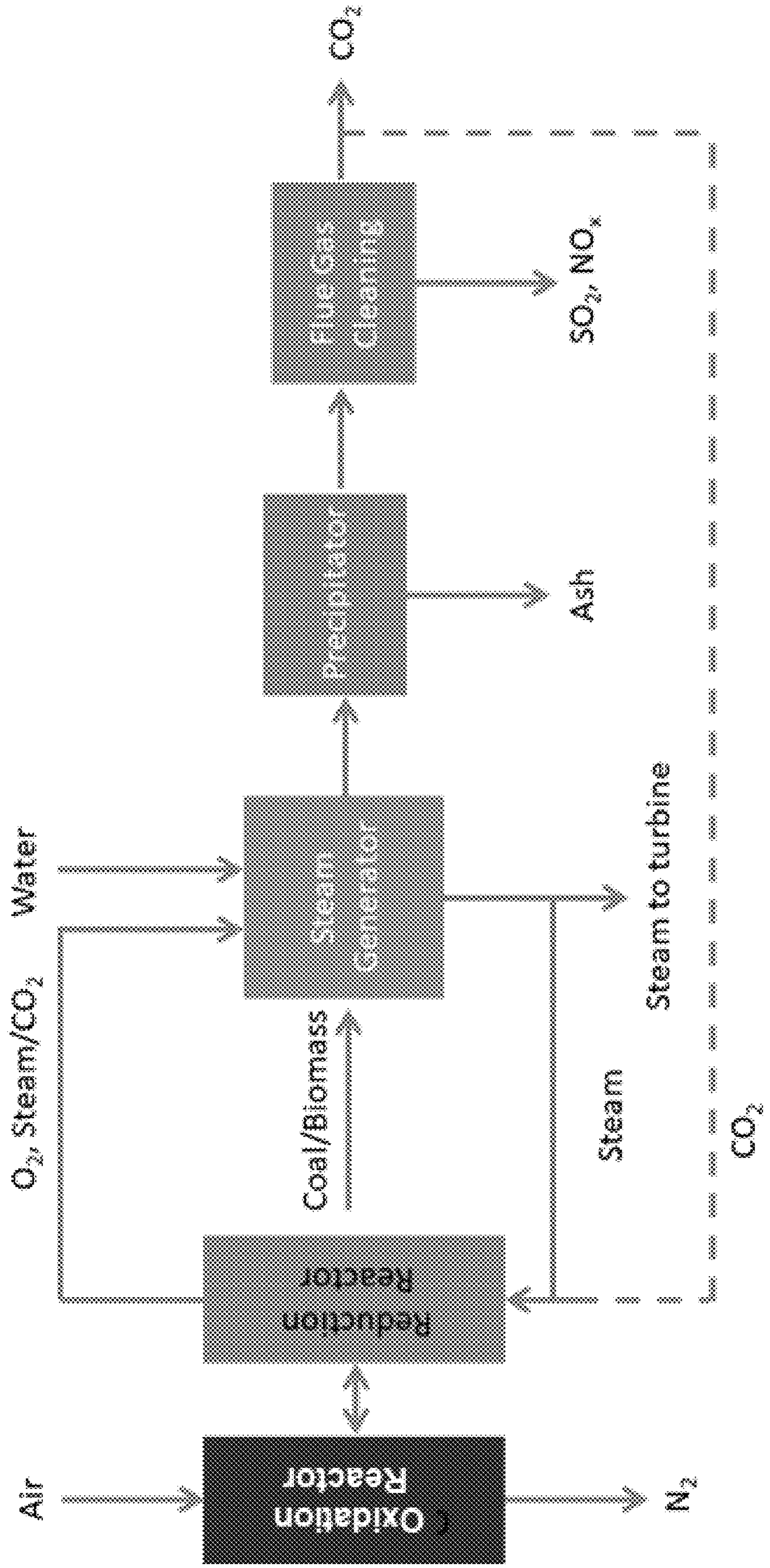
FIG. 12 shows an exemplary schematic for distributed oxygen production for oxyfuel combustion-based carbon dioxide capture using the disclosed perovskites.
Figure 13:
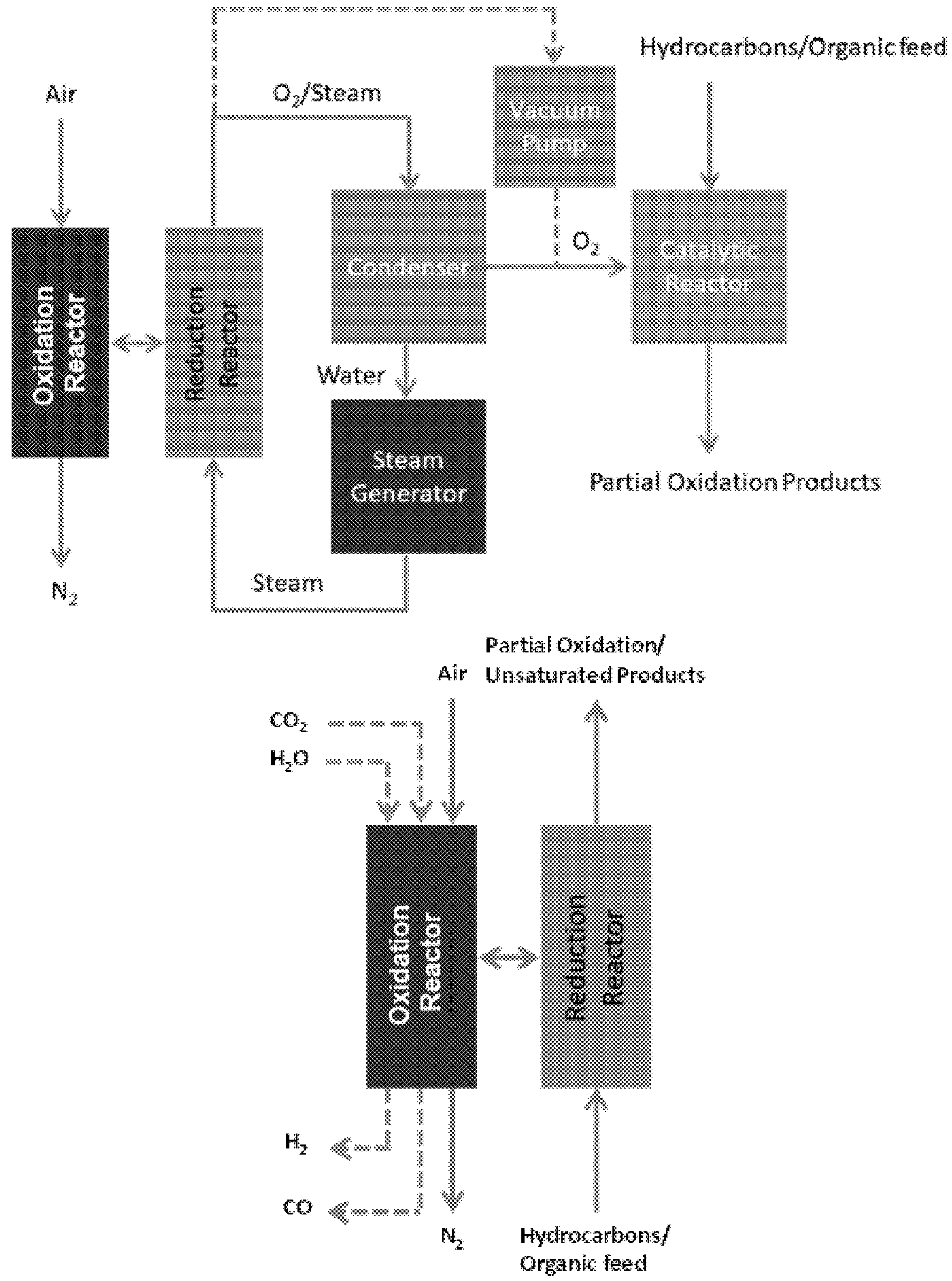
FIG. 13 shows an exemplary schematic for distributed oxygen production for catalytic oxidation reactions using the disclosed perovskites.

[a]The same materials can be used for CL-ODH after surface modification (see FIG. 9D).

TABLE 6

30 Desirable Compositions Predicted by DFT for CL $H_2O/CO_2$ Splitting at 800° C. and 950° C.[a]

| | ΔG (eV) | | | | | |
|---|---|---|---|---|---|---|
| | T = 800° C. | | | T = 950° C. | | |
| δ | 0.25-0.375 | 0.375-0.5 | 0.3125-0.4375 | 0.25-0.375 | 0.375-0.5 | 0.3125-0.4375 |
| LaFeMg-1-0.875-0.125 | 2.45832 | 2.382 | 2.42016 | 2.32419 | 2.21876 | 2.27147 |
| LaFeMn-1-0.375-0.625 | 2.38581 | 2.6456 | 2.5157 | 2.31299 | 2.45227 | 2.38263 |
| LaFeMn-1-0.625-0.375 | 2.05536 | 2.34986 | 2.20261 | 2.02352 | 2.1869 | 2.10521 |
| SrKFeTi-0.875-0.125-0.375-0.625 | 2.18497 | 2.34023 | 2.2626 | 2.0563 | 2.16461 | 2.11046 |
| SrLaFe-0.25-0.75-1 | 1.97339 | 2.52613 | 2.24976 | 1.91929 | 2.36279 | 2.14104 |
| SrLaFeCo-0.125-0.875-0.5-0.5 | 2.2876 | 2.00371 | 2.14566 | 2.1445 | 1.83701 | 1.99076 |
| SrLaFeCu-0.25-0.75-0.875-0.125 | 2.13047 | 2.15533 | 2.1429 | 1.93756 | 2.00529 | 1.97143 |
| SrLaFeMg-0.25-0.75-0.875-0.125 | 2.1067 | 2.05468 | 2.08069 | 2.05644 | 1.92362 | 1.99003 |
| SrLaFeMn-0.125-0.875-0.125-0.875 | 2.71946 | 2.51324 | 2.61635 | 2.54071 | 2.36481 | 2.45276 |
| SrLaFeMn-0.125-0.875-0.25-0.75 | 2.68237 | 2.70599 | 2.69418 | 2.50571 | 2.53732 | 2.52151 |
| SrLaFeMn-0.125-0.875-0.625-0.375 | 2.40517 | 2.26568 | 2.33542 | 2.24194 | 2.11689 | 2.17942 |
| SrLaFeMn-0.25-0.75-0.125-0.875 | 2.14625 | 2.2616 | 2.20392 | 2.03065 | 2.11652 | 2.07359 |
| SrLaFeTi-0.125-0.875-0.875-0.125 | 2.30463 | 2.16573 | 2.23518 | 2.18839 | 1.94655 | 2.06747 |
| SrLaFeTi-0.375-0.625-0.875-0.125 | 2.41955 | 2.03463 | 2.22709 | 2.29078 | 1.86701 | 2.07889 |
| SrLaFeTi-0.5-0.5-0.75-0.25 | 2.03701 | 2.52219 | 2.2796 | 1.91287 | 2.36785 | 2.14036 |
| SrLaFeTi-0.5-0.5-0.875-0.125 | 2.20514 | 2.42297 | 2.31406 | 2.09054 | 2.27787 | 2.1842 |
| SrSmFeCo-0.125-0.875-0.375-0.625 | 2.06316 | 2.12314 | 2.09315 | 1.88194 | 1.93662 | 1.90928 |

TABLE 6-continued

30 Desirable Compositions Predicted by DFT for CL $H_2O/CO_2$ Splitting at 800° C. and 950° C.[a]

| | ΔG (eV) | | | | | |
|---|---|---|---|---|---|---|
| | T = 800° C. | | | T = 950° C. | | |
| δ | 0.25-0.375 | 0.375-0.5 | 0.3125-0.4375 | 0.25-0.375 | 0.375-0.5 | 0.3125-0.4375 |
| SrSmFeCu-0.125-0.875-0.75-0.25 | 1.99977 | 2.33523 | 2.1675 | 1.87774 | 2.17207 | 2.0249 |
| SrSmFeMg-0.5-0.5-0.75-0.25 | 2.07999 | 2.50421 | 2.2921 | 2.00288 | 2.35665 | 2.17977 |
| SrSmFeMn-0.125-0.875-0.75-0.25 | 2.01038 | 2.37883 | 2.1946 | 1.8479 | 2.19871 | 2.0233 |
| SrSmFeMn-0.25-0.75-0.625-0.375 | 2.24499 | 2.0292 | 2.13709 | 2.15159 | 1.88755 | 2.01957 |
| SrSmFeMn-0.5-0.5-0.875-0.125 | 2.20687 | 2.42856 | 2.31772 | 2.10722 | 2.55632 | 2.33177 |
| SrSmFeNi-0.125-0.875-0.875-0.125 | 2.73061 | 2.58286 | 2.65674 | 2.71244 | 2.44917 | 2.5808 |
| SrSmFeTi-0.5-0.5-0.875-0.125 | 2.20175 | 2.22043 | 2.21109 | 2.0546 | 2.04931 | 2.05196 |
| SrSmFeTi-0.875-0.125-0.5-0.5 | 2.04852 | 2.73391 | 2.39122 | 1.90273 | 2.58731 | 2.24502 |
| SrYCo-0.125-0.875-1 | 2.09236 | 2.23061 | 2.16148 | 1.95312 | 2.05051 | 2.00181 |
| SrYFeCu-0.125-0.875-0.875-0.125 | 2.43315 | 2.06862 | 2.25089 | 2.3197 | 1.86956 | 2.09463 |
| SrYFeMn-0.125-0.875-0.875-0.125 | 2.42781 | 2.46479 | 2.4463 | 2.24817 | 2.32291 | 2.28554 |
| SrYFeTi-0.375-0.625-0.875-0.125 | 2.35106 | 2.27019 | 2.31062 | 2.28436 | 2.0596 | 2.17198 |
| YFeCo-1-0.875-0.125 | 2.69223 | 2.44786 | 2.57004 | 2.50957 | 2.26112 | 2.38534 |

[a]The same materials can be used for CL-ODH after surface modification (see FIG. 9D).

TABLE 7

55 Desirable Compositions Predicted by DFT for CL $H_2O/CO_2$ Splitting at 800° C. or 950° C.[a]

| | ΔG (eV) | | | | | |
|---|---|---|---|---|---|---|
| | T = 800° C. | | | T = 950° C. | | |
| δ | 0-0.125 | 0.125-0.25 | 0.0625-0.1875 | 0-0.125 | 0.125-0.25 | 0.0625-0.1875 |
| LaFeTi-1-0.25-0.75 | 2.61833 | 0.37584 | 1.49708 | 2.21279 | −0.02466 | 1.09406 |
| SrBaFeTi-0.125-0.875-0.25-0.75 | 2.73005 | −0.9878 | 0.87112 | 2.56834 | −1.14021 | 0.71406 |
| SrBaFeTi-0.25-0.75-0.125-0.875 | 1.53297 | 3.16408 | 2.34853 | 1.43513 | 3.0434 | 2.23927 |
| SrBaFeTi-0.5-0.5-0.125-0.875 | 2.52477 | 0.56256 | 1.54367 | 2.39961 | 0.39974 | 1.39967 |
| SrBaFeTi-0.625-0.375-0.25-0.75 | 1.02045 | 2.69068 | 1.85557 | 0.99084 | 2.57603 | 1.78343 |
| SrBaTi-0.375-0.625-1 | 1.10089 | 4.01777 | 2.55933 | 0.72784 | 3.91838 | 2.32311 |
| SrBaTi-0.5-0.5-1 | 1.01364 | 4.31933 | 2.66649 | 0.61839 | 4.22356 | 2.42098 |
| SrBaTi-0.625-0.375-1 | 1.21633 | 3.51969 | 2.36801 | 0.84566 | 3.34673 | 2.0962 |
| SrBaTi-0.75-0.25-1 | 1.10322 | 3.48444 | 2.29383 | 0.62956 | 3.29501 | 1.96229 |
| SrBaTi-0.875-0.125-1 | 0.76827 | 3.61074 | 2.18951 | 0.30147 | 3.45844 | 1.87996 |
| SrCaFeTi-0.375-0.625-0.125-0.875 | 2.98525 | 1.86667 | 2.42596 | 2.86675 | 1.72369 | 2.29522 |
| SrCaFeTi-0.625-0.375-0.125-0.875 | 2.75525 | 1.72026 | 2.23776 | 2.64512 | 1.56995 | 2.10753 |
| SrCaFeTi-0.625-0.375-0.25-0.75 | 0.85242 | 2.21989 | 1.53615 | 0.76839 | 2.09476 | 1.43158 |
| SrCaTi-0.625-0.375-1 | 0.18582 | 4.73157 | 2.45869 | −0.29962 | 4.69243 | 2.19641 |
| SrKFeTi-0.875-0.125-0.125-0.875 | 2.12724 | 0.47268 | 1.29996 | 2.07292 | 0.33653 | 1.20472 |
| SrLaFeTi-0.125-0.875-0.125-0.875 | 0.44277 | 4.07956 | 2.26117 | 0.18162 | 4.01982 | 2.10072 |
| SrLaFeTi-0.25-0.75-0.5-0.5 | 0.82971 | 3.59693 | 2.21332 | 0.61209 | 3.35133 | 1.98171 |
| SrLaFeTi-0.25-0.75-0.625-0.375 | 2.07148 | 3.18229 | 2.62689 | 2.03791 | 2.96087 | 2.49939 |
| SrLaFeTi-0.375-0.625-0.5-0.5 | 1.78934 | 3.25536 | 2.52235 | 1.76537 | 3.13098 | 2.44817 |
| SrLaFeTi-0.375-0.625-0.625-0.375 | 2.4382 | 2.45988 | 2.44904 | 2.32327 | 2.33526 | 2.32927 |
| SrLaFeTi-0.5-0.5-0.125-0.875 | 1.09986 | 3.69375 | 2.3968 | 0.59966 | 3.57172 | 2.08569 |
| SrLaFeTi-0.5-0.5-0.375-0.625 | 2.64907 | 3.91694 | 3.283 | 2.61296 | 3.75229 | 3.18262 |
| SrLaFeTi-0.625-0.375-0.375-0.625 | 2.2582 | 3.43892 | 2.84856 | 2.18278 | 3.29976 | 2.74127 |
| SrLaFeTi-0.625-0.375-0.5-0.5 | 2.00979 | 1.95869 | 1.98424 | 1.88632 | 1.86521 | 1.87577 |
| SrLaFeTi-0.875-0.125-0.25-0.75 | 1.76828 | 2.96064 | 2.36446 | 1.65406 | 2.88835 | 2.27121 |
| SrLaTi-0.25-0.75-1 | 2.26366 | 5.18142 | 3.72254 | 2.09363 | 5.15595 | 3.62479 |
| SrLaTi-0.375-0.625-1 | 0.35367 | 4.74228 | 2.54797 | −0.02842 | 4.65147 | 2.31153 |
| SrLaTi-0.5-0.5-1 | 1.04013 | 3.80752 | 2.42383 | 0.56101 | 3.61374 | 2.08737 |
| SrLaTi-0.875-0.125-1 | 0.74824 | 4.20988 | 2.47906 | 0.18411 | 4.13168 | 2.1579 |
| SrSmFeMn-0.125-0.875-0.25-0.75 | 0.90949 | 2.67563 | 1.79256 | 0.7773 | 2.53358 | 1.65544 |
| SrSmFeTi-0.125-0.875-0.25-0.75 | 0.64527 | 4.55575 | 2.60051 | 0.47218 | 4.4146 | 2.44339 |
| SrSmFeTi-0.125-0.875-0.375-0.625 | 2.5702 | 5.77071 | 4.17046 | 2.48114 | 5.60411 | 4.04262 |
| SrSmFeTi-0.125-0.875-0.625-0.375 | 2.13477 | 3.19685 | 2.66581 | 1.99074 | 3.10755 | 2.54914 |
| SrSmFeTi-0.375-0.625-0.375-0.625 | 2.62259 | 4.32369 | 3.47314 | 2.52522 | 4.19108 | 3.35815 |
| SrSmFeTi-0.375-0.625-0.5-0.5 | 1.61553 | 2.58371 | 2.09962 | 1.48445 | 2.44366 | 1.96405 |
| SrSmFeTi-0.5-0.5-0.125-0.875 | 0.23435 | 4.60965 | 2.422 | 0.06879 | 4.51021 | 2.2895 |
| SrSmFeTi-0.625-0.375-0.375-0.625 | 2.30435 | 3.12287 | 2.71361 | 2.17399 | 2.99457 | 2.58428 |
| SrSmFeTi-0.875-0.125-0.25-0.75 | 1.91979 | 2.6695 | 2.29464 | 1.86213 | 2.53912 | 2.20062 |
| SrSmTi-0.375-0.625-1 | 0.73188 | 4.74136 | 2.73662 | 0.50183 | 4.70165 | 2.60174 |
| SrSmTi-0.75-0.25-1 | 0.2649 | 4.47324 | 2.36907 | −0.3035 | 4.39566 | 2.04608 |
| SrTi-1-1 | 0.03399 | 4.19383 | 2.11391 | −0.68592 | 4.16466 | 1.73937 |
| SrYFeTi-0.125-0.875-0.25-0.75 | −0.06104 | 4.84417 | 2.39156 | −0.15373 | 4.71249 | 2.27938 |
| SrYFeTi-0.125-0.875-0.625-0.375 | 1.16916 | 3.4309 | 2.30003 | 1.06842 | 3.28864 | 2.17853 |
| SrYFeTi-0.125-0.875-0.875-0.125 | −6.57365 | 2.58122 | −1.99622 | −6.85329 | 2.42008 | −2.2166 |

TABLE 7-continued

55 Desirable Compositions Predicted by DFT for CL $H_2O/CO_2$ Splitting at 800° C. or 950° C.[a]

| | ΔG (eV) | | | | | |
|---|---|---|---|---|---|---|
| | T = 800° C. | | | T = 950° C. | | |
| δ | 0-0.125 | 0.125-0.25 | 0.0625-0.1875 | 0-0.125 | 0.125-0.25 | 0.0625-0.1875 |
| SrYFeTi-0.375-0.625-0.5-0.5 | 1.12713 | 3.23622 | 2.18168 | 1.03727 | 3.10036 | 2.06882 |
| SrYFeTi-0.375-0.625-0.625-0.375 | 2.53148 | 2.24377 | 2.38763 | 2.42814 | 2.13511 | 2.28163 |
| SrYFeTi-0.5-0.5-0.125-0.875 | −0.02339 | 4.24864 | 2.11262 | −0.14214 | 4.11895 | 1.9884 |
| SrYFeTi-0.5-0.5-0.25-0.75 | 2.4195 | 3.92455 | 3.17202 | 2.24297 | 3.79338 | 3.01818 |
| SrYFeTi-0.5-0.5-0.375-0.625 | 2.4856 | 2.82335 | 2.65448 | 2.37062 | 2.69478 | 2.5327 |
| SrYFeTi-0.5-0.5-0.5-0.5 | −1.50006 | 2.04429 | 0.27212 | −1.67772 | 1.92026 | 0.12127 |
| SrYFeTi-0.625-0.375-0.375-0.625 | 2.25748 | 3.28948 | 2.77348 | 2.13157 | 3.14408 | 2.63782 |
| SrYFeTi-0.75-0.25-0.25-0.75 | 2.71785 | 4.15441 | 3.43613 | 2.61738 | 3.99223 | 3.3048 |
| SrYFeTi-0.875-0.125-0.125-0.875 | 2.22825 | 3.67554 | 2.95189 | 2.10701 | 3.53614 | 2.82157 |
| SrYTi-0.625-0.375-1 | 1.99003 | 4.0987 | 3.04437 | 1.83109 | 3.94363 | 2.88736 |
| SrYTi-0.75-0.25-1 | −0.26527 | 4.22596 | 1.98035 | −0.82876 | 4.08095 | 1.62609 |

[a]The same materials can be used for CL-ODH after surface modification (see FIG. 9D).

TABLE 8

Experimental TPD in 50% and 5% $O_2$ from ML Predicted 5 Cation Samples $Sr_{0.875}A'_{0.125}Fe_{0.75}Co_{0.125}Ni_{0.125}O_5$ for CLAS

| Material (A') | Ca | | K | | La | | Sm | |
|---|---|---|---|---|---|---|---|---|
| Oxygen Environment | 50% | 5% | 50% | 5% | 50% | 5% | 50% | 5% |
| Capacity | 4.05% | 336% | 4.56% | 5.01% | 3.28% | 3.61% | 4.45% | 3.31% |
| Recovery | 98.03% | 98.71% | 97.50% | 97.05% | 99.06% | 98.84% | 97.74% | 98.87% |
| Initial Temperature Peak (° C.) | 319 | 316 | 279 | 261 | 312 | 266 | 265 | 264 |
| High Temperature Peak (° C.) | 791 | 780 | 785 | 807 | 761 | 776 | 740 | 780 |

TABLE 9

Experimental Performance of the DFT/ML Predicted Materials for CL $CO_2$ Splitting

| $Sr_{1-x}A_xFe_{1-y}B_yO_3$ | Model Predicted Composition | Temperature | Gas Flow+ | Results |
|---|---|---|---|---|
| A = Y; B = Ti | $Sr_{0.5}Y_{0.5}Fe_{0.125}Ti_{0.875}O_{3-\delta}$ | 950° C. | $CH_4/N_2$ = 2.5/22.5<br>$CO_2/N_2$ = 2.5/22.5 | $X_{CH4}$~100%,<br>$S_{CO}$ = 98%,<br>$X_{CO2}$ = 99%,<br>$Y_{syngas}$ = 98%<br>Oxygen capacity = 0.70 wt % |
| A = Y; B = Ti | $Sr_{0.375}Y_{0.825}Fe_{0.5}Ti_{0.5}O_{3-\delta}$ | 950° C. | $CH_4/N_2$ = 2.5/22.5<br>$CO_2/N_2$ = 2.5/22.5 | $X_{CH4}$~100%,<br>$S_{CO}$ = 96%,<br>$X_{CO2}$ = 96%,<br>$Y_{syngas}$ = 96%<br>Oxygen capacity = 0.69 wt % |
| A = Y; B = Ti | $Sr_{0.5}Y_{0.5}Fe_{0.375}Ti_{0.625}O_{3-\delta}$ | 950° C. | $CH_4/N_2$ = 2.5/22.5<br>$CO_2/N_2$ = 2.5/22.5 | $X_{CH4}$~100%,<br>$S_{CO}$ = 96%,<br>$X_{CO2}$ = 96%,<br>$Y_{syngas}$ = 96%<br>Oxygen capacity = 0.69 wt % |
| A = Sm; B = Ti | $Sr_{0.375}Sm_{0.625}Fe_{0.375}Ti_{0.625}O_{3-\delta}$ | 950° C. | $CH_4/N_2$ = 2.5/22.5<br>$CO_2/N_2$ = 2.5/22.5 | $X_{CH4}$~100%,<br>$S_{CO}$ = 98%,<br>$X_{CO2}$ = 99%,<br>$Y_{syngas}$ = 97%<br>Oxygen capacity = 0.70 wt % |
| A = La; B = Mn | $LaFe_{0.35}Mn_{0.65}O_{3-\delta}$ | 950° C. | $CH_4/N_2$ = 2.5/22.5<br>$CO_2/N_2$ = 2.5/22.5 | $X_{CH4}$ = 20%,<br>$S_{CO}$ = 80%,<br>$X_{CO2}$ = 23%,<br>$Y_{syngas}$ = 16%<br>Oxygen capacity= 0.15 wt % |
| | $LaFe_{0.35}Mn_{0.65}O_{3-\delta}$<br>(1 wt % Ru impregnated) | 950° C. | $CH_4/N_2$ = 2.5/22.5<br>$CO_2$/N2 = 2.5/22.5 | $X_{CH4}$~100%,<br>$S_{CO}$ = 93%,<br>$X_{CO2}$ = 93%,<br>$Y_{syngas}$ = 93%<br>Oxygen capacity = 0.66 wt % |
| A = Y; B = Co | $YFe_{0.875}Co_{0.125}O_{3-\delta}$ | 95° C. | $CH_4/N_2$ = 2.5/22.5<br>$CO_2/N_2$ = 2.5/22.5 | $X_{CH4}$~100%,<br>$S_{CO}$ = 80%,<br>$X_{CO2}$ = 88%,<br>$Y_{syngas}$ =80%<br>Oxygen capacity = 0.63 wt % |

TABLE 9-continued

Experimental Performance of the DFT/ML Predicted Materials for CL $CO_2$ Splitting

| $Sr_{1-x}A_xFe_{1-y}B_yO_3$ | Model Predicted Composition | Temperature | Gas Flow+ | Results |
|---|---|---|---|---|
| A = Sm; B = Cu | $Sr_{0.125}Sm_{0.875}Fe_{0.75}Cu_{0.25}O_{3-\delta}$ | 950° C. | $CH_4/N_2$ = 2.5/22.5<br>$CO_2$/N2 = 2.5/22.5 | $X_{CH4}$ = 58%,<br>$S_{CO}$ = 90%,<br>$X_{CO2}$ = 60%,<br>$Y_{syngas}$ = 52%<br>Oxygen capacity = 0.41 wt % |
| | $Sr_{0.125}Sm_{0.875}Fe_{0.75}Cu_{0.25}O_{3-\delta}$ (0.5 wt % Rh impregnated) | 950° C. | $CH_4/N_2$ = 2.5/22.5<br>$CO_2/N_2$ = 2.5/22.5 | $X_{CH4}$ = 98%,<br>$S_{CO}$ = 89%,<br>$X_{CO2}$ = 88%,<br>$Y_{syngas}$ = 87%<br>Oxygen capacity = 0.63 wt % |
| $A_1$ = La, $A_2$ = Sm; B = Ti | $Sr_{0.375}La_{0.375}Sm_{0.25}Fe_{0.75}Ti_{0.25}O_{3-\delta}$ (ML predicted) | 950° C. | $CH_4/N_2$ = 2.5/22.5<br>$CO_2/N_2$ = 2.5/22.5 | $X_{CH4}$ = 77%,<br>$S_{CO}$ = 93%,<br>$X_{CO2}$ = 83%,<br>$Y_{syngas}$ = 71%<br>Oxygen capacity = 0.59 wt % |
| $A_1$ = La, $A_2$ = Sm; B = Ti | $Sr_{0.375}La_{0.5}Sm_{0.125}Fe_{0.75}Ti_{0.25}O_{3-\delta}$ (ML predicted) | 950° C. | $CH_4/N_2$ = 2.5/22.5<br>$CO_2/N_2$ = 2.5/22.5 | $X_{CH4}$ = 71%,<br>$S_{CO}$ = 93%,<br>$X_{CO2}$ = 80%,<br>$Y_{syngas}$ = 71%<br>Oxygen capacity = 0.57 wt % |
| $A_1$ = La, $A_2$ = Sm; B = Ti | $Sr_{0.125}La_{0.625}Sm_{0.25}Fe_{0.875}Ti_{0.125}O_{3-\delta}$ (ML predicted) | 950° C. | $CH_4/N_2$ = 2.5/22.5<br>$CO_2/N_2$ = 2.5/22.5 | $X_{CH4}$ = 80%,<br>$S_{CO}$ = 90%,<br>$X_{CO2}$ = 90%,<br>$Y_{syngas}$ = 72%<br>Oxygen capacity = 0.64 wt % |

It should be emphasized that the above-described embodiments of the present disclosure are merely possible examples of implementations set forth for a clear understanding of the principles of the disclosure. Many variations and modifications may be made to the above-described embodiment(s) without departing substantially from the spirit and principles of the disclosure. All such modifications and variations are intended to be included herein within the scope of this disclosure and protected by the following claims.

REFERENCES

1. Abraham, A. et al. Front. Neuroinform., 2014, 8, 14.
2. Adánez-Rubio, I. et al. Chem. Eng. J., 2014, 256, 69-84.
3. Al-Shankiti, I. et al. Solar Energy, 2017, 156, 21-29.
4. Anisimov, V. I. et al. Physical review. B, Condensed matter, 1991, 44, 943-954.
5. Arjmand, M. et al. Energy & fuels, 2014, 28, 1312-1324.
6. Banerjee, R. et al. ACS Sustainable Chemistry & Engineering, 2020, 8, 17022-17032.
7. Bartel, C. J. et al. Sci. Adv., 2019, 5, eaav0693.
8. Bhaysar, S. et al. Catal. Today, 2014, 228, 96-105.
9. Blöchl, P. Physical review. B, Condensed matter, 1994, 50, 17953.
10. Breiman, L. Machine Learning, 2001, 45, 5-32.
11. Bui, M. et al. Energy Environ. Sci., 2018, 11, 1062-1176.
12. Buitinck, L. et al. 2013, arXiv preprint arXiv, 1309.0238.
13. Bulfin, B. et al. Chem. Eng. Sci., 2019, 203, 68-75.
14. Bulfin, B. et al. J. Mater. Chem. A, 2017, 5, 7912-7919.
15. Butler, K. T. et al. Nature, 2018, 559, 547-555.
16. Cabello, A. et al. Applied Energy, 2021, 287, 116557.
17. Campbell, C. et al. Synthesis lectures on artificial intelligence and machine learning, 2011, 5, 1-95.
18. Carrillo, A. J. et al. ACS Applied Energy Materials, 2020, 3, 4569-4579.
19. Carrillo, A. J. et al. Advanced Energy Materials, 2019, 9, 1803886.
20. Chen, B. W. et al. Chem. Rev., 2020, 121, 1007-1048.
21. Chen, S. et al. J. Am. Chem. Soc., 2019, 141, 18653-18657.
22. Chuayboon, S. et al. Frontiers in Energy Research, 2020, 8, 128.
23. Das, T. et al. Journal of Materials Chemistry A, 2017, 5, 4493-4506.
24. Daza, Y. A. et al. Industrial & Engineering Chemistry Research, 2014, 53, 5828-5837.
25. De Vos, Y. et al. Catalysts, 2020, 10, 926.
26. Deng, G. et al. Applied Energy, 2019, 253, 113534.
27. Dou, J. et al. ChemSusChem, 2020, 13, 385-393.
28. Dou, J. et al. Journal of Physics: Energy, 2020, 2, 025007.
29. Emery, A. A. et al. Chem. Mater., 2016, 28, 5621-5634.
30. Fan, L.-S. et al. Energy Environ. Sci., 2012, 5, 7254-7280.
31. Feng, Y. et al. Fuel, 2018, 229, 88-94.
32. Feng, Y. et al. Fuel, 2019, 236, 1057-1064.
33. Frisch, M. J. et al. Gaussian 16, revision C. 01; Gaussian Inc.: Wallingford, Conn., USA., 2016.
34. Galinsky, N. et al. Applied Energy, 2016, 174, 80-87.
35. Gao, W. et al., Nat. Energy, 2018, 3, 1067-1075.
36. Gao, Y. et al. Science Advances, 2020, 6, eaaz9339.
37. Grke, R. H. et al. International Journal of Greenhouse Gas Control, 2020, 94, 102891.
38. Hare, B. J. et al. ACS Catalysis, 2018, 8, 3021-3029.
39. Haribal, V. P. et al. Advanced Energy Materials, 2019, 9, 1901963.
40. Haribal, V. P. et al. ChemSusChem, 2017, 10, 3402-3408.
41. Hase, F. et al. Nature Communications, 2020, 11, 1-11.

42. Hautier, G. et al. Physical review. B, Condensed matter, 2011, 85, 155208.
43. He, F. et al. Int. J. Hydrogen Energy, 2019, 44, 10265-10276.
44. Huang, B. et al. Chem. Rev., 2021, 121, 10001-10036.
45. Iftikhar, S. et al., Energy Fuels, 2021, 35, 13921-13929.
46. Jackson, A. J. et al., J. Mater. Chem. A, 2014, 2, 7829-7836.
47. Jafarian, M. et al. Chem. Eng. Res. Des., 2017, 120, 69-81.
48. Jain, A. et al. Computational Materials Science, 2011, 50, 2295-2310.
49. Jia, T. et al. Phys. Chem. Chem. Phys., 2020, 22.
50. Jian, D. et al. ACS Sustainable Chemistry And Engineering, 2018, 6, 15528-15540.
51. Jiang, Q. et al. Journal of Materials Chemistry A, 2020, 8, 13173-13182.
52. Jiang, S. et al., Scr. Mater., 2018, 142, 116-120.
53. Josua, V. et al. Energy Technology, 2018.
54. Kramer, O. Dimensionality reduction with unsupervised nearest neighbors, Springer, 2013.
55. Kresse, G. G. et al. Physical review. B, Condensed matter, 1996, 54, 11169.
56. Krzystowczyk, E. et al. Phys. Chem. Chem. Phys., 2020, 22, 8924-8932.
57. Lau, C. Y. et al. Energy Environ. Sci., 2017, 10, 818-831.
58. Lee, Y. L. et al. Physical Review B, 2009, 80, 308-310.
59. Li, D. et al. Energy Technology, 2020, 8, 1900925.
60. Li, Y. et al. Energy & Fuels, 2020, 34, 11186-11193.
61. Liu, X. et al. Mater. Sci.: Mater. Electron., 2009, 20, 323-327.
62. Long, Y. et al. Journal of the Energy Institute, 2021, 94, 199-209.
63. Luongo, G. et al. Phys. Chem. Chem. Phys., 2020, 22, 9272-9282.
64. Ma, S. et al. Energy & Fuels, 2017, 31, 8001-8013.
65. Maiti, D. et al. Energy Environ. Sci., 2018, 11, 648-659.
66. Maiti, D. et al. Journal of Materials Chemistry A, 2016, 4, 5137-5148.
67. Marek, E. et al. Applied Energy, 2018, 223, 369-382.
68. Miao, Z. et al. Fuel, 2020, 279, 118547.
69. Michalsky, R. et al. Catal. Today, 2017, 286, 124-130.
70. Mishra, A. et al. Chem. Mater., 2018, 31, 689-698.
71. Miura, N. et al. Industrial & Engineering Chemistry Research, 2016, 55, 3091-3096.
72. Moldenhauer, P. et al. Energy Technology, 2020, 8, 2000069.
73. Moosavi, S. M. et al. J. Am. Chem. Soc., 2020, 142, 20273-20287.
74. Muhich, C. L. et al. Int. J. Hydrogen Energy, 2018, 43, 18814-18831.
75. Nalbandian, L. et al. Int. J. Hydrogen Energy, 2011, 36, 6657-6670.
76. Neal, L. M. et al. ACS Catalysis, 2014, 4, 3560-3569.
77. Pachler, R. F. et al. International Journal of Greenhouse Gas Control, 2018, 71, 86-94.
78. Panapitiya, G. et al. J. Am. Chem. Soc., 2018, 140, 17508-17514.
79. Pasha, G. et al. Journal of research (Science), 2004, 15, 97-106.
80. Perdew, J. et al. Phys. Rev. Lett., 1997, 77, 3865.
81. Qin, L. et al. Applied Catalysis B: Environmental, 2018, 235, 143-149.
82. Qin, L. et al. ChemCatChem, 2021, 13, 617-626.
83. Ranstam, J. et al. Journal of British Surgery, 2018, 105, 1348-1348.
84. Schmidt, J. et al. npj Computational Materials, 2019, 5, 1-36.
85. Shafiefarhood, A. et al. ChemCatChem, 2014, 6, 790-799.
86. Shafiefarhood, A. et al. J. Mater. Chem. A, 2017, 5, 11930-11939.
87. Shah, K. et al. Energy & fuels, 2012, 26, 2038-2045.
88. Shen, Y. et al. Journal of the Energy Institute, 2019, 92, 239-246.
89. Shi, Y. et al. J. Mater. Chem. A, 2022, 10, 2256-2270.
90. Simm, J. et al. IEICE TRANSACTIONS on Information and Systems, 2014, 97, 1677-1681.
91. Singstock, N. R. et al. Advanced Energy Materials, 2020, 10, 2000685.
92. Stoffel, R. P. et al. Angew. Chem., Int. Ed., 2010, 49, 5242-5266.
93. Takeda, T. et al. J. Phys. Soc. Jpn., 1972, 33, 967-969.
94. Tang, L. et al. J. Am. Ceram. Soc., 2021, 104, 1953-1958.
95. Taylor, D. D. et al. Chem. Mater., 2016, 28, 3951-3960.
96. Togo, A. et al. *Scripta* Mater., 2015, 108, 1-5.
97. Torrisi, S. B. et al. NPJ Comput. Mater. 2020, 6, 1-11.
98. Vente, J. F. et al. J. Solid State Electrochem., 2006, 10, 581-588.
99. Vieten, J. et al. Energy Environ. Sci., 2019, 12, 1369-1384.
100. Vieten, J. et al. Energy Technol., 2019, 7, 131-139.
101. Vieten, J. et al. Solid State Ionics, 2017, 308, 149-155.
102. Vieten, J. et al. J. Mater. Chem. A, 2016, 35, 13652-13659.
103. Walle, A. V. D. et al. Calphad-computer Coupling of Phase Diagrams & Thermochemistry, 2013, 42, 13-18.
104. Wang, K. et al. Energy & Fuels, 2020, 34, 3449-3457.
105. Wang, X. et al. Chem. Mater., 2021, 33, 2446-2456.
106. Wang, X. et al. J. Am. Chem. Soc., 2020, 142, 7737-7743.
107. Wang, Y. et al. Mater. Lett., 2001, 49, 361-364.
108. Wei, H. et al. J. Phys. Chem. Lett., 2019, 10, 6026-6031.
109. Williams, C. K. et al. Gaussian processes for machine learning, MIT press Cambridge, Mass., 2006.
110. Wu, H. C. et al. Ind. Eng. Chem. Res., 2017, 56, 6057-6064.
111. Yan, Y. et al. Chem. Eng. J., 2020, 387, 124072.
112. Yang, Z. et al. Industrial & engineering chemistry research, 2002, 41, 2775-2784.
113. Yang, Z. et al. Industrial & engineering chemistry research, 2003, 42, 4376-4381.
114. Zeng, L. et al. Nature Reviews Chemistry, 2018, 2, 349-364.
115. Zhang, J. et al. Science advances, 2017, 3, e1701184.
116. Zhao, K. et al. Applied Energy, 2016, 168, 193-203.
117. Zhao, K. et al. Int. J. Hydrogen Energy, 2014, 39, 3243-3252.
118. Zhao, K. et al. Korean J. Chem. Eng., 2017, 34, 1651-1660.
119. Zhu, X. et al. ACS Catalysis, 2018, 8, 8213-8236.
120. Zhu, X. et al. Energy Environ. Sci., 2020, 13, 772-804.
121. Zhu, X. et al. Nature communications, 2021, 12, 1-11.

What is claimed is:

1. An oxygen-deficient mixed metal perovskite comprising the formula $Sr_x(A/A')_{1-x}Fe_y(B/B')_{1-y}O_{3-\delta}$, wherein $Sr_x(A/A')_{1-x}Fe_y(B/B')_{1-y}O_{3-\delta}$ is selected from the group consisting of $Sr_{0.75}Ca_{0.25}Fe_{0.75}Mn_{0.25}O_{3-\delta}$, $Sr_{0.875}Ca_{0.125}Fe_{0.625}Mg_{0.375}O_{3-\delta}$, $Sr_{0.75}Ca_{0.25}CoO_{3-\delta}$, $Sr_{0.875}K_{0.125}CoO_{3-\delta}$, $Sr_{0.875}La_{0.125}Fe_{0.75}Cu_{0.25}O_{3-\delta}$, $Sr_{0.875}Y_{0.125}Fe_{0.75}Ni_{0.25}O_{3-\delta}$, $Sr_{0.625}Ca_{0.375}Fe_{0.75}Cu_{0.25}O_{3-\delta}$, $Sr_{0.875}Ba_{0.125}Fe_{0.375}Mn_{0.625}O_{3-\delta}$, $Sr_{0.875}K_{0.125}Fe_{0.75}Co_{0.125}Ni_{0.125}O_{3-\delta}$, $Sr_{0.5}Ba_{0.5}Fe_{0.625}Mg_{0.25}Ti_{0.125}O_{3-\delta}$, $SrFe_{0.5}Cu_{0.125}Mn_{0.125}Mg_{0.25}O_{3-\delta}$, $Sr_{0.875}Ca_{0.125}Fe_{0.75}Co_{0.125}Ni_{0.125}O_{3-\delta}$, $Sr_{0.875}La_{0.125}Fe_{0.75}Co_{0.125}Ni_{0.125}O_{3-\delta}$, $Sr_{0.875}Sm_{0.125}Fe_{0.75}Co_{0.125}Ni_{0.125}O_{3-\delta}$, $Sr_{0.5}Y_{0.5}Fe_{0.125}Ti_{0.875}O_{3-\delta}$, $Sr_{0.375}Y_{0.625}Fe_{0.5}Ti_{0.5}O_{3-\delta}$, $Sr_{0.5}Y_{0.5}Fe_{0.375}Ti_{0.625}O_{3-\delta}$, $Sr_{0.375}Sm_{0.625}Fe_{0.375}Ti_{0.625}O_{3-\delta}$, $Sr_{0.125}Sm_{0.875}Fe_{0.75}Cu_{0.25}O_{3-\delta}$, $Sr_{0.375}La_{0.375}Sm_{0.25}Fe_{0.75}Ti_{0.25}O_{3-\delta}$, $Sr_{0.375}La_{0.5}Sm_{0.125}Fe_{0.75}Ti_{0.25}O_{3-\delta}$, and $Sr_{0.125}La_{0.625}Sm_{0.25}Fe_{0.875}Ti_{0.125}O_{3-\delta}$.

2. The oxygen-deficient mixed metal perovskite of claim 1, wherein the oxygen-deficient mixed metal perovskite comprises 4 or 5 cations.

3. The oxygen-deficient mixed metal perovskite of claim 1, wherein A is selected from Ba, Ca, K, La, Sm, Y, or a combination of La and Sm.

4. The oxygen-deficient mixed metal perovskite of claim 1, wherein B is selected from Co, Mn, Mg, Cu, Ni, a combination of Co and Ni, a combination of Mg and Ti, or a combination of Mn and Mg.

5. The oxygen-deficient mixed metal perovskite of claim 1, wherein the oxygen-deficient mixed metal perovskite further comprises up to 1 wt % Ru.

6. The oxygen-deficient mixed metal perovskite of claim 1, wherein the oxygen-deficient mixed metal perovskite further comprises up to 0.5 wt % Rh.

7. The oxygen-deficient mixed metal perovskite of claim 1, wherein the oxygen-deficient mixed metal perovskite is further loaded with up to 30 wt % alkali metal salt, mixed alkali metal oxide, or any combination thereof.

8. The oxygen-deficient mixed metal perovskite of claim 7, wherein the alkali metal salt or mixed alkali metal oxide comprises $Na_2WO_4$, $Na_2MoO_4$, $Na_2W_2O_7$, $Na_4Mg(WO_4)_3$, $Li_2CO_3$, $Na_2CO_3$, $K_2CO_3$, NaBr, LiBr, KBr, LiI, NaI, KI, $Na_2W_4O_{13}$, $KFeO_2$, or any combination thereof.

9. The oxygen-deficient mixed metal perovskite of claim 1, wherein y is from 0.125 to 0.875.

10. The oxygen-deficient mixed metal perovskite of claim 1, wherein y is 0.

11. A method for chemical looping air separation (CLAS), the method comprising:

(i) contacting a gas mixture comprising oxygen with the oxygen-deficient mixed metal perovskite of claim 1, wherein the contacting creates a reduced level of oxygen deficiency in the perovskite; and (ii) exposing the perovskite having the reduced level of oxygen deficiency to a vacuum or steam purge to release concentrated oxygen while recreating the oxygen-deficient perovskite of (i).

12. The method of claim 11, wherein the gas mixture comprises an oxygen partial pressure of from about 0.01 atm to about 0.2 atm prior to performing the method.

13. The method of claim 11, wherein the gas mixture is substantially free of oxygen following performing the method.

14. A method for chemical looping (CL) $CO_2$ splitting, the method comprising contacting a gas mixture comprising carbon dioxide with the oxygen-deficient mixed metal perovskite of claim 1.

15. The method of claim 14, wherein at least 80% of the carbon dioxide is converted to carbon monoxide and oxygen.

16. A method for chemical looping methane conversion, the method comprising contacting a gas mixture comprising methane with the oxygen-deficient mixed metal perovskite of claim 1.

17. The method of claim 16, wherein at least 70% of the methane is converted to syngas.

18. A method for producing olefinic compounds using the oxygen-deficient mixed metal perovskite of claim 1, comprising:

(i) contacting the oxygen-deficient mixed metal perovskite or the redox catalyst with one or more dehydrogenation reactants;

(ii) dehydrogenating the one or more dehydrogenation reactants to provide an olefinic compound and hydrogen and a reduced perovskite; and (iii) reoxidizing the reduced perovskite by introducing a gaseous oxidant comprising oxygen to the reduced perovskite to form a reoxidized perovskite; and (iv) re-using the reoxidized perovskite for a subsequent dehydrogenation and selective hydrogen combustion;

wherein at least 30% of the hydrogen released during step (ii) is converted using a lattice oxygen from the perovskite, resulting in formation of steam.

* * * * *